United States Patent
Simpson et al.

(10) Patent No.: US 6,821,754 B2
(45) Date of Patent: Nov. 23, 2004

(54) *STAPHYLOCOCCUS AUREUS* GENES AND POLYPEPTIDES

(75) Inventors: Andrew J. G. Simpson, Sao Paulo (BR); Gil H. Choi, Rockville, MD (US)

(73) Assignees: Human Genome Sciences, Inc., Rockville, MD (US); Ludwig Institute for Cancer Research, Sao Paulo (BR)

( * ) Notice: Subject to any disclaimer, the term of this patent is extended or adjusted under 35 U.S.C. 154(b) by 0 days.

(21) Appl. No.: 10/278,946

(22) Filed: Oct. 24, 2002

(65) Prior Publication Data

US 2003/0153733 A1 Aug. 14, 2003

Related U.S. Application Data

(62) Division of application No. 09/830,217, filed as application No. PCT/US99/06199 on Mar. 18, 1999, now Pat. No. 6,521,441.
(60) Provisional application No. 60/084,674, filed on May 7, 1998, provisional application No. 60/080,296, filed on Apr. 1, 1998, and provisional application No. 60/078,682, filed on Mar. 20, 1998.

(51) Int. Cl.[7] ............................. C12P 21/06; C12N 1/20; C12N 15/00; C07H 21/02
(52) U.S. Cl. ................ 435/69.1; 435/252.3; 435/320.1; 536/23.1
(58) Field of Search ............................. 435/69.1, 252.3, 435/320.1; 536/23.1

(56) References Cited

U.S. PATENT DOCUMENTS 6,593,114 B1 * 7/2003 Kunsch et al. ........... 435/91.41

\* cited by examiner

*Primary Examiner*—Mark Navarro
(74) *Attorney, Agent, or Firm*—Human Genome Sciences, Inc.

(57) ABSTRACT

The present invention relates to 11 novel genes from *S. aureus* and the polypeptides they encode. Also provided as are vectors, host cells, antibodies and recombinant methods for producing the same. The invention further relates to screening methods for identifying agonists and antagonists of *S. aureus* polypeptide activity. The invention additionally relates to diagnostic methods for detecting *Staphylococcus* nucleic acids, polypeptides and antibodies in a biological sample. The present invention further relates to novel vaccines for the prevention or attenuation of infection by *Staphylococcus*.

14 Claims, No Drawings

SEQUENCE LISTING

<160> NUMBER OF SEQ ID NOS: 22

<210> SEQ ID NO 1
<211> LENGTH: 1470
<212> TYPE: DNA
<213> ORGANISM: Staphylococcus aureus

<400> SEQUENCE: 1

```
tggaaaatta atgaagttcc aaagtttaga tcaaaactgg aataatggtg gatggcgtaa      60
agcagaggtt gcacataaag ttgttcataa ttatgaaaat gatatgattt ttattagacc     120
atttaaaaaa gcataattta aatcgaaggc aggacattga aatatgaaat tttcaacttt     180
aagtgaagaa gaatttacca actacaccaa aaagcacttc aaacattata cgcagtctat     240
agaattatat aattatagaa ataaaataaa tcatgaagca catattgtgg gagtgaagaa     300
tgataaaaat gaagttatag ctgcatgttt attaacagag gcacgaattt ttaaattcta     360
caaatatttc tactctcata gaggtccttt acttgattat ttcgatgcta aattagtttg     420
ttactttttt aaagaattat ctaaattcat ttataaaaat agaggagtat ttattcttgt     480
tgatccatat ttaatagaga atttaagaga tgcaaatggt aggataataa agaattataa     540
taattcagtg atagtaaaga tgctagggaa aattgggtat ctccatcaag gttatacaac     600
aggatattca aataaaagtc aaattaggtg gatttctgta ttggatttaa aagataaaga     660
```

```
tgagaatcaa cttttaaaag aaatggaata ccaaactaga agaaatataaa aaaagactat    720 tgagattggt gttaaggttg aagatttatc tattgaagaa acaaatcgat tttataaatt    780
gtttcaaatg gctgaagaaa acatggtttt tcatttcatg aatgaagatt attttaaacg    840
aatgcaagaa atatataaag ataaggcaat gttaaagata gcttgtataa atcttaatga    900
atatcaagat aaattaaaaa tacaattatt gaaaatcgaa aatgaaatga tgactgtgaa    960
cagagcatta aatgaaaatc caattctaa aaaaaataaa tcaaaattaa atcagttaaa   1020
tatgcaatta tctagtatta ataatagaat tagtaaaacc gaagaactaa tatttgaaga   1080
tggacctgtt ttggatttag ctgctgcttt atttatatgt actgatgatg aagtttatta   1140
tctatcaagt ggatcaaatc cgaaatataa tcagtatatg ggtgcatatc atctacaatg   1200
gcatatgata aaatatgcaa aatcacataa tattaatagg tataattttt atggaataac   1260
aggcgtcttt agtaatgagg cggatgattt tggtgttcaa caatttaaaa agggttttaa   1320
tgcacatgtt gaagaattaa ttggtgattt catcaaacca gtaagaccaa ttctatataa   1380
atttgcaaaa cttatttata aggtttaatt ataaagtatg ttggaaattg aaattttaaa   1440
ttctttccaa catactttc actttttaag                                     1470
```

<210> SEQ ID NO 2
<211> LENGTH: 414
<212> TYPE: PRT
<213> ORGANISM: Staphylococcus aureus

<400> SEQUENCE: 2

```
Met Lys Phe Ser Thr Leu Ser Glu Glu Phe Thr Asn Tyr Thr Lys
  1               5                  10                  15

Lys His Phe Lys His Tyr Thr Gln Ser Ile Glu Leu Tyr Asn Tyr Arg
                 20                  25                  30

Asn Lys Ile Asn His Glu Ala His Ile Val Gly Val Lys Asn Asp Lys
             35                  40                  45

Asn Glu Val Ile Ala Ala Cys Leu Leu Thr Glu Ala Arg Ile Phe Lys
         50                  55                  60

Phe Tyr Lys Tyr Phe Tyr Ser His Arg Gly Pro Leu Leu Asp Tyr Phe
 65                  70                  75                  80

Asp Ala Lys Leu Val Cys Tyr Phe Phe Lys Glu Leu Ser Lys Phe Ile
                 85                  90                  95

Tyr Lys Asn Arg Gly Val Phe Ile Leu Val Asp Pro Tyr Leu Ile Glu
            100                 105                 110

Asn Leu Arg Asp Ala Asn Gly Arg Ile Ile Lys Asn Tyr Asn Asn Ser
        115                 120                 125

Val Ile Val Lys Met Leu Gly Lys Ile Gly Tyr Leu His Gln Gly Tyr
    130                 135                 140

Thr Thr Gly Tyr Ser Asn Lys Ser Gln Ile Arg Trp Ile Ser Val Leu
145                 150                 155                 160

Asp Leu Lys Asp Lys Asp Glu Asn Gln Leu Leu Lys Glu Met Glu Tyr
                165                 170                 175

Gln Thr Arg Arg Asn Ile Lys Lys Thr Ile Glu Ile Gly Val Lys Val
            180                 185                 190

Glu Asp Leu Ser Ile Glu Glu Thr Asn Arg Phe Tyr Lys Leu Phe Gln
        195                 200                 205

Met Ala Glu Glu Lys His Gly Phe His Phe Met Asn Glu Asp Tyr Phe
    210                 215                 220
```

```
Lys Arg Met Gln Glu Ile Tyr Lys Asp Lys Ala Met Leu Lys Ile Ala
225                 230                 235                 240

Cys Ile Asn Leu Asn Glu Tyr Gln Asp Lys Leu Lys Ile Gln Leu Leu
            245                 250                 255

Lys Ile Glu Asn Glu Met Met Thr Val Asn Arg Ala Leu Asn Glu Asn
        260                 265                 270

Pro Asn Ser Lys Lys Asn Lys Ser Lys Leu Asn Gln Leu Asn Met Gln
    275                 280                 285

Leu Ser Ser Ile Asn Asn Arg Ile Ser Lys Thr Glu Glu Leu Ile Phe
290                 295                 300

Glu Asp Gly Pro Val Leu Asp Leu Ala Ala Ala Leu Phe Ile Cys Thr
305                 310                 315                 320

Asp Asp Glu Val Tyr Tyr Leu Ser Ser Gly Ser Asn Pro Lys Tyr Asn
                325                 330                 335

Gln Tyr Met Gly Ala Tyr His Leu Gln Trp His Met Ile Lys Tyr Ala
            340                 345                 350

Lys Ser His Asn Ile Asn Arg Tyr Asn Phe Tyr Gly Ile Thr Gly Val
        355                 360                 365

Phe Ser Asn Glu Ala Asp Asp Phe Gly Val Gln Gln Phe Lys Lys Gly
370                 375                 380

Phe Asn Ala His Val Glu Glu Leu Ile Gly Asp Phe Ile Lys Pro Val
385                 390                 395                 400

Arg Pro Ile Leu Tyr Lys Phe Ala Lys Leu Ile Tyr Lys Val
                405                 410

<210> SEQ ID NO 3
<211> LENGTH: 561
<212> TYPE: DNA
<213> ORGANISM: Staphylococcus aureus

<400> SEQUENCE: 3
tctccgggtg gtgtaattgt agttctactt gttattttac ttatgattac aatggcttat      60
cagaaaatgc gaatgaagtt taaaaaggga gctaatatca atgaatacaa atgatgctat     120
taaaatttta aaagagaacg gtttaaaata tacagataaa cgtaaagata tgttagatat     180
ttttgtcgaa gaagataagt atataaacgc aaagtatata caacaagtta tggatgaaaa     240
ttatcctgga atttcattcg acacaatata tagaaacctg cacttatttta aagatttagg     300 aattattgaa atacagaaac ttgatggtga aatgaagttt agaatcgctt gtacaaacca     360
tcatcatcat cattttatct gtgaaaagtg tggagataca aagtaatag attattgtcc     420 aatagatcag ataaaattat cactacctgg tgttaatatt cacaaacaca aacttgaagt     480
ttatggtgta tgtgagtctt gccaagatta atataaagaa atgagattta tgcacatttg     540
gtccgatgta tgcataaatc t                                                561

<210> SEQ ID NO 4
<211> LENGTH: 136
<212> TYPE: PRT
<213> ORGANISM: Staphylococcus aureus

<400> SEQUENCE: 4

Met Asn Thr Asn Asp Ala Ile Lys Ile Leu Lys Glu Asn Gly Leu Lys
1               5                   10                  15

Tyr Thr Asp Lys Arg Lys Asp Met Leu Asp Ile Phe Val Glu Glu Asp
            20                  25                  30

Lys Tyr Ile Asn Ala Lys Tyr Ile Gln Gln Val Met Asp Glu Asn Tyr
```

```
                35                  40                  45
Pro Gly Ile Ser Phe Asp Thr Ile Tyr Arg Asn Leu His Leu Phe Lys
    50                  55                  60

Asp Leu Gly Ile Ile Glu Asn Thr Glu Leu Asp Gly Glu Met Lys Phe
 65                  70                  75                  80

Arg Ile Ala Cys Thr Asn His His His His Phe Ile Cys Glu Lys
                85                  90                  95

Cys Gly Asp Thr Lys Val Ile Asp Tyr Cys Pro Ile Asp Gln Ile Lys
            100                 105                 110

Leu Ser Leu Pro Gly Val Asn Ile His Lys His Lys Leu Glu Val Tyr
        115                 120                 125

Gly Val Cys Glu Ser Cys Gln Asp
    130                 135

<210> SEQ ID NO 5
<211> LENGTH: 586
<212> TYPE: DNA
<213> ORGANISM: Staphylococcus aureus

<400> SEQUENCE: 5
ttaaatgaaa tcatcatgta aatattgaca cgcgcgcaat actacagtta tatttatagt      60
aagtaataat aattattata taagaaagat ggtgatatag atgagtgttg aaatagaatc     120
aattgaacat gaactagaag aatcaattgc atcattgcga caagcaggcg taagaattac     180
acctcaaaga caagcaatat tacgttattt aatttcttca catactcatc caacagctga     240
tgaaatttat caagcacttt cacctgattt tccaaatata agtgttgcga caatatataa     300
taacttaaga gtgtttaaag atattggaat tgtaaaagaa ttaacatatg gagactcatc     360
aagtcgattc gactttaata cacataatca ttatcatatt atatgtgaac aatgtggtaa     420
gattgttgat tttcaatatc cacagttaaa tgaaattgaa agattagctc agcatatgac     480
tgactttgac gtaacacatc atcgaatgga aatttatgga gtttgtaaag aatgccaaga     540
taaataattt aactttggta gtatgacaaa ttaaaaaagc gttact                    586

<210> SEQ ID NO 6
<211> LENGTH: 148
<212> TYPE: PRT
<213> ORGANISM: Staphylococcus aureus

<400> SEQUENCE: 6

Met Ser Val Glu Ile Glu Ser Ile Glu His Glu Leu Glu Glu Ser Ile
  1               5                  10                  15

Ala Ser Leu Arg Gln Ala Gly Val Arg Ile Thr Pro Gln Arg Gln Ala
                 20                  25                  30

Ile Leu Arg Tyr Leu Ile Ser Ser His Thr His Pro Thr Ala Asp Glu
            35                  40                  45

Ile Tyr Gln Ala Leu Ser Pro Asp Phe Pro Asn Ile Ser Val Ala Thr
        50                  55                  60

Ile Tyr Asn Asn Leu Arg Val Phe Lys Asp Ile Gly Ile Val Lys Glu
 65                  70                  75                  80

Leu Thr Tyr Gly Asp Ser Ser Ser Arg Phe Asp Phe Asn Thr His Asn
                 85                  90                  95

His Tyr His Ile Ile Cys Glu Gln Cys Gly Lys Ile Val Asp Phe Gln
            100                 105                 110

Tyr Pro Gln Leu Asn Glu Ile Glu Arg Leu Ala Gln His Met Thr Asp
        115                 120                 125
```

Phe Asp Val Thr His His Arg Met Glu Ile Tyr Gly Val Cys Lys Glu
        130                 135                 140

Cys Gln Asp Lys
145

<210> SEQ ID NO 7
<211> LENGTH: 600
<212> TYPE: DNA
<213> ORGANISM: Staphylococcus aureus

<400> SEQUENCE: 7
tgagaaaagc ttgcatttta ttgagaaaac tgttagtttt aattgtaaag tttgaaataa      60
tttgtaatga ttttaattat tagtagggga gtggacatcg ttggaagaac gattaaatcg     120
cgttaagcaa caattacaac aatcatcata taagctaacg ccacaacgcg aagctactgt     180
tagagttcta attgaaaatg aaaagatca tctaagtgct gaagacgtat atctgaaagt      240
aaaagataaa gcgcctgaaa ttggcttggc gacagtatac agaacgttag agttgttagc     300
tgaactaaaa gttgtcgaca aaattaactt tggtgatggc gtcgctcgtt ttgatttaag     360
aaaagaaggc gcaaaacatt tccaccatca tttagtatgt atggaatgtg gtcgtgtaga     420
tgaaatcgat gaagatttgt taccagaagt tgaaaatcga gttgaaaatg agttcaattt     480
taaaatttta gatcatcgtt taactttcca tggtgtgtgt gaaacgtgcc aagctaaagg     540
taaaggatag taaattgcgt aggttaaatt aaccttcgct ttttttagag gtgtggttat     600

<210> SEQ ID NO 8
<211> LENGTH: 149
<212> TYPE: PRT
<213> ORGANISM: Staphylococcus aureus

<400> SEQUENCE: 8

Leu Glu Glu Arg Leu Asn Arg Val Lys Gln Gln Leu Gln Gln Ser Ser
  1               5                  10                  15

Tyr Lys Leu Thr Pro Gln Arg Glu Ala Thr Val Arg Val Leu Ile Glu
                 20                  25                  30

Asn Glu Lys Asp His Leu Ser Ala Glu Asp Val Tyr Leu Lys Val Lys
             35                  40                  45

Asp Lys Ala Pro Glu Ile Gly Leu Ala Thr Val Tyr Arg Thr Leu Glu
         50                  55                  60

Leu Leu Ala Glu Leu Lys Val Val Asp Lys Ile Asn Phe Gly Asp Gly
 65                  70                  75                  80

Val Ala Arg Phe Asp Leu Arg Lys Glu Gly Ala Lys His Phe His His
                 85                  90                  95

His Leu Val Cys Met Glu Cys Gly Arg Val Asp Glu Ile Asp Glu Asp
                100                 105                 110

Leu Leu Pro Glu Val Glu Asn Arg Val Glu Asn Glu Phe Asn Phe Lys
            115                 120                 125

Ile Leu Asp His Arg Leu Thr Phe His Gly Val Cys Glu Thr Cys Gln
        130                 135                 140

Ala Lys Gly Lys Gly
145

<210> SEQ ID NO 9
<211> LENGTH: 1647
<212> TYPE: DNA
<213> ORGANISM: Staphylococcus aureus -continued

```
<400> SEQUENCE: 9
gtaaatatac ctctttaatt aatttattca atagaactgg tataataaaa taaatctcat      60
taggcactta agtaaattta acatataaaa aggaacgttt atgactacta aaaaactgta     120
ttttctatcc atttctatta tcattttagt cgccatttca attgctatat atataacatt     180
aaatagcaat acgaagacac ggttaaccaa tgattcgcaa caacaaatag atacaattat     240
cgagcatgat ttacaaaagg gacacattcc tggagcatca attttaatag taaaaaatgg     300
caaagttttt ttaaataaag gttatggtta tcaagatgtt gataaaaaag tcaaagcttc     360
tcccacaaca aagtatgaaa ttgcttctaa tacgaaagct ttcacaggtc ttgcaatttt     420
aaaattagct caagaaggtc gattaaactt aaatgatgcc gtatccaaac atgtgcctca     480
ttttaaaatg aactataatg gtcaaaatga actattacg attaagcaac ttttggctca     540
aacaagtggt atacctagtg atattacaag cgaagattct gtgacaagca aaaataatcg     600
tttaaatgat gtaacccatg caattatggg tgatgaatta catcataagc ccggagaaga     660
atttgaatac tcaaatatga actatgattt attaggttta attatccaaa acgttacgaa     720
gcaatcctat acaaaatata ttacaaattc atggctcaag cctttgcata tgacacatac     780
atcattcaaa caaaccaatt acaaatcaaa acatgatgct attggctatg aattacaagg     840
ttcgacacct gtcgtctcta aacctgaatt taacctttgg gatacaccat cagcatatat     900
gatgacatca actgaagatt tggaacattg gataaaattc caacttaatc cacctgataa     960
atacaaatca ttagttcaac aatcacataa aaatttatct tcaacaattg gtgaacctaa    1020
tgccaatgca tatgcttccg gctggtttac caataatgat gaacatttag tgtttcattc    1080
aggaacgcta gataactttt catcatttat tttactaaat ccaaaacaaa attatggaat    1140
tgttgtactt gcaaatctaa attcggaata tgtacccaaa ttagttgagc atcttaatac    1200
acaaattgta aatcacaagc gatattcgac ggttgcgtct atgctcaatc aatataaaga    1260
tcaatttaat attgttaccg ttttgatgac aacacttatt ttattagcat ttatattctc    1320
agcttatcgt gcttggcaaa tgcgccatgg tcaaattctt ttgcgtagat caaaacggat    1380
tgctgtattg agttggttat cattatgtat atgtatcgct ttagcgctca tattatatgc    1440
attaccatat ctcattctcg gtagcaataa ttggtctttt gtactgactt ggctaccaat    1500
agaaattaaa ttagcactaa tcacaacatt aattgcatta ttcagtacat taattgtaat    1560
tctgttattc cttcatacaa agataacgaa gacataataa aaaagacttg ttcgagccgt    1620
gcgtttgata atatatcatc cacgatt                                        1647
```

```
<210> SEQ ID NO 10
<211> LENGTH: 498
<212> TYPE: PRT
<213> ORGANISM: Staphylococcus aureus

<400> SEQUENCE: 10
```

```
Met Thr Thr Lys Lys Leu Tyr Phe Leu Ser Ile Ser Ile Ile Ile Leu
 1               5                  10                  15

Val Ala Ile Ser Ile Ala Ile Tyr Ile Thr Leu Asn Ser Asn Thr Lys
            20                  25                  30

Thr Arg Leu Thr Asn Asp Ser Gln Gln Gln Ile Asp Thr Ile Ile Glu
        35                  40                  45

His Asp Leu Gln Lys Gly His Ile Pro Gly Ala Ser Ile Leu Ile Val
    50                  55                  60

Lys Asn Gly Lys Val Phe Leu Asn Lys Gly Tyr Gly Tyr Gln Asp Val
```

```
           65                  70                  75                  80
Asp Lys Lys Val Lys Ala Ser Pro Thr Thr Lys Tyr Glu Ile Ala Ser
                        85                  90                  95
Asn Thr Lys Ala Phe Thr Gly Leu Ala Ile Leu Lys Leu Ala Gln Glu
                100                 105                 110
Gly Arg Leu Asn Leu Asn Asp Ala Val Ser Lys His Val Pro His Phe
            115                 120                 125
Lys Met Asn Tyr Asn Gly Gln Asn Glu Thr Ile Thr Ile Lys Gln Leu
        130                 135                 140
Leu Ala Gln Thr Ser Gly Ile Pro Ser Asp Ile Thr Ser Glu Asp Ser
145                 150                 155                 160
Val Thr Ser Lys Asn Asn Arg Leu Asn Asp Val Thr His Ala Ile Met
                165                 170                 175
Gly Asp Glu Leu His His Lys Pro Gly Glu Glu Phe Glu Tyr Ser Asn
                180                 185                 190
Met Asn Tyr Asp Leu Leu Gly Leu Ile Ile Gln Asn Val Thr Lys Gln
            195                 200                 205
Ser Tyr Thr Lys Tyr Ile Thr Asn Ser Trp Leu Lys Pro Leu His Met
        210                 215                 220
Thr His Thr Ser Phe Lys Gln Thr Asn Tyr Lys Ser Lys His Asp Ala
225                 230                 235                 240
Ile Gly Tyr Glu Leu Gln Gly Ser Thr Pro Val Val Ser Lys Pro Glu
                245                 250                 255
Phe Asn Leu Trp Asp Thr Pro Ser Ala Tyr Met Met Thr Ser Thr Glu
                260                 265                 270
Asp Leu Glu His Trp Ile Lys Phe Gln Leu Asn Pro Pro Asp Lys Tyr
            275                 280                 285
Lys Ser Leu Val Gln Gln Ser His Lys Asn Leu Ser Ser Thr Ile Gly
        290                 295                 300
Glu Pro Asn Ala Asn Ala Tyr Ala Ser Gly Trp Phe Thr Asn Asn Asp
305                 310                 315                 320
Glu His Leu Val Phe His Ser Gly Thr Leu Asp Asn Phe Ser Ser Phe
                325                 330                 335
Ile Leu Leu Asn Pro Lys Gln Asn Tyr Gly Ile Val Val Leu Ala Asn
                340                 345                 350
Leu Asn Ser Glu Tyr Val Pro Lys Leu Val Glu His Leu Asn Thr Gln
            355                 360                 365
Ile Val Asn His Lys Arg Tyr Ser Thr Val Ala Ser Met Leu Asn Gln
        370                 375                 380
Tyr Lys Asp Gln Phe Asn Ile Val Thr Val Leu Met Thr Thr Leu Ile
385                 390                 395                 400
Leu Leu Ala Phe Ile Phe Ser Ala Tyr Arg Ala Trp Gln Met Arg His
                405                 410                 415
Gly Gln Ile Leu Leu Arg Arg Ser Lys Arg Ile Ala Val Leu Ser Trp
            420                 425                 430
Leu Ser Leu Cys Ile Cys Ile Ala Leu Ala Leu Ile Leu Tyr Ala Leu
        435                 440                 445
Pro Tyr Leu Ile Leu Gly Ser Asn Asn Trp Ser Phe Val Leu Thr Trp
        450                 455                 460
Leu Pro Ile Glu Ile Lys Leu Ala Leu Ile Thr Thr Leu Ile Ala Leu
465                 470                 475                 480
Phe Ser Thr Leu Ile Val Ile Leu Leu Phe Leu His Thr Lys Ile Thr
                485                 490                 495
```

Lys Thr

<210> SEQ ID NO 11
<211> LENGTH: 2226
<212> TYPE: DNA
<213> ORGANISM: Staphylococcus aureus

<400> SEQUENCE: 11

| | | | | | |
|---|---|---|---|---|---|
| ctcttaaatg | agaccgttat | tttttgtca | aaagataga | aataatttct | aaattcatat | 60 |
| atgatttaaa | gtgaaagact | tgaatagag | gtaggtagtt | ttgttaaaaa | gactaaaaga | 120 |
| aaaatcaaat | gatgaaatcg | ttcaaaatac | cattaacaag | agaattaact | ttatatttgg | 180 |
| tgtgattgta | tttatttttg | cagtactagt | actacgttta | ggttatttac | aaatcgcaca | 240 |
| aggctcacat | tataaacaaa | ttataaaaaa | tgatgaaaac | attacagtga | atgagtctgt | 300 |
| gccaagaggt | cgtatttag | acagaaatgg | gaaagttta | gttgataatg | cttctaaaat | 360 |
| ggctattaca | tatactaggg | gtcgaaaaac | aacacaatcg | gaaatgttgg | atacggctga | 420 |
| aaagttatca | agctaatca | agatggatac | taagaaaatt | acagaacgtg | ataagaaaga | 480 |
| tttctggatt | cagttgcatc | ctaaaaaagc | aaaagcaatg | atgacaaaag | aacaagctat | 540 |
| gttagcagat | ggaagtatta | aacaagatca | atatgataaa | caactgttat | cgaaaatcgg | 600 |
| aaaatcacaa | ttagatgaat | tgtcttctaa | agatttacaa | gttttagcta | tttttcgaga | 660 |
| gatgaatgca | ggaacagttt | tagatccaca | aatgataaaa | aatgaagatg | tcagtgaaaa | 720 |
| agagtatgca | gcagtttctc | agcaactttc | caaattacca | ggtgttaaca | cgtctatgga | 780 |
| ttgggataga | aaatatccat | atggcgatac | tttaagaggt | atattcggag | atgtatcgac | 840 |
| acctgctgaa | ggtattccaa | agaattgac | agaacattac | ttatccaaag | gatattcacg | 900 |
| caatgatcgt | gttggaaaat | cttacctaga | atatcaatat | gaagatgtat | tgcgtggtaa | 960 |
| gaagaaagaa | atgaaataca | caacggacaa | atctggtaaa | gttacatctt | cagaagtgtt | 1020 |
| aaatcctggc | gctcgcggtc | aagatttgaa | attaacgatc | gatatagatc | ttcaaaaaga | 1080 |
| agtagaagca | ttattagata | aacaaattaa | gaagcttcgc | agtcaaggtg | ccaaagatat | 1140 |
| ggataatgca | atgatggttg | tacaaaatcc | taaaaatgga | gacattcttg | cgcttgccgg | 1200 |
| aaagcagatt | aataagagtg | gtaaaatgac | tgattatgac | attggtacgt | ttacttctca | 1260 |
| atttgcggtt | ggatcttctg | taaaaggtgg | aacattatta | gccggttatc | agaataaagc | 1320 |
| tatcaaagtt | ggagaaacaa | tggtcgatga | accattacat | ttccaaggtg | gtttgacaaa | 1380 |
| acgatcatac | ttcaataaaa | acgggcatgt | aactattaat | gataagcaag | ctttgatgca | 1440 |
| ttcatcaaac | gtatatatgt | ttaaaacagc | attaaaatta | gcgggagacc | cttattattc | 1500 |
| tggtatggct | ttaccttcag | acataagttc | acctgcccaa | aagctaagaa | gaggattaaa | 1560 |
| tcaagtaggc | ttaggtgtga | aaacagggat | agatttacca | aatgaaacaa | gaggtcaaat | 1620 |
| cgaaccatta | acaaataatc | caggtaatta | tctagattta | tcaattggtc | aatatgatac | 1680 |
| ctatacacca | ttacaattat | cacaatatgt | ttcaactata | gcgaatgatg | gttatagaat | 1740 |
| acagccacac | attggattaa | cgattcatga | atcaactaat | aaagatgagg | ttggtccact | 1800 |
| caagaagaaa | attaatggca | ctgtcttgaa | caaggttaat | aatactgaaa | aggaaatcaa | 1860 |
| acaaattcaa | gaaggattca | aaatggcatt | taatgataaa | gatggtactg | gatatgttag | 1920 |
| ttttaaagat | acagtagtac | ctactgctgg | taaaacgggt | accgcagaag | tgttccaaaa | 1980 |
| cggagagcca | agagttaact | ctacttatat | aggatacgcg | ccaattgatg | atccaaaatt | 2040 |

```
agcgttttca attgtatata caaatcagcc tgtaccacca ccatggttaa caggtggaga    2100
cttaggtaga gatgtaatta actactactt taagcagtta ggtaaagatg ataaaaataa    2160
agacaaagac aaataaaatt taacctgacg attgtgtagc gcatggttgt aaaattttaa    2220
ctttgc                                                               2226
```

<210> SEQ ID NO 12
<211> LENGTH: 691
<212> TYPE: PRT
<213> ORGANISM: Staphylococcus aureus

<400> SEQUENCE: 12

```
Leu Leu Lys Arg Leu Lys Glu Lys Ser Asn Asp Glu Ile Val Gln Asn
  1               5                  10                  15

Thr Ile Asn Lys Arg Ile Asn Phe Phe Gly Val Ile Val Phe Ile
             20                  25                  30

Phe Ala Val Leu Val Leu Arg Leu Gly Tyr Leu Gln Ile Ala Gln Gly
         35                  40                  45

Ser His Tyr Lys Gln Ile Ile Lys Asn Asp Glu Asn Ile Thr Val Asn
     50                  55                  60

Glu Ser Val Pro Arg Gly Arg Ile Leu Asp Arg Asn Gly Lys Val Leu
 65                  70                  75                  80

Val Asp Asn Ala Ser Lys Met Ala Ile Thr Tyr Thr Arg Gly Arg Lys
                 85                  90                  95

Thr Thr Gln Ser Glu Met Leu Asp Thr Ala Glu Lys Leu Ser Lys Leu
            100                 105                 110

Ile Lys Met Asp Thr Lys Lys Ile Thr Glu Arg Asp Lys Lys Asp Phe
        115                 120                 125

Trp Ile Gln Leu His Pro Lys Lys Ala Lys Ala Met Met Thr Lys Glu
    130                 135                 140

Gln Ala Met Leu Ala Asp Gly Ser Ile Lys Gln Asp Gln Tyr Asp Lys
145                 150                 155                 160

Gln Leu Leu Ser Lys Ile Gly Lys Ser Gln Leu Asp Glu Leu Ser Ser
                165                 170                 175

Lys Asp Leu Gln Val Leu Ala Ile Phe Arg Glu Met Asn Ala Gly Thr
            180                 185                 190

Val Leu Asp Pro Gln Met Ile Lys Asn Glu Asp Val Ser Glu Lys Glu
        195                 200                 205

Tyr Ala Ala Val Ser Gln Gln Leu Ser Lys Leu Pro Gly Val Asn Thr
    210                 215                 220

Ser Met Asp Trp Asp Arg Lys Tyr Pro Tyr Gly Asp Thr Leu Arg Gly
225                 230                 235                 240

Ile Phe Gly Asp Val Ser Thr Pro Ala Glu Gly Ile Pro Lys Glu Leu
                245                 250                 255

Thr Glu His Tyr Leu Ser Lys Gly Tyr Ser Arg Asn Asp Arg Val Gly
            260                 265                 270

Lys Ser Tyr Leu Glu Tyr Gln Tyr Glu Asp Val Leu Arg Gly Lys Lys
        275                 280                 285

Lys Glu Met Lys Tyr Thr Thr Asp Lys Ser Gly Lys Val Thr Ser Ser
    290                 295                 300

Glu Val Leu Asn Pro Gly Ala Arg Gly Gln Asp Leu Lys Leu Thr Ile
305                 310                 315                 320

Asp Ile Asp Leu Gln Lys Glu Val Glu Ala Leu Leu Asp Lys Gln Ile
                325                 330                 335
```

-continued

```
Lys Lys Leu Arg Ser Gln Gly Ala Lys Asp Met Asp Asn Ala Met Met
            340                 345                 350
Val Val Gln Asn Pro Lys Asn Gly Asp Ile Leu Ala Leu Ala Gly Lys
        355                 360                 365
Gln Ile Asn Lys Ser Gly Lys Met Thr Asp Tyr Asp Ile Gly Thr Phe
370                 375                 380
Thr Ser Gln Phe Ala Val Gly Ser Ser Val Lys Gly Gly Thr Leu Leu
385                 390                 395                 400
Ala Gly Tyr Gln Asn Lys Ala Ile Lys Val Gly Glu Thr Met Val Asp
            405                 410                 415
Glu Pro Leu His Phe Gln Gly Gly Leu Thr Lys Arg Ser Tyr Phe Asn
        420                 425                 430
Lys Asn Gly His Val Thr Ile Asn Asp Lys Gln Ala Leu Met His Ser
            435                 440                 445
Ser Asn Val Tyr Met Phe Lys Thr Ala Leu Lys Leu Ala Gly Asp Pro
450                 455                 460
Tyr Tyr Ser Gly Met Ala Leu Pro Ser Asp Ile Ser Ser Pro Ala Gln
465                 470                 475                 480
Lys Leu Arg Arg Gly Leu Asn Gln Val Gly Leu Gly Val Lys Thr Gly
            485                 490                 495
Ile Asp Leu Pro Asn Glu Thr Arg Gly Gln Ile Glu Pro Leu Thr Asn
        500                 505                 510
Asn Pro Gly Asn Tyr Leu Asp Leu Ser Ile Gly Gln Tyr Asp Thr Tyr
            515                 520                 525
Thr Pro Leu Gln Leu Ser Gln Tyr Val Ser Thr Ile Ala Asn Asp Gly
        530                 535                 540
Tyr Arg Ile Gln Pro His Ile Gly Leu Thr Ile His Glu Ser Thr Asn
545                 550                 555                 560
Lys Asp Glu Val Gly Pro Leu Lys Lys Ile Asn Gly Thr Val Leu
            565                 570                 575
Asn Lys Val Asn Asn Thr Glu Lys Glu Ile Lys Gln Ile Gln Glu Gly
        580                 585                 590
Phe Lys Met Ala Phe Asn Asp Lys Asp Gly Thr Gly Tyr Val Ser Phe
            595                 600                 605
Lys Asp Thr Val Pro Thr Ala Gly Lys Thr Gly Thr Ala Glu Val
        610                 615                 620
Phe Gln Asn Gly Glu Pro Arg Val Asn Ser Thr Tyr Ile Gly Tyr Ala
625                 630                 635                 640
Pro Ile Asp Asp Pro Lys Leu Ala Phe Ser Ile Val Tyr Thr Asn Gln
            645                 650                 655
Pro Val Pro Pro Pro Trp Leu Thr Gly Gly Asp Leu Gly Arg Asp Val
        660                 665                 670
Ile Asn Tyr Tyr Phe Lys Gln Leu Gly Lys Asp Asp Lys Asn Lys Asp
            675                 680                 685
Lys Asp Lys
        690
```

<210> SEQ ID NO 13
<211> LENGTH: 1056
<212> TYPE: DNA
<213> ORGANISM: Staphylococcus aureus

<400> SEQUENCE: 13

```
tcctattcct tatgcatttc ccctaattat aattaacgtt aaaataaaag tcaaattgcc    60
```

```
ttaaatatgg tatactataa cgtaatttag gaggttaaag atgacgaatc aagacaacaa      120
tcatcaattg aatcatcgta tatatcattt tgaaaagata tataaagcta tcaaacatgt      180
cattgtttac atatttatga ttttcattgc catcgttgct atcgctgtga ttgcgatgtc      240
tttatatttt catcatttaa ctaaaacgtc cgactcatta tcagatgatg ctttaataaa      300
aaaagttcga caaatacctg gcgatgaatt attagatcat aataacaaaa atttattata      360
tgagtataac cattctcaaa actcactcat tataggccct aaaacatcaa gtccaaatgt      420
cattaaagca ttaacgtcat ctgaagacac tttattttat aaacatgatg catcttacc      480 aaaggcgatt ttaagagcaa tgatacaaga tatttttaat actgatcaaa gttcaggtgg      540
tagcacaatt acacaacaac ttgttaaaaa tcaagttctt accaacgaaa aacatatag      600 tagaaaagca aatgaacttc gcctagcaat tagattagaa cacctactct caaaagatga      660
aattatatat acatatttaa atatagttcc cttcggtaga gattataatg gcgctaatat      720
ttccggaatt gcatccgctt catatagtct atttggtatt ccaccaaaag atttatcaat      780
tgcacaatct gcatacctta tcggtttgtt gcaaagccca tatggctata caccctacga      840
aaaagatgga acgttaaaat cggataaaga tttgaaatat agtattcaaa gacaacatta      900
tgtattaaag cgtatgttaa tcgaagatca aatcactgaa aaagaataca acgacgcatt      960
aaaatatgat attaaatcac atttgttaaa tcgaaaaaag cgttaattga tgctcacttt     1020
ttaaagtaac cacaacaatg aatccaaata ttaaaa                              1056

<210> SEQ ID NO 14
<211> LENGTH: 301
<212> TYPE: PRT
<213> ORGANISM: Staphylococcus aureus

<400> SEQUENCE: 14

Met Thr Asn Gln Asp Asn Asn His Gln Leu Asn His Arg Ile Tyr His
  1               5                  10                  15

Phe Glu Lys Ile Tyr Lys Ala Ile Lys His Val Ile Val Tyr Ile Phe
             20                  25                  30

Met Ile Phe Ile Ala Ile Val Ala Ile Ala Val Ile Ala Met Ser Leu
         35                  40                  45

Tyr Phe His His Leu Thr Lys Thr Ser Asp Ser Leu Ser Asp Asp Ala
     50                  55                  60

Leu Ile Lys Lys Val Arg Gln Ile Pro Gly Asp Glu Leu Leu Asp His
 65                  70                  75                  80

Asn Asn Lys Asn Leu Leu Tyr Glu Tyr Asn His Ser Gln Asn Ser Leu
                 85                  90                  95

Ile Ile Gly Pro Lys Thr Ser Pro Asn Val Ile Lys Ala Leu Thr
            100                 105                 110

Ser Ser Glu Asp Thr Leu Phe Tyr Lys His Asp Gly Ile Leu Pro Lys
        115                 120                 125

Ala Ile Leu Arg Ala Met Ile Gln Asp Ile Phe Asn Thr Asp Gln Ser
    130                 135                 140

Ser Gly Gly Ser Thr Ile Thr Gln Gln Leu Val Lys Asn Gln Val Leu
145                 150                 155                 160

Thr Asn Glu Lys Thr Tyr Ser Arg Lys Ala Asn Glu Leu Arg Leu Ala
                165                 170                 175

Ile Arg Leu Glu His Leu Leu Ser Lys Asp Glu Ile Ile Tyr Thr Tyr
            180                 185                 190

Leu Asn Ile Val Pro Phe Gly Arg Asp Tyr Asn Gly Ala Asn Ile Ser
```

```
                   195                 200                  205
Gly Ile Ala Ser Ala Ser Tyr Ser Leu Phe Gly Ile Pro Pro Lys Asp
    210                 215                 220

Leu Ser Ile Ala Gln Ser Ala Tyr Leu Ile Gly Leu Leu Gln Ser Pro
225                 230                 235                 240

Tyr Gly Tyr Thr Pro Tyr Glu Lys Asp Gly Thr Leu Lys Ser Asp Lys
                245                 250                 255

Asp Leu Lys Tyr Ser Ile Gln Arg Gln His Tyr Val Leu Lys Arg Met
            260                 265                 270

Leu Ile Glu Asp Gln Ile Thr Glu Lys Glu Tyr Asn Asp Ala Leu Lys
        275                 280                 285

Tyr Asp Ile Lys Ser His Leu Leu Asn Arg Lys Lys Arg
    290                 295                 300
```

<210> SEQ ID NO 15
<211> LENGTH: 999
<212> TYPE: DNA
<213> ORGANISM: Staphylococcus aureus

<400> SEQUENCE: 15

```
tagtcaatga ataaagtaat taaaatgctt gttgttacgc ttgctttcct acttgtttta      60
gcaggatgta gtgggaattc aaataaacaa tcatctgata caaagataa  ggaaacaact     120
tcaattaaac atgcaatggg tacaactgaa attaaaggga accaaagcg  tgttgttacg     180
ctatatcaag gtgccactga cgtcgctgta tctttaggtg ttaaacctgt aggtgctgta     240
gaatcatgga cacaaaaacc gaaattcgaa tacataaaaa atgatttaaa agatactaag     300
attgtaggtc aagaacctgc acctaactta gaggaaatct ctaaattaaa accggactta     360
attgtcgcgt caaaagttag aaatgaaaaa gtttacgatc aattatctaa aatcgcacca     420
acagtttcta ctgatacagt tttcaaattc aaagatacaa ctaagttaat gggggaaagct    480
ttagggaaag aaaaagaagc tgaagattta cttaaaaagt acgatgataa agtagctgca     540
ttccaaaaag atgcaaaagc aaagtataaa gatgcatggc cattgaaagc ttcagttgtt     600
aacttccgtg ctgatcatac aagaatttat gctggtggat atgctggtga atcttaaat     660
gatttaggat tcaaacgtaa taagactta  caaaaacaag ttgataatgg taaagatatt    720
atccaactta catctaaaga aagcattcca ttaatgaacg ctgatcatat ttttgtagta     780
aaatcagatc caaatgcgaa agatgctgca ttagttaaaa agactgaaag cgaatggact     840
tcaagtaaag agtggaaaaa tttagacgca gttaaaaaca accaagtatc tgatgattta     900
gatgaaatca cttggaactt agctggcgga tataatctt  cattaaaact tattgacgat     960
ttatatgaaa agttaaatat tgaaaaacaa tcaaaataa                            999
```

<210> SEQ ID NO 16
<211> LENGTH: 330
<212> TYPE: PRT
<213> ORGANISM: Staphylococcus aureus

<400> SEQUENCE: 16

```
Met Asn Lys Val Ile Lys Met Leu Val Val Thr Leu Ala Phe Leu Leu
  1               5                  10                  15

Val Leu Ala Gly Cys Ser Gly Asn Ser Asn Lys Gln Ser Ser Asp Asn
                20                  25                  30

Lys Asp Lys Glu Thr Thr Ser Ile Lys His Ala Met Gly Thr Thr Glu
            35                  40                  45
```

```
Ile Lys Gly Lys Pro Lys Arg Val Val Thr Leu Tyr Gln Gly Ala Thr
 50                  55                  60

Asp Val Ala Val Ser Leu Gly Val Lys Pro Val Gly Ala Val Glu Ser
 65                  70                  75                  80

Trp Thr Gln Lys Pro Lys Phe Glu Tyr Ile Lys Asn Asp Leu Lys Asp
                 85                  90                  95

Thr Lys Ile Val Gly Gln Glu Pro Ala Pro Asn Leu Glu Glu Ile Ser
                100                 105                 110

Lys Leu Lys Pro Asp Leu Ile Val Ala Ser Lys Val Arg Asn Glu Lys
            115                 120                 125

Val Tyr Asp Gln Leu Ser Lys Ile Ala Pro Thr Val Ser Thr Asp Thr
130                 135                 140

Val Phe Lys Phe Lys Asp Thr Thr Lys Leu Met Gly Lys Ala Leu Gly
145                 150                 155                 160

Lys Glu Lys Glu Ala Glu Asp Leu Leu Lys Lys Tyr Asp Asp Lys Val
                165                 170                 175

Ala Ala Phe Gln Lys Asp Ala Lys Ala Lys Tyr Lys Asp Ala Trp Pro
                180                 185                 190

Leu Lys Ala Ser Val Val Asn Phe Arg Ala Asp His Thr Arg Ile Tyr
            195                 200                 205

Ala Gly Gly Tyr Ala Gly Glu Ile Leu Asn Asp Leu Gly Phe Lys Arg
210                 215                 220

Asn Lys Asp Leu Gln Lys Gln Val Asp Asn Gly Lys Asp Ile Ile Gln
225                 230                 235                 240

Leu Thr Ser Lys Glu Ser Ile Pro Leu Met Asn Ala Asp His Ile Phe
                245                 250                 255

Val Val Lys Ser Asp Pro Asn Ala Lys Asp Ala Ala Leu Val Lys Lys
                260                 265                 270

Thr Glu Ser Glu Trp Thr Ser Ser Lys Glu Trp Lys Asn Leu Asp Ala
            275                 280                 285

Val Lys Asn Asn Gln Val Ser Asp Asp Leu Asp Glu Ile Thr Trp Asn
290                 295                 300

Leu Ala Gly Gly Tyr Lys Ser Ser Leu Lys Leu Ile Asp Asp Leu Tyr
305                 310                 315                 320

Glu Lys Leu Asn Ile Glu Lys Gln Ser Lys
                325                 330

<210> SEQ ID NO 17
<211> LENGTH: 1014
<212> TYPE: DNA
<213> ORGANISM: Staphylococcus aureus

<400> SEQUENCE: 17
taattaagga gttttacgat gctacttaaa ccaaaatacc aaatcgttat tgctggttta      60
tgtcttgcaa tagtagctat cttaagttta atgattggaa atacgcttgt gtcaccaggt     120
acggtgatac aggcgttatt caactttgat agtgaaaacg atttacatga tgttgtcact     180
ggtgcacggg cgtcgagaac aatcattgcg ttattgactg tgctgcccct tgctgtctca     240
ggtttgttga tgcaagcact tacacgaaac ccaatagcct caccagggct tttcggtgtc     300
aatgcaggcg cagtattttt tgtcattttt agtattcat ttatccaaat tcaatctttt     360
aaaatgattg tagttattgc attttttgggg gctattgttg ttactgtatt agttgttgca     420
ctaggtatgt ttagacaaac actattctca cctcaccgtg tcattttggc aggtgctgcg     480
attgcgatgc tatttacagc ctttactcaa ggcatactta ttatgaacga aacagactta     540
```

-continued

```
caaggcctat tattttggtt aagtggctcc gtttcattac gtaatatttg ggatatccca    600
tggattattc cgcttgtatt gatacttatt ttaattgcat ttagcatggc tgcacacatc    660
aacatcttga tgacaagtga cgacattgca accggcctcg gtcaaaacat aaaattaatc    720
aaatggatga ttattatgct catcagtatg ttagccggta tttcggtagc cgtagctgga    780
tcaatcgtct ttgtgggtct tatcgtaccg aatattagca aacgattatt accaccaaac    840
tataagtatt taattccttt tactgcatta gctggagcaa tcctaatgat catttcagac    900
attgttgctc gtataataat taagccacta gagttgccta cggtgtcgt taccgctgtc    960 attggcgcta ttgtcttaat ctatattatg aagaaaggac gtcaacgctt atga         1014
```

<210> SEQ ID NO 18
<211> LENGTH: 331
<212> TYPE: PRT
<213> ORGANISM: Staphylococcus aureus

<400> SEQUENCE: 18

```
Met Leu Leu Lys Pro Lys Tyr Gln Ile Val Ile Ala Gly Leu Cys Leu
  1               5                  10                  15

Ala Ile Val Ala Ile Leu Ser Leu Met Ile Gly Asn Thr Leu Val Ser
             20                  25                  30

Pro Gly Thr Val Ile Gln Ala Leu Phe Asn Phe Asp Ser Glu Asn Asp
         35                  40                  45

Leu His Asp Val Val Thr Gly Ala Arg Ala Ser Arg Thr Ile Ile Ala
     50                  55                  60

Leu Leu Thr Gly Ala Ala Leu Ala Val Ser Gly Leu Leu Met Gln Ala
 65                  70                  75                  80

Leu Thr Arg Asn Pro Ile Ala Ser Pro Gly Leu Phe Gly Val Asn Ala
                 85                  90                  95

Gly Ala Val Phe Phe Val Ile Phe Ser Ile Thr Phe Ile Gln Ile Gln
            100                 105                 110

Ser Phe Lys Met Ile Val Val Ile Ala Phe Leu Gly Ala Ile Val Val
        115                 120                 125

Thr Val Leu Val Val Ala Leu Gly Met Phe Arg Gln Thr Leu Phe Ser
    130                 135                 140

Pro His Arg Val Ile Leu Ala Gly Ala Ala Ile Ala Met Leu Phe Thr
145                 150                 155                 160

Ala Phe Thr Gln Gly Ile Leu Ile Met Asn Glu Thr Asp Leu Gln Gly
                165                 170                 175

Leu Leu Phe Trp Leu Ser Gly Ser Val Ser Leu Arg Asn Ile Trp Asp
            180                 185                 190

Ile Pro Trp Ile Ile Pro Leu Val Leu Ile Leu Ile Leu Ile Ala Phe
        195                 200                 205

Ser Met Ala Ala His Ile Asn Ile Leu Met Thr Ser Asp Asp Ile Ala
    210                 215                 220

Thr Gly Leu Gly Gln Asn Ile Lys Leu Ile Lys Trp Met Ile Ile Met
225                 230                 235                 240

Leu Ile Ser Met Leu Ala Gly Ile Ser Val Ala Val Ala Gly Ser Ile
                245                 250                 255

Val Phe Val Gly Leu Ile Val Pro Asn Ile Ser Lys Arg Leu Leu Pro
            260                 265                 270

Pro Asn Tyr Lys Tyr Leu Ile Pro Phe Thr Ala Leu Ala Gly Ala Ile
        275                 280                 285
```

```
Leu Met Ile Ile Ser Asp Ile Val Ala Arg Ile Ile Lys Pro Leu
    290                 295                 300

Glu Leu Pro Ile Gly Val Val Thr Ala Val Ile Gly Ala Ile Val Leu
305                 310                 315                 320

Ile Tyr Ile Met Lys Lys Gly Arg Gln Arg Leu
                325                 330

<210> SEQ ID NO 19
<211> LENGTH: 1089
<212> TYPE: DNA
<213> ORGANISM: Staphylococcus aureus

<400> SEQUENCE: 19
taagccacta gagttgccta tcggtgtcgt taccgctgtc attggcgcta ttgtcttaat      60
ctatattatg aagaaaggac gtcaacgctt atgaccgaaa agattaataa aaaagacaat    120
taccatctca tcttcgcgtt aatctttta gccatcgttt cagtggtaag tatgatgatt    180
ggttcaagct ttataccatt acaacgcgta ctgatgtact ttataaatcc aaatgacagt    240
atggatcaat tcactttaga agtattacgc ttacctcgca ttacacttgc gattttagca    300
ggtgccgcac taggaatgag tggtttaatg ttgcaaaatg tattaaaaaa tccaattgcc    360
tcacctgata ttatcggtat cacaggtggt gctagcttaa gtgctgttgt ctttattgca    420
tttttcagcc atttaacaat acatttactt ccactatttg cagtattagg tggcgcagtt    480
gcaatgatga tactattagt gtttcaaacg aaaggacaaa tacgcccgac aacactcata    540
atcatcggta tttcgatgca aacgttgttt attgcgcttg tccaaggatt actcattaca    600
acgaagcaat tatctgctgc caaagcttat acatggctag tcggaagtct ttacggtgct    660
acgtttaaag atacaatcat tttgggtatg gttatttag ctgttgtgcc gttgttattt    720
cttgttatac caaaaatgaa aatatctata cttgatgacc ctgtagcgat tggcttaggc    780
ttacatgtac aacgtatgaa actaatccaa ttaatcactt ctactatact cgtatctatg    840
gcaatcagtt tagtaggtaa cattgggttt gtcggtttaa tcgcaccaca tatcgcgaaa    900
acaatcgttc gcggaagtta tgctaaaaag ttactaatgt cagcaatgat tggtgccata    960
tcaattgtta ttgcagactt aattgggcgt accttattct tgcctaaaga agtgccagca   1020
ggtgtattta ttgctgcttt tggtgcccca ttcttcatat acttattatt aaccgtgaaa   1080
aagttataa                                                           1089

<210> SEQ ID NO 20
<211> LENGTH: 332
<212> TYPE: PRT
<213> ORGANISM: Staphylococcus aureus

<400> SEQUENCE: 20

Met Thr Glu Lys Ile Asn Lys Lys Asp Asn Tyr His Leu Ile Phe Ala
1               5                   10                  15

Leu Ile Phe Leu Ala Ile Val Ser Val Val Ser Met Met Ile Gly Ser
                20                  25                  30

Ser Phe Ile Pro Leu Gln Arg Val Leu Met Tyr Phe Ile Asn Pro Asn
            35                  40                  45

Asp Ser Met Asp Gln Phe Thr Leu Glu Val Leu Arg Leu Pro Arg Ile
        50                  55                  60

Thr Leu Ala Ile Leu Ala Gly Ala Ala Leu Gly Met Ser Gly Leu Met
65                  70                  75                  80

Leu Gln Asn Val Leu Lys Asn Pro Ile Ala Ser Pro Asp Ile Ile Gly
```

```
                    85                  90                  95
Ile Thr Gly Gly Ala Ser Leu Ser Ala Val Val Phe Ile Ala Phe Phe
            100                 105                 110
Ser His Leu Thr Ile His Leu Leu Pro Leu Phe Ala Val Leu Gly Gly
            115                 120                 125
Ala Val Ala Met Met Ile Leu Leu Val Phe Gln Thr Lys Gly Gln Ile
            130                 135                 140
Arg Pro Thr Thr Leu Ile Ile Gly Ile Ser Met Gln Thr Leu Phe
145                 150                 155                 160
Ile Ala Leu Val Gln Gly Leu Leu Ile Thr Thr Lys Gln Leu Ser Ala
                165                 170                 175
Ala Lys Ala Tyr Thr Trp Leu Val Gly Ser Leu Tyr Gly Ala Thr Phe
            180                 185                 190
Lys Asp Thr Ile Ile Leu Gly Met Val Ile Leu Ala Val Val Pro Leu
            195                 200                 205
Leu Phe Leu Val Ile Pro Lys Met Lys Ile Ser Ile Leu Asp Asp Pro
    210                 215                 220
Val Ala Ile Gly Leu Gly Leu His Val Gln Arg Met Lys Leu Ile Gln
225                 230                 235                 240
Leu Ile Thr Ser Thr Ile Leu Val Ser Met Ala Ile Ser Leu Val Gly
            245                 250                 255
Asn Ile Gly Phe Val Gly Leu Ile Ala Pro His Ile Ala Lys Thr Ile
            260                 265                 270
Val Arg Gly Ser Tyr Ala Lys Lys Leu Leu Met Ser Ala Met Ile Gly
            275                 280                 285
Ala Ile Ser Ile Val Ile Ala Asp Leu Ile Gly Arg Thr Leu Phe Leu
            290                 295                 300
Pro Lys Glu Val Pro Ala Gly Val Phe Ile Ala Ala Phe Gly Ala Pro
305                 310                 315                 320
Phe Phe Ile Tyr Leu Leu Leu Thr Val Lys Lys Leu
            325                 330

<210> SEQ ID NO 21
<211> LENGTH: 1460
<212> TYPE: DNA
<213> ORGANISM: Staphylococcus aureus

<400> SEQUENCE: 21
taatgacact tattttttga aaataatagt aatatcattt tgttaaatga agaataaag      60 ctataataat tatagaataa ctatttaaag gagattataa acatgccaat tattacagat    120
gtttacgctc gcgaagtctt agactctcgt ggtaacccaa ctgttgaagt agaagtatta    180
actgaaagtg gcgcatttgg tcgtgcatta gtaccatcag gtgcttcaac tggtgaacac    240
gaagctgttg aattacgtga tggagacaaa tcacgttatt aggtaaagg tgttactaaa     300 gcagttgaaa acgttaatga aatcatcgca ccagaaatta ttgaaggtga atttcagta    360 ttagatcaag tatctattga taaaatgatg atcgcattag acggtactcc aaacaaaggt    420
aaattaggtg caaatgctat tttaggtgta tctatcgcag tagcacgtgc agcagctgac    480
ttattaggtc aaccactta caaatattta ggtggattta atggtaagca gttaccagta    540
ccaatgatga acatcgttaa tggtggttct cactcagatg ctccaattgc attccaagaa    600
ttcatgattt tacctgtagg tgctacaacg ttcaaagaat cattacgttg gggtactgaa    660
attttccaca acttaaaatc aatttaagc caacgtggtt tagaaactgc cgtaggtgac    720
```

-continued

```
gaaggtggtt tcgctcctaa atttgaaggt actgaagatg ctgttgaaac aattatccaa    780
gcaatcgaag cagctggtta caaaccaggt gaagaagtat tcttaggatt tgactgtgca    840
tcatcagaat tctatgaaaa tggtgtatat gactacagta agttcgaagg cgaacacggt    900
gcaaaacgta cagctgcaga acaagttgac tacttagaac aattagtaga caaatatcct    960
atcattacaa ttgaagacgg tatggacgaa aacgactggg atggttggaa acaacttaca   1020
gaacgtatcg gtgaccgtgt acaattagta ggtgacgatt tattcgtaac aaacactgaa   1080
attttagcaa aaggtattga aaacggaatt ggtaactcaa tcttaattaa agttaaccaa   1140
atcggtacat taactgaaac atttgatgca atcgaaatgg ctcaaaaagc tggttacaca   1200
gcagtagttt ctcaccgttc aggtgaaaca gaagatacaa caattgctga tattgctgtt   1260
gctacaaacg ctggtcaaat taaaactggt tcattatcac gtactgaccg tattgctaaa   1320
tacaatcaat tattacgtat cgaagatgaa ttatttgaaa ctgctaaata tgacggtatc   1380
aaatcattct ataacttaga taataatttt tctttataat caaatgctga cataatttta   1440
gttgaggatt attatgacgg                                                1460
```

<210> SEQ ID NO 22
<211> LENGTH: 434
<212> TYPE: PRT
<213> ORGANISM: Staphylococcus aureus

<400> SEQUENCE: 22

```
Met Pro Ile Ile Thr Asp Val Tyr Ala Arg Glu Val Leu Asp Ser Arg
  1               5                  10                  15

Gly Asn Pro Thr Val Glu Val Glu Val Leu Thr Glu Ser Gly Ala Phe
                 20                  25                  30

Gly Arg Ala Leu Val Pro Ser Gly Ala Ser Thr Gly Glu His Glu Ala
             35                  40                  45

Val Glu Leu Arg Asp Gly Asp Lys Ser Arg Tyr Leu Gly Lys Gly Val
         50                  55                  60

Thr Lys Ala Val Glu Asn Val Asn Glu Ile Ile Ala Pro Glu Ile Ile
 65                  70                  75                  80

Glu Gly Glu Phe Ser Val Leu Asp Gln Val Ser Ile Asp Lys Met Met
                 85                  90                  95

Ile Ala Leu Asp Gly Thr Pro Asn Lys Gly Lys Leu Gly Ala Asn Ala
                100                 105                 110

Ile Leu Gly Val Ser Ile Ala Val Ala Arg Ala Ala Ala Asp Leu Leu
            115                 120                 125

Gly Gln Pro Leu Tyr Lys Tyr Leu Gly Gly Phe Asn Gly Lys Gln Leu
        130                 135                 140

Pro Val Pro Met Met Asn Ile Val Asn Gly Gly Ser His Ser Asp Ala
145                 150                 155                 160

Pro Ile Ala Phe Gln Glu Phe Met Ile Leu Pro Val Gly Ala Thr Thr
                165                 170                 175

Phe Lys Glu Ser Leu Arg Trp Gly Thr Glu Ile Phe His Asn Leu Lys
            180                 185                 190

Ser Ile Leu Ser Gln Arg Gly Leu Glu Thr Ala Val Gly Asp Glu Gly
        195                 200                 205

Gly Phe Ala Pro Lys Phe Glu Gly Thr Glu Asp Ala Val Glu Thr Ile
    210                 215                 220

Ile Gln Ala Ile Glu Ala Ala Gly Tyr Lys Pro Gly Glu Glu Val Phe
225                 230                 235                 240
```

-continued

```
Leu Gly Phe Asp Cys Ala Ser Ser Glu Phe Tyr Glu Asn Gly Val Tyr
                245                 250                 255

Asp Tyr Ser Lys Phe Glu Gly Glu His Gly Ala Lys Arg Thr Ala Ala
            260                 265                 270

Glu Gln Val Asp Tyr Leu Glu Gln Leu Val Asp Lys Tyr Pro Ile Ile
        275                 280                 285

Thr Ile Glu Asp Gly Met Asp Glu Asn Asp Trp Asp Gly Trp Lys Gln
    290                 295                 300

Leu Thr Glu Arg Ile Gly Asp Arg Val Gln Leu Val Gly Asp Asp Leu
305                 310                 315                 320

Phe Val Thr Asn Thr Glu Ile Leu Ala Lys Gly Ile Glu Asn Gly Ile
                325                 330                 335

Gly Asn Ser Ile Leu Ile Lys Val Asn Gln Ile Gly Thr Leu Thr Glu
            340                 345                 350

Thr Phe Asp Ala Ile Glu Met Ala Gln Lys Ala Gly Tyr Thr Ala Val
        355                 360                 365

Val Ser His Arg Ser Gly Glu Thr Glu Asp Thr Thr Ile Ala Asp Ile
    370                 375                 380

Ala Val Ala Thr Asn Ala Gly Gln Ile Lys Thr Gly Ser Leu Ser Arg
385                 390                 395                 400

Thr Asp Arg Ile Ala Lys Tyr Asn Gln Leu Leu Arg Ile Glu Asp Glu
                405                 410                 415

Leu Phe Glu Thr Ala Lys Tyr Asp Gly Ile Lys Ser Phe Tyr Asn Leu
            420                 425                 430

Asp Lys
```

STAPHYLOCOCCUS AUREUS GENES AND POLYPEPTIDES

CROSS REFERENCE TO RELATED APPLICATIONS

This application is a divisional of and claims priority under 35 U.S.C. § 120 to U.S. application Ser. No. 09/830,217, filed Jan. 15, 2002 now U.S. Pat. No. 6,521,441, which is the National Stage of International Application No. PCT/US99/06199, filed Mar. 18, 1999, which claims priority to U.S. Provisional Application Nos. 60/084,674, filed May 7, 1998, 60/080,296, filed Apr. 1, 1998, and 60/078,682, filed Mar. 20, 1998. All of the foregoing applications are hereby incorporated by reference herein.

FIELD OF THE INVENTION

The present invention relates to novel *Staphylococcus aureus* genes (*S. aureus*) nucleic acids and polypeptides. Also provided are vectors, host cells and recombinant methods for producing the same. Further provided are diagnostic methods for detecting *Staphylococcus aureus* using probes, primers, and antibodies to the *S. aureus* nucleic acids and polypeptides of the present invention. The invention further relates to screening methods for identifying agonists and antagonists of *S. aureus* polypeptide activity and to vaccines using *S. aureus* nucleic acids and polypeptides.

BACKGROUND OF THE INVENTION

The genus *Staphylococcus* includes at least 20 distinct species. (For a review see Novick, R. P., The *Staphylococcus* as a Molecular Genetic System in MOLECULAR BIOLOGY OF THE STAPHYLOCOCCI, 1–37 (R. Novick, Ed., VCH Publishers, New York (1990)). Species differ from one another by 80% or more, by hybridization kinetics, whereas strains within a species are at least 90% identical by the same measure.

The species *S. aureus*, a gram-positive, facultatively aerobic, clump-forming cocci, is among the most important etiological agents of bacterial infection in humans, as discussed briefly below.

Human Health and *S. aureus*

*Staphylococcus aureus* is a ubiquitous pathogen. See, e.g., Mims et al., MEDICAL MICROBIOLOGY (Mosby-Year Book Europe Limited, London, UK 1993). It is an etiological agent of a variety of conditions, ranging in severity from mild to fatal. A few of the more common conditions caused by *S. aureus* infection are burns, cellulitis, eyelid infections, food poisoning, joint infections, neonatal conjunctivitis, osteomyelitis, skin infections, surgical wound infection, scalded skin syndrome and toxic shock syndrome, some of which are described further below.

Burns: Burn wounds generally are sterile initially. However, they generally compromise physical and immune barriers to infection, cause loss of fluid and electrolytes and result in local or general physiological dysfunction. After cooling, contact with viable bacteria results in mixed colonization at the injury site. Infection may be restricted to the non-viable debris on the burn surface ("eschar"), it may progress into full skin infection and invade viable tissue below the eschar and it may reach below the skin, enter the lymphatic and blood circulation and develop into septicemia. *S. aureus* is among the most important pathogens typically found in burn wound infections. It can destroy granulation tissue and produce severe septicemia.

Cellulitis: Cellulitis, an acute infection of the skin that expands from a typically superficial origin to spread below the cutaneous layer, most commonly is caused by *S. aureus* in conjunction with *S. pyrogenes*. Cellulitis can lead to systemic infection. In fact, cellulitis can be one aspect of synergistic bacterial gangrene. This condition typically is caused by a mixture of *S. aureus* and microaerophilic streptococci. It causes necrosis and treatment is limited to excision of the necrotic tissue. The condition often is fatal.

Eyelid infections: *S. aureus* is the cause of styes and of sticky eye" in neonates, among other eye infections. Typically such infections are limited to the surface of the eye, and may occasionally penetrate the surface with more severe consequences.

Food poisoning: Some strains of *S. aureus* produce one or more of five serologically distinct, heat and acid stable enterotoxins that are not destroyed by digestive process of the stomach and small intestine (enterotoxins A–E). Ingestion of the toxin, in sufficient quantities, typically results in severe vomiting, but not diarrhea. The effect does not require viable bacteria. Although the toxins are known, their mechanism of action is not understood.

Joint infections: *S. aureus* infects bone joints causing diseases such osteomyelitis. See, e.g., R. Cunningham et al., (1996) J. Med. Microbiol. 44:157–164.

Osteomyelitis: *S. aureus* is the most common causative agent of haematogenous osteomyelitis. The disease tends to occur in children and adolescents more than adults and it is associated with non-penetrating injuries to bones. Infection typically occurs in the long end of growing bone, hence its occurrence in physically immature populations. Most often, infection is localized in the vicinity of sprouting capillary loops adjacent to epiphysis growth plates in the end of long, growing bones.

Skin infections: *S. aureus* is the most common pathogen of such minor skin infections as abscesses and boils. Such infections often are resolved by normal host response mechanisms, but they also can develop into severe internal infections. Recurrent infections of the nasal passages plague nasal carriers of *S. aureus*.

Surgical Wound Infections: Surgical wounds often penetrate far into the body. Infection of such wound thus poses a grave risk to the patient. *S. aureus* is the most important causative agent of infections in surgical wounds. *S. aureus* is unusually adept at invading surgical wounds; sutured wounds can be infected by far fewer *S. aureus* cells then are necessary to cause infection in normal skin. Invasion of surgical wound can lead to severe *S. aureus* septicemia. Invasion of the blood stream by *S. aureus* can lead to seeding and infection of internal organs, particularly heart valves and bone, causing systemic diseases, such as endocarditis and osteomyelitis.

Scalded Skin Syndrome: *S. aureus* is responsible for "scalded skin syndrome" (also called toxic epidermal necrosis, Ritter's disease and Lyell's disease). This diseases occurs in older children, typically in outbreaks caused by flowering of *S. aureus* strains produce exfoliation (also called scalded skin syndrome toxin). Although the bacteria initially may infect only a minor lesion, the toxin destroys intercellular connections, spreads epidermal layers and allows the infection to penetrate the outer layer of the skin, producing the desquamation that typifies the diseases. Shedding of the outer layer of skin generally reveals normal skin below, but fluid lost in the process can produce severe injury in young children if it is not treated properly.

Toxic Shock Syndrome: Toxic shock syndrome is caused by strains of *S. aureus* that produce the so-called toxic shock syndrome toxin. The disease can be caused by *S. aureus* infection at any site, but it is too often erroneously viewed exclusively as a disease solely of women who use tampons. The disease involves toxemia and septicemia, and can be fatal.

Nocosomial Infections: In the 1984 National Nocosomial Infection Surveillance Study ("NNIS") S. aureus was the most prevalent agent of surgical wound infections in many hospital services, including medicine, surgery, obstetrics, pediatrics and newborns.

Other Infections: Other types of infections, risk factors, etc. involving S. aureus are discussed in: A. Trilla (1995) J. Chemotherapy 3:37–43; F. Espersen (1995) J. Chemotherapy 3:11–17; D. E. Craven (1995) J. Chemotherapy 3:19–28; J. D. Breen et al. (1995) Infect. Dis. Clin. North Am. 9(1):11–24 (each incorporated herein in their entireties).

Resistance to Drugs of S. aureus Strains

Prior to the introduction of penicillin the prognosis for patients seriously infected with S. aureus was unfavorable. Following the introduction of penicillin in the early 1940s even the worst S. aureus infections generally could be treated successfully. The emergence of penicillin-resistant strains of S. aureus did not take long, however. Most strains of S. aureus encountered in hospital infections today do not respond to penicillin; although, fortunately, this is not the case for S. aureus encountered in community infections.

It is well known now that penicillin-resistant strains of S. aureus produce a lactamase which converts penicillin to pencillinoic acid, and thereby destroys antibiotic activity. Furthermore, the lactamase gene often is propagated episomally, typically on a plasmid, and often is only one of several genes on an episomal element that, together, confer multidrug resistance.

Methicillins, introduced in the 1960s, largely overcame the problem of penicillin resistance in S. aureus. These compounds conserve the portions of penicillin responsible for antibiotic activity and modify or alter other portions that make penicillin a good substrate for inactivating lactamases. However, methicillin resistance has emerged in S. aureus, along with resistance to many other antibiotics effective against this organism, including aminoglycosides, tetracycline, chloramphenicol, macrolides and lincosamides. In fact, methicillin-resistant strains of S. aureus generally are multiply drug resistant.

Methicillian-resistant S. aureus (MRSA) has become one of the most important nosocomial pathogens worldwide and poses serious infection control problems. Today, many strains are multiresistant against virtually all antibiotics with the exception of vancomycin-type glycopeptide antibiotics.

Recent reports that transfer of vancomycin resistance genes from enterococci to S. aureus has been observed in the laboratory sustain that fear that MRSA might become resistant against vancomycin, too, a situation generally considered to result in a public health disaster. MRSA owe their resistance against virtually all β-lactam antibiotics to the expression of an extra penicillin binding protein (PBP) 2a, encoded by the mecA gene. This additional very low affinity pbp, which is found exclusively in resistant strains, appears to be the only pbp still functioning in cell wall peptidoglycan synthesis at β-lactam concentrations high enough to saturate the normal set of S. aureus pbp 1–4. In 1983 it was shown by insertion mutagenesis using transposon Tn551 that several additional genes independent of mecA are needed to sustain the high level of methicillin resistance of MRSA. Interruption of these genes did not influence the resistance level by interfering with PBP2a expression, and were therefore called fem (factor essential for expression of methicillin resistance) or aux (auxiliary genes).

In the meantime six fem genes (femA- through F) have been described and the minimal number of additional aux genes has been estimated to be more than 10. Interference with fema and femB results in a strong reduction of methicillin resistance, back to sensitivity of strains without PBP2a. The fem genes are involved in specific steps of cell wall synthesis. Consequently, inactivation of fem factors induce β-lactam hypersensitivity in already sensitive strains. Both femA and femB have been shown to be involved in peptidoglycan pentaglycine interpeptide bridge formation. FemA is responsible for the formation of glycines 2 and 3, and femB is responsible for formation of glycines 4 and 5. S. aureus may be involved in the formation of a monoglycine muropeptide precursors. FemC-F influence amidation of the iso-D-glutamic acid residue of the peptidoglycan stem peptide, formation of a minor muropeptide with L-alanine instead of glycine at position 1 of the interpeptide bridge, perform a yet unknown function, or are involved in an early step of peptidoglycan precursors biosynthesis (addition of L-lysine), respectively.

Thus far each new antibiotic gives rise to resistance strains, emerge that are resistance to multiple drugs and increasingly persistent forms of resistance begin to emerge. Drug resistance of S. aureus infections already poses significant treatment difficulties, which are likely to get much worse unless new therapeutic agents are developed. Since S. aureus is likely involved in the synthesis of the peptidoglycan cross bridges in S. aureus, the gene provides an important tool in studying the mechanisms of antibiotic resistance. The S. aureus gene and its polypeptides are also potential target for antagonists or agonists, which may be useful as antibiotics, or useful to block resistance to other antibiotics. That is, antagonists or agonists, such as small molecules, may be useful as antibiotics themselves, act additively with other antibiotics, or act synergistically with other antibiotics.

BRIEF SUMMARY OF THE INVENTION

The present invention provides isolated S. aureus polynucleotides and polypeptides shown in Table 1 and SEQ ID NO:1 through SEQ ID NO:22 (polynucleotide sequences having odd SEQ ID NOs and polypeptide sequences having even SEQ ID NOs). One aspect of the invention provides isolated nucleic acid molecules comprising polynucleotides having a nucleotide sequence selected from the group consisting of: (a) a nucleotide sequence shown in Table 1; (b) a nucleotide sequence encoding any of the amino acid sequences of the polypeptides shown in Table 1; and (c) a nucleotide sequence complementary to any of the nucleotide sequences in (a) or (b). The invention further provides for fragments of the nucleic acid molecules of (a), (b) & (c) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b) or (c) above, or a polynucleotide which hybridizes under stringent hybridization conditions to a polynucleotide in (a), (b) or (c) above. Additional nucleic acid embodiments of the invention relate to isolated nucleic acid molecules comprising polynucleotides which encode the amino acid sequences of epitope-bearing portions of a S. aureus polypeptide having an amino acid sequence in (a) above.

The present invention also relates to recombinant vectors, which include the isolated nucleic acid molecules of the present invention, and to host cells containing the recombinant vectors, as well as to methods of making such vectors and host cells. The present invention further relates to the use of these vectors in the production of *S. aureus* polypeptides or peptides by recombinant techniques.

The invention further provides isolated *S. aureus* polypeptides having an amino acid sequence selected from the group consisting of an amino acid sequence of any of the polypeptides described in Table 1 or fragments thereof.

The polypeptides of the present invention also include polypeptides having an amino acid sequence with at least 70% similarity, and more preferably at least 75%, 80%, 85%, 90%, 95%, 96%, 97%, 98%, or 99% similarity to those described in Table 1, as well as polypeptides having an amino acid sequence at least 70% identical, more preferably at least 75% identical, and still more preferably 80%, 85%, 90%, 95%, 96%, 97%, 98%, or 99% identical to those above; as well as isolated nucleic acid molecules encoding such polypeptides.

The present invention further provides a vaccine, preferably a multi-component vaccine comprising one or more of the *S. aureus* polynucleotides or polypeptides described in Table 1, or fragments thereof, together with a pharmaceutically acceptable diluent, carrier, or excipient, wherein the *S. aureus* polypeptide(s) are present in an amount effective to elicit an immune response to members of the *Staphylococcus* genus, or at least *S. aureus*, in an animal. The *S. aureus* polypeptides of the present invention may further be combined with one or more immunogens of one or more other staphylococcal or non-staphylococcal organisms to produce a multi-component vaccine intended to elicit an immunological response against members of the *Staphylococcus* genus and, optionally, one or more non-staphylococcal organisms.

The vaccines of the present invention can be administered in a DNA form, e.g., "naked" DNA, wherein the DNA encodes one or more staphylococcal polypeptides and, optionally, one or more polypeptides of a non-staphylococcal organism. The DNA encoding one or more polypeptides may be constructed such that these polypeptides are expressed as fusion proteins.

The vaccines of the present invention may also be administered as a component of a genetically engineered organism or host cell. Thus, a genetically engineered organism or host cell which expresses one or more *S. aureus* polypeptides may be administered to an animal. For example, such a genetically engineered organism or host cell may contain one or more *S. aureus* polypeptides of the present invention intracellularly, on its cell surface, or in its periplasmic space. Further, such a genetically engineered organism or host cell may secrete one or more *S. aureus* polypeptides. The vaccines of the present invention may also be co-administered to an animal with an immune system modulator (e.g., CD86 and GM-CSF).

The invention also provides a method of inducing an immunological response in an animal to one or more members of the *Staphylococcus* genus, preferably one or more isolates of the *S. aureus* species, comprising administering to the animal a vaccine as described above.

The invention further provides a method of inducing a protective immune response in an animal, sufficient to prevent, attenuate, or control an infection by members of the *Staphylococcus* genus, preferably at least *S. aureus* species, comprising administering to the animal a composition comprising one or more of the polynucleotides or polypeptides described in Table 1, or fragments thereof. Further, these polypeptides, or fragments thereof, may be conjugated to another immunogen and/or administered in admixture with an adjuvant.

The invention further relates to antibodies elicited in an animal by the administration of one or more *S. aureus* polypeptides of the present invention and to methods for producing such antibodies and fragments thereof. The invention further relates to recombinant antibodies and fragments thereof and to methods for producing such antibodies and fragments thereof.

The invention also provides diagnostic methods for detecting the expression of the polynucleotides of Table 1 by members of the *Staphylococcus* genus in an animal. One such method involves assaying for the expression of a polynucleotide encoding *S. aureus* polypeptides in a sample from an animal. This expression may be assayed either directly (e.g., by assaying polypeptide levels using antibodies elicited in response to amino acid sequences described in Table 1) or indirectly (e.g., by assaying for antibodies having specificity for amino acid sequences described in Table 1). The expression of polynucleotides can also be assayed by detecting the nucleic acids of Table 1. An example of such a method involves the use of the polymerase chain reaction (PCR) to amplify and detect *Staphylococcus* nucleic acid sequences.

The present invention also relates to nucleic acid probes having all or part of a nucleotide sequence described in Table 1 (odd SEQ ID NOs) which are capable of hybridizing under stringent conditions to *Staphylococcus* nucleic acids. The invention further relates to a method of detecting one or more *Staphylococcus* nucleic acids in a biological sample obtained from an animal, said one or more nucleic acids encoding *Staphylococcus* polypeptides, comprising: (a) contacting the sample with one or more of the above-described nucleic acid probes, under conditions such that hybridization occurs, and (b) detecting hybridization of said one or more probes to the *Staphylococcus* nucleic acid present in the biological sample.

Polynucleotides and Polypeptides of the Invention
Features of femX Polynucleotides and Polypeptides.

The nucleotide sequence shown in SEQ ID NO:1 was determined by sequencing the *S. aureus* overlapping clones BTEFS71 and BTEJE39. The nucleotide sequence contains an open reading frame encoding the femX polypeptide comprising 414 amino acid residues (SEQ ID NO:2), including an initiation codon encoding an N-terminal methionine at nucleotide positions 164–166, and a predicted molecular weight of about 49.1 kDa.

The femX polypeptides of the present invention have amino acid sequence homology to known genes involved in formation of peptidoglycan cross bridges, including the conserved cysteine pattern characteristic of the epr and fem family of genes. The *S. aureus* femX polypeptide of SEQ ID NO:2 was found to share a high degree of local sequence identity with amino acid sequences of the epr (M. Sugai, et al. (1997) J. Bacteriol. 179(13):4311–4318) and fem A and fem B proteins from *Staphlococcus* species (A. M. Stranden et al., (1997) J. Bacteriol. 179(1):9–16; G. Thumm et al. (1997) Mol. Microbiol. 23(6):1251–1265; W. E. Alborn et al., (1996) Gene 180(1–2):177–181) using the computer program BLAST (Altschul et al., (1990) J. Mol. Biol. 215:403–410).

The strong homology between species and identity among fem proteins of *S. aureus* indicates that femX is involved in peptidoglycan interpeptide bridge biosynthesis. Thus, the polypeptides of the present invention are useful in screening methods to make antagonists which block their function. Antagonists can be used, for instance, as antibiotics to treat antibiotic resistant *S. aureus* or other *Staphylococcus* species. Antagonists of the polypeptides of the present invention can be identified by measuring the formation of peptidoglycan cross bridges. More specifically, the synthesis of glycines 1–5 of peptidoglycan cross bridges can be measured as exemplified by A. M. Stranden et al. (1997) J. Bacteriol 179(1):9–16 (incorporated herein in its entirety). Antagonists of femX would act to inhibit peptidoglycan cross bridge formation.

Other uses of the femX polypeptides of the present invention include: inter alia, to detect S. aureus in immunoassays, as epitope tags, as molecular weight markers on SDS-PAGE gels, as molecular weight markers for molecular sieve gel filtration columns, to generate antibodies that specifically bind S. aureus femX for the detection S. aureus in immunoassays, to generate an immune response against S. aureus and other Staphylococcus species, and as vaccines against S. aureus and other Staphylococcus species.

Isolated nucleic acid molecules of the present invention, particularly DNA molecules, are useful as probes for gene mapping and for identifying S. aureus in a biological samples, for instance, by Southern and Northern blot analysis. femX polynucleotides of the present invention are also useful in detecting S. aureus by PCR using primers for femX polynucleotides. Isolated polynucleotides of the present invention are also useful in making the polypeptides of the present invention.

Features of furA, furB, and furC Polynucleotides and Polypeptides.

The nucleotide sequences for furA, furB, and furC were determined by sequencing the S. aureus clones BTEJQ50 (SEQ ID NO:3), BTALE70 (SEQ ID NO:5), and BTEBP80 and BTEFD68 (collectively SEQ ID NO:7). The nucleotide sequence of SEQ ID NO:3 contains an open reading frame encoding the furA polypeptide comprising 136 amino acid residues (SEQ ID NO:4), including an initiation codon encoding an N-terminal methionine at nucleotide positions 101–103, and a predicted molecular weight of about 15.9 kDa.

The nucleotide sequence of SEQ ID NO:5 contains an open reading frame encoding the furB polypeptide comprising 148 amino acid residues (SEQ ID NO:6), including an initiation codon encoding an N-terminal methionine at nucleotide positions 101–103, and a predicted molecular weight of about 17.2 kDa.

The nucleotide sequence of SEQ ID NO:7 contains an open reading frame encoding the furC polypeptide comprising 149 amino acid residues (SEQ ID NO:8), including an initiation codon encoding an N-terminal leucine at nucleotide positions 101–103, and a predicted molecular weight of about 17.2 kDa.

The fur (ferric uptake regulator) polypeptides (furA, furB, and furC) of the present invention have amino acid sequence homology to known genes involved in iron regulation. The S. aureus furA polypeptide of SEQ ID NO:2 was found to share a high degree of local sequence identity with the amino acid sequence of a fur gene from Staphylococcus epidermidis (GenBank accession number gnl|PID|e236389). See C. Heidrich et al. (1996) FEMS Micro. Letts. 140:253–259. The S. aureus furB polypeptide of SEQ ID NO:2 was found to share a high degree of local sequence identity with the amino acid sequence of a fur family gene from Bacillus subtilis (GenBank accession number gnl|PID|e281583). See N. J Cummings et al. (1997) Microbiology 143:1855–1859. The S. aureus furC polypeptide of SEQ ID NO:2 was found to share a high degree of local sequence identity with the amino acid sequence of another fur family gene from Bacillus subtilis (GenBank accession number gnl|PID|e1185621). See F. Kunst et al. (1997) Nature 390:249–256.

The fur polypeptides of the present invention also share identity among themselves as well as other fur and fur-like genes from Bacillus subtilis (GenBank accession numbers gnl|PID|e1185777), Streptococcus pyogenes (GenBank accession number gi|1667516), Neisseria meningitidis (GenBank accession number gi|433299), Neisseria gonorrheae (GenBank accession number gi|349012), Camplyobacter upsaliensis (GenBank accession number gi|1228779), Camplyobacter jejuni (GenBank accession number gi|511113) Mycobacterium tuberculosis (GenBank accession numbergnl|PID|e315163), and other bacteria species. Identities were compared using the computer program BLAST (Altschul et al., (1990) J. Mol. Biol. 215:403–410).

The strong homology among the fur proteins of S. aureus and other bacteria species indicates that furA, furB, and furC are involved in iron regulation in S. aureus. Since iron is essential for the growth and multiplication of nearly microorganisms, the polypeptides of the present invention are useful in screening methods to make antagonists which block their function. Antagonists can be used, for instance, as antibiotics to treat infections of S. aureus or other Staphylococcus species. Antagonists of the polypeptides of the present invention can be identified by measuring the ability of bacteria to grow in the presence of varying concentrations of iron.

Other uses of the fur polypeptides of the present invention include: inter alia, to detect S. aureus in immunoassays, as epitope tags, as molecular weight markers on SDS-PAGE gels, as molecular weight markers for molecular sieve gel filtration columns, to generate antibodies that specifically bind S. aureus furA, furB, and furC for the detection S. aureus in immunoassays, to generate an immune response against S. aureus and other Staphylococcus species, and as vaccines against S. aureus, other Staphylococcus species and other bacteria genuses.

Isolated nucleic acid molecules of the present invention, particularly DNA molecules, are useful as probes for gene mapping and for identifying S. aureus in a biological samples, for instance, by Southern and Northern blot analysis. fur polynucleotides of the present invention are also useful in detecting S. aureus by PCR using primers for a particular fur polynucleotide. Isolated polynucleotides of the present invention are also useful in making the polypeptides of the present invention.

Features of fmtB, pbpF, and pbpG Polynucleotides and Polypeptides.

The nucleotide sequences for fmtB, pbpF, and pbpG were determined by sequencing the S. aureus clones BTEDA22 and BTEDV18 (SEQ ID NO:9), BTEBG73 and BTAJO70 (SEQ ID NO:11), and BTEBU53 and BTEFB55 (SEQ ID NO:13), respectively. The nucleotide sequence of SEQ ID NO:9 contains an open reading frame encoding the fmtB polypeptide comprising 498 amino acid residues (SEQ ID NO:10), including an initiation codon encoding an N-terminal methionine at nucleotide positions 101–103, and a predicted molecular weight of about 56.4 kDa.

The nucleotide sequence of SEQ ID NO:11 contains an open reading frame encoding the pbpF polypeptide comprising 691 amino acid residues (SEQ ID NO:12), including an initiation codon encoding an N-terminal leucine at nucleotide positions 101–103, and a predicted molecular weight of about 77.2 kDa.

The nucleotide sequence of SEQ ID NO:13 contains an open reading frame encoding the pbpG polypeptide comprising 301 amino acid residues (SEQ ID NO:14), including an initiation codon encoding an N-terminal methionine at nucleotide positions 101–103, and a predicted molecular weight of about 34.5 kDa.

The fmtB, pbpF, and pbpG polypeptides of the present invention have amino acid sequence homology to known penicillin-biding proteins among several species. The *S. aureus* fmtB polypeptide of SEQ ID NO:10 was found to share local sequence identity, inter alia, with the amino acid sequence of a penicillin-binding protein gene from *Bacillus subtilis* (GenBank accession number gnl|PID|e1185286). See F. Kunst et al. (1997) Nature 390:249–256. fmtB also shares sequence identity with another *Staphylococcus aureus* polypeptide associated with antibiotic resistance (GenBank accession number gnl|PID|d1024918). See H. Komatsuzawa et al. (1997) Antimicrob. Agents Chemother. 41:2355–2361.

The *S. aureus* pbpF polypeptide of SEQ ID NO:12 was found to share local sequence identity, inter alia, with the amino acid sequence of penicillin-binding genes from *Bacillus subtilis* (GenBank accession number gnl|PID|e1181903 and gnl|PID|e185767) and *Streptococcus thermophilus* (GenBank accession number gi|643510). The *S. aureus* pbpG polypeptide of SEQ ID NO:14 was found to share local sequence identity, inter alia, with the amino acid sequence of penicillin-binding genes from *Pseudomonas syringae* (GenBank accession number gi|551940). See E. Roine et al. (1996) J. Bacteriol. 178:410–417, and *Bacillus subtilis* (GenBank accession number gnl|PID|e267588). Identities were compared using the computer program BLAST (Altschul et al, (1990) J. Mol. Biol. 215:403–410).

The strong homology among the *S. aureus* fmtB, pbpF, and pbpG polypeptides of the present invention and penicillin-binding proteins from other bacteria species indicates that fmtB, pbpF, and pbpG are involved cell wall synthesis and in β-lactam resistance in *S. aureus*. The polypeptides of the present invention are therefore useful for making compounds that inhibit their function for use as antibiotics. Inhibitors of the polypeptides of the present invention can be identified by measuring the ability of bacteria to grow in the presence of varying concentrations of antibiotics or by cell wall synthesis assays using methods known in the art.

Other uses of the fmtB, pbpF, and pbpG polypeptides of the present invention include: inter alia, to detect *S. aureus* in immunoassays, as epitope tags, as molecular weight markers on SDS-PAGE gels, as molecular weight markers for molecular sieve gel filtration columns, to generate antibodies that specifically bind *S. aureus* fmtB, pbpF, or pbpG for the detection *S. aureus* in immunoassays, to generate an immune response against *S. aureus* and other *Staphylococcus* species, and as vaccines against *S. aureus*, other *Staphylococcus* species and other bacteria genuses.

Isolated nucleic acid molecules of the present invention, particularly DNA molecules, are useful as probes for gene mapping and for identifying *S. aureus* in a biological samples, for instance, by Southern and Northern blot analysis. fmtB, pbpF, and pbpG polynucleotides of the present invention are also useful in detecting *S. aureus* by PCR using primers for a particular fmtB, pbpF, or pbpG polynucleotide. Isolated polynucleotides of the present invention are also useful in making the polypeptides of the present invention.

Features of cbrA, cbrB, and cbrC Polynucleotides and Polypeptides.

The nucleotide sequences for cbrA (SEQ ID NO:15), cbrB (SEQ ID NO:17), and cbrC (SEQ ID NO:19) comprise a single operon and were determined by sequencing the *S. aureus* overlapping clones BTACA44 and BTAGJ54 which span the operon. The nucleotide sequence of SEQ ID NO:15 contains an open reading frame encoding the cbrA polypeptide comprising 330 amino acid residues (SEQ ID NO:16), including an initiation codon encoding an N-terminal methionine at nucleotide positions 7–9, and a predicted molecular weight of about 36.8 kDa.

The nucleotide sequence of SEQ ID NO:17 contains an open reading frame encoding the cbrB polypeptide comprising 331 amino acid residues (SEQ ID NO:18), including an initiation codon encoding an N-terminal leucine at nucleotide positions 19–21, and a predicted molecular weight of about 35.5 kDa.

The nucleotide sequence of SEQ ID NO:19 contains an open reading frame encoding the cbrC polypeptide comprising 332 amino acid residues (SEQ ID NO:20), including an initiation codon encoding an N-terminal methionine at nucleotide positions 91–93, and a predicted molecular weight of about 35.7 kDa.

The cbr polypeptides (cbrA, cbrB, and cbrC) of the present invention have amino acid sequence homology to known genes involved in iron regulation. The *S. aureus* cbrA (SEQ ID NO:16), cbrB (SEQ ID NO:18), and cbrC (SEQ ID NO:20) polypeptides were found to share local sequence identity among themselves and with the amino acid sequence of a cbrA, cbrB, and cbrC genes from *Erwinia chrysanthemi* (GenBank accession numbers gi|809541, gi|809542, and gi|809541 respectively). See B. Mahe et al. (1995) Mol. Microbiol. 18:33–43. The cbrA, cbrB, and cbrC polypeptides of the present invention also share sequence identity and with iron regulatory genes of other bacterial species including *Bacillus subtilis* (GenBank accession number gnl|PID|e1182834, gnl|PID|e1182835, and gnl|PID|e1182836). See F. Kunst et al. (1997) Nature 390:249–256 and *Bacillus intermedius* (GenBank accession number gnl|PID|e245932). Identities were compared using the computer program BLAST (Altschul et al., (1990) J. Mol. Biol. 215:403–410).

The strong homology among the cbr proteins of *S. aureus* and other bacteria species indicates that cbrA, cbrB, and cbrC are involved in iron regulation in *S. aureus*. Since iron is essential for the growth and multiplication of nearly microorganisms, the polypeptides of the present invention are useful in screening methods to make antagonists which block their function. Antagonists can be used, for instance, as antibiotics to treat infections of *S. aureus* or other *Staphylococcus* species. Antagonists of the polypeptides of the present invention can be identified by measuring the ability of bacteria to grow in the presence of varying concentrations of iron.

Other uses of the polypeptides of the present invention include: inter alia, to detect *S. aureus* in immunoassays, as epitope tags, as molecular weight markers on SDS-PAGE gels, as molecular weight markers for molecular sieve gel filtration columns, to generate antibodies that specifically bind *S. aureus* polypeptides of the present invention for the detection *S. aureus* in immunoassays, to generate an immune response against *S. aureus* and other *Staphylococcus* species, and as vaccines against *S. aureus*, other *Staphylococcus* species and other bacteria genuses.

Isolated nucleic acid molecules of the present invention, particularly DNA molecules, are useful as probes for gene mapping and for identifying *S. aureus* in a biological samples, for instance, by Southern and Northern blot analysis. *S. aureus* polynucleotides of the present invention are also useful in detecting *S. aureus* by PCR using primers for a particular *S. aureus* polynucleotide. Isolated polynucleotides of the present invention are also useful in making the polypeptides of the present invention.

Features of Enolase Polynucleotides and Polypeptides.

The nucleotide sequence shown in SEQ ID NO:21 was determined by sequencing the *S. aureus* overlapping clones BTAAI44 and BTAGE12. The nucleotide sequence contains an open reading frame encoding the enolase polypeptide comprising 434 amino acid residues (SEQ ID NO:22), including an initiation codon encoding an N-terminal methionine at nucleotide positions 103–105, and a predicted molecular weight of about 47.1 kDa.

The enolase polypeptides of the present invention have amino acid sequence identity homology to known enolase genes from other bacterial species. The *S. aureus* enolase polypeptide of SEQ ID NO:22 shares local sequence identity with amino acid sequences of the enolase genes from other bacterial species including *Bacillus subtilis* (GenBank accession numbers gi|460259 and gnl|PID|e1186078), Spongilla sp. (GenBank accession number gi|1839206), *Mycobacterium tuberculosis* (GenBank accession number gnl|PID|e304557) *Methanococcus jannaschii* (GenBank accession number gi|1590967) and *Campylobacter jejuni* (GenBank accession number gi|437277).

The *S. aureus* enolase protein of the present invention was identified as a molecule involved in laminin (LN)/laminin receptor (LNRec) interactions. The *S. aureus* enolase protein of the present invention was shown to be responsible for LNRec activity in bridging experiments between the *S. aureus* and MDCK cell in culture. The *S. aureus* enolase gene of the present invention was cloned by first generating monoclonal antibodies against the LNRec molecule and using the antibodies to subsequently isolated the LNRec molecule. The LNRec molecule was purified and partially sequenced. Partial amino acid sequence analysis was used to clone and isolate the *S. aureus* enolase gene of the present invention. A characteristic feature of infection by *S. aureus* is bloodstream invasion and widespread metastatic abscess formation. The *S. aureus* enolase polypeptides of the present invention therefore represent a target for both vaccines and antibiotics. Antibiotics of the present invention include peptides, polypeptides, antibodies (and fragments thereof), small molecules, and other drugs that bind the *S. aureus* enolase polypeptides of the present invention, or enolase associated molecules, and prevent binding of *S. aureus* to laminin. The blocking molecules of the present invention may act by directly blocking the binding of enolase polypeptides to laminin or enolase associated molecules to laminin. Assays for measuring the binding of molecules to enolase polypeptides or enolase associated molecules; assays for measuring the binding of *S. aureus* to laminin; and assays for measuring the metastatic activity of *S. aureus* include those described and referenced in Lopes et al. (1985) Science 229:275–277, described and referenced in Brentani (1989) Oncogenesis 1:247–260, known in the art, and disclosed herein.

The structural homology and identity between the enolase polypeptides of *S. aureus* and those of other bacterial species indicates that the enolase polypeptides of *S. aureus* share the same function as the enolase polypeptides from other bacterial enolase polypeptides, including those described by Babbitt et al. (1996) Biochemistry 35:16489–16501. The enolase polynucleotides and polypeptides of the present invention are useful to produce mutant *S. aureus* enolase genes, polypeptides, and mutant *S. aureus* strains for use as vaccines and to induce an immune response in humans and other animals by using the methods described in U.S. Pat. Nos. 5,703,219 and 5,703,219. In the methods of U.S. Pat. Nos. 5,703,219 and 5,703,219 the *S. aureus* enolase polypeptides and polypeptides are substituted for the *Helicobacter pyiori* enolase polypeptides and polypeptides. Modifications to accommodate the *S. aureus* enolase polypeptides and polypeptides of the present invention are made using information disclosed herein and known in the art.

Other uses of the enolase polypeptides of the present invention include: inter alia, to detect *S. aureus* in immunoassays, as epitope tags, as molecular weight markers on SDS-PAGE gels, as molecular weight markers for molecular sieve gel filtration columns, to generate antibodies that specifically bind *S. aureus* enolase for the detection *S. aureus* in immunoassays, to generate an immune response against *S. aureus* and other *Staphylococcus* species, and as vaccines against *S. aureus* and other *Staphylococcus* species as discussed above.

Isolated nucleic acid molecules of the present invention, particularly DNA molecules, are useful as probes for gene mapping and for identifying *S. aureus* in a biological samples, for instance, by Southern and Northern blot analysis. enolase polynucleotides of the present invention are also useful in detecting *S. aureus* by PCR using primers for enolase polynucleotides. Isolated polynucleotides of the present invention are also useful in making the polypeptides of the present invention.

DETAILED DESCRIPTION

The present invention relates to recombinant *S. aureus* nucleic acids and fragments thereof. The present invention further relates to recombinant *S. aureus* polypeptides and fragments thereof. The invention also relates to methods for using these polypeptides to produce immunological responses and to confer immunological protection to disease caused by members of the genus *Staphylococcus*, at least isolates of the *S. aureus* genus. The invention further relates to nucleic acid sequences which encode antigenic *S. aureus* polypeptides and to methods for detecting *S. aureus* nucleic acids and polypeptides in biological samples. The invention also relates to antibodies specific for the polypeptides and peptides of the present invention and methods for detecting such antibodies produced in a host animal.

Definitions

The following definitions are provided to clarify the subject matter which the inventors consider to be the present invention.

As used herein, the phrase "pathogenic agent" means an agent which causes a disease state or affliction in an animal. Included within this definition, for examples, are bacteria, protozoans, fungi, viruses and metazoan parasites which either produce a disease state or render an animal infected with such an organism susceptible to a disease state (e.g., a secondary infection). Further included are species and strains of the genus *Staphylococcus* which produce disease states in animals.

As used herein, the term "organism" means any living biological system, including viruses, regardless of whether it is a pathogenic agent.

As used herein, the term "*Staphylococcus*" means any species or strain of bacteria which is members of the genus *Staphylococcus*. Such species and strains are known to those of skill in the art, and include those that are pathogenic and those that are not.

As used herein, the phrase "one or more *S. aureus* polypeptides of the present invention" means polypeptides comprising the amino acid sequence of one or more of the *S. aureus* polypeptides described in Table 1 (even SEQ ID NOs). These polypeptides may be expressed as fusion proteins wherein the *S. aureus* polypeptides of the present invention are linked to additional amino acid sequences which may be of staphylococcal or non-staphylococcal origin. This phrase further includes polypeptide comprising fragments of the *S. aureus* polypeptides of the present invention. Additional definitions are provided throughout the specification.

Explanation of Table 1

Table 1, below, shows the nucleotide sequence of 11 genes from *S. aureus* and the sequence of the polypeptides they encode. The table lists the name of the *S. aureus* gene, followed by a sequence identification number (SEQ ID NO:), and the gene's nucleotide or polypeptide sequence. The table also lists the plasmid clones comprising the nucleotide sequences. The actual nucleotide or amino acid sequence of each gene is also shown in the Sequence Listing under the corresponding SEQ ID NO.

Explanation of Table 2

Table 2 lists residues comprising antigenic epitopes of antigenic epitope-bearing fragments present in each of the *S. aureus* polypeptides described in Table 1 as predicted by the inventors using the algorithm of Jameson and Wolf, (1988) Comp. Appl. Biosci. 4:181–186. The Jameson-Wolf antigenic analysis was performed using the computer program PROTEAN (Version 3.11 for the Power Macintosh, DNASTAR, Inc., 1228 South Park Street Madison, Wis.). Each *S. aureus* polypeptide shown in Table 1 has one or more antigenic epitopes comprising residues described in Table 2. It will be appreciated that depending on the analytical criteria used to predict antigenic determinants, the exact address of the determinant may vary slightly. The residues and locations shown described in Table 2 correspond to the amino acid sequences for each gene shown in Table 1 and in the Sequence Listing.

Explanation of Table 3.

The *S. aureus* polypeptides of the present invention may include one or more conservative amino acid substitutions from natural mutations or human manipulation as indicated in Table 3. Changes are preferably of a minor nature, such as conservative amino acid substitutions that do not significantly affect the folding or activity of the protein. Residues from the following groups, as indicated in Table 3, may be substituted for one another: Aromatic, Hydrophobic, Polar, Basic, Acidic, and Small.

Nucleic Acid Molecules

Sequenced *S. aureus* genomic DNA was obtained from the *S. aureus* strain ISP3. *S. aureus* strain ISP3, has been deposited at the American Type Culture Collection, as a convenience to those of skill in the art. The *S. aureus* strain ISP3 was deposited on Apr. 7, 1998 at the ATCC, 10801 University Blvd. Manassas, Va. 20110-2209, and given accession number 202108. As discussed elsewhere herein, polynucleotides of the present invention readily may be obtained by routine application of well known and standard procedures for cloning and sequencing DNA. Detailed methods for obtaining libraries and for sequencing are provided below, for instance. A wide variety of *Staphylococcus aureus* strains that can be used to prepare *S aureus* genomic DNA for cloning and for obtaining polynucleotides and polypeptides of the present invention. A wide variety of *Staphylococcus aureus* strains are available to the public from recognized depository institutions, such as the American Type Culture Collection (ATCC). It is recognized that minor variation is the nucleic acid and amino acid sequence may be expected from *S aureus* strain to strain. The present invention provides for genes, including both polynucleotides and polypeptides, of the present invention from all the *Staphylococcus aureus* strains. That is, the femX, furA-C, fmtB, pbpG and -F, and CbrA-C genes from all *Staphylococcus aureus* strains are included in the present invention.

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion. In case of conflict between Table 1 and either the nucleic acid sequence of the clones listed in Table 1 or the amino acid sequence of the protein expressed by the clones listed in Table 1, the clones listed in Table 1 are controlling. By "nucleotide sequence" of a nucleic acid molecule or polynucleotide is intended to mean either a DNA or RNA sequence. Using the information provided herein, such as the nucleotide sequence in Table 1, a nucleic acid molecule of the present invention encoding a *S. aureus* polypeptide may be obtained using standard cloning and screening procedures, such as those for cloning DNAs using genomic DNA as starting material. See, e.g., Sambrook et al. MOLECULAR CLONING: A LABORATORY MANUAL (Cold Spring Harbor, N.Y. 2nd ed. 1989); Ausubel et al., CURRENT PROTOCOLS IN MOLECULAR BIOLOGY (John Wiley and Sons, N.Y. 1989).

TABLE 1

Nucleotide and Amino Acid Sequences of 11 *S. aureus* Genes.

femX nucleotide sequence
clones BTEFS71 and BTEJE39
TGGAAAATTAATGAAGTTCCAAAGTTTAGATCAAAACTGGAATAATGGTGGAT (SEQ ID NO:1)

GGCGTAAAGCAGAGGTTGCACATAAAGTTGTTCATAATTATGAAAATGATATG

ATTTTTATTAGACCATTTAAAAAAGCATAATTTAAATCGAAGGCAGGACATTG

AAATATGAAATTTTCAACTTTAAGTGAAGAAGAATTTACCAACTACACCAAAA

AGCACTTCAAACATTATACGCAGTCTATAGAATTATATAATTATAGAAATAAA

TABLE 1-continued

Nucleotide and Amino Acid Sequences of 11 S. aureus Genes.

```
ATAAATCATGAAGCACATATTGTGGGAGTGAAGAATGATAAAAATGAAGTTA

TAGCTGCATGTTTATTAACAGAGGCACGAATTTTTAAATTCTACAAATATTTCT

ACTCTCATAGAGGTCCTTTACTTGATTATTTCGATGCTAAATTAGTTTGTTACT

TTTTTAAAGAATTATCTAAATTCATTTATAAAAATAGAGGAGTATTTATTCTTG

TTGATCCATATTTAATAGAGAATTTAAGAGATGCAAATGGTAGGATAATAAAG

AATTATAATAATTCAGTGATAGTAAAGATGCTAGGGAAAATTGGGTATCTCCA

TCAAGGTTATACAACAGGATATTCAAATAAAAGTCAAATTAGGTGGATTTCTG

TATTGGATTTAAAAGATAAAGATGAGAATCAACTTTTAAAAGAAATGGAATAC

CAAACTAGAAGAAATATAAAAAAGACTATTGAGATTGGTGTTAAGGTTGAAG

ATTTATCTATTGAAGAAACAAATCGATTTTATAAATTGTTTCAAATGGCTGAA

GAAAAACATGGTTTTCATTTCATGAATGAAGATTATTTTAAACGAATGCAAGA

AATATATAAAGATAAGGCAATGTTAAAGATAGCTTGTATAAATCTTAATGAAT

ATCAAGATAAATTAAAAATACAATTATTGAAAATCGAAAATGAAATGATGAC

TGTGAACAGAGCATTAAATGAAAATCCAAATTCTAAAAAAAATAAATCAAAA

TTAAATCAGTTAAATATGCAATTATCTAGTATTAATAATAGAATTAGTAAAAC

CGAAGAACTAATATTTGAAGATGGACCTGTTTTGGATTTAGCTGCTGCTTTATT

TATATGTACTGATGATGAAGTTTATTATCTATCAAGTGGATCAAATCCGAAAT

ATAATCAGTATATGGGTGCATATCATCTACAATGGCATATGATAAAATATGCA

AAATCACATAATATTAATAGGTATAATTTTTATGGAATAACAGGCGTCTTTAG

TAATGAGGCGGATGATTTTGGTGTTCAACAATTTAAAAAGGGTTTTAATGCAC

ATGTTGAAGAATTAATTGGTGATTTCATCAAACCAGTAAGACCAATTCTATAT

AAATTTGCAAAACTTATTTATAAGGTTTAATTATAAAGTATGTTGGAAATTGA

AATTTTAAATTCTTTCCAACATACTTTTCACTTTTTAAG
``` femX amino acid sequence
clones BTEFS71 and BTEJE39
MKFSTLSEEEFTNYTKKHFKHYTQSIELYNYRNKINHEAHIVGVKNDKNEVIAACL    (SEQ ID NO:2)

LTEARIFKFYKYFYSHRGPLLDYFDAKLVCYFFKELSKFIYKNRGVFILVDPYLIEN

LRDANGRIIKNYNNSVIVKMLGKIGYLHQGYTTGYSNKSQIRWISVLDLKDKDEN

QLLKEMEYQTRRNIKKTIEIGVKVEDLSIEETNRFYKLFQMAEEKHGFHFMNEDYF

KRMQEIYKDKAMLKIACINLNEYQDKLKIQLLKIENEMMTVNRALNENPNSKKNK

SKLNQLNMQLSSINNRISKTEELIFEDGPVLDLAAALFICTDDEVYYLSSGSNPKYN

QYMGAYHLQWHMIKYAKSHNINRYNFYGITGVFSNEADDFGVQQFKKGFNAHV

EELIGDFIKPVRPILYKFAKLIYKV furA nucleotide sequence
clone: BTEJQ50
TCTCCGGGTGGTGAaATTGTAGTTCTACTTGTTATTTTACTTATGATTACAATGG    (SEQ ID NO:3)

CTTATCAGAAAATGCGAATGAAGTTTAAAAAGGGAGCTAATATCAATGAATA

CAAATGATGCTATTAAAATTTTAAAAGAGAACGGTTTAAAATATACAGATAAA

CGTAAAGATATGTTAGATATTTTTGTCGAAGAAGATAAGTATATAAACGCAAA

GTATATACAACAAGTTATGGATGAAAATTATCCTGGAATTTCATTCGACACAA

TABLE 1-continued

Nucleotide and Amino Acid Sequences of 11 S. aureus Genes.

TATATAGAAACCTGCACTTATTTAAAGATTTAGGAATTATTGAAAATACAGAA

CTTGATGGTGAAATGAAGTTTAGAATCGCTTGTACAAACCATCATCATCATCA

TTTTATCTGTGAAAAGTGTGGAGATACAAAGGTAATAGATTATTGTCCAATAG

ATCAGATAAAATTATCACTACCTGGTGTTAATATTCACAAACACAAACTTGAA

GTTTATGGTGTATGTGAGTCTTGCCAAGATTAATATAAAGAAATGAGATTTAT

GCACATTTGGTCCGATGTATGCATAAATCT furA amino acid sequence
clone: BTEJQ50
MNTNDAIKILKENGLKYTDKRKDMLDIFVEEDKYINAKYIQQVMDENYPGISFDTI     (SEQ ID NO:4)

YRNLHLFKDLGIIENTELDGEMKFRIACTNHHHHHFICEKCGDTKVIDYCPIDQIKL

SLPGVNIHKHKLEVYGVCESCQD furB nucleotide sequence
clone: BTALE70
TTAAATGAAATCATCATGTAAATATTGACACGCGCGCAATACTACAGTTATAT     (SEQ ID NO:5)

TTATAGTAAGTAATAATAATTATTATATAAGAAAGATGGTGATATAGATGAGT

GTTGAAATAGAATCAATTGAACATGAACTAGAAGAATCAATTGCATCATTGCG

ACAAGCAGGCGTAAGAATTACACCTCAAAGACAAGCAATATTACGTTATTTAA

TTTCTTCACATACTCATCCAACAGCTGATGAAATTTATCAAGCACTTTCACCTG

ATTTTCCAAATATAAGTGTTGCGACAATATATAATAACTTAAGAGTGTTTAAA

GATATTGGAATTGTAAAAGAATTAACATATGGAGACTCATCAAGTCGATTCGA

CTTTAATACACATAATCATTATCATATTATATGTGAACAATGTGGTAAGATTGT

TGATTTTCAATATCCACAGTTAAATGAAATTGAAAGATTAGCTCAGCATATGA

CTGACTTTGACGTAACACATCATCGAATGGAAATTTATGGAGTTTGTAAAGAA

TGCCAAGATAAATAATTTAACTTTGGTAGTATGACAAATTAAAAAAGCGTTAC

T furB amino acid sequence
clone: BTALE70
MSVEIESIEHELEESIASLRQAGVRITPQRQAILRYLISSHTHPTADEIYQALSPDFPNI     (SEQ ID NO:6)

SVATTYNNLRVFKDIGIVKELTYGDSSSRFDFNTHNHYHIICEQCGKIVDFQYPQLN

EIERLAQHMTDFDVTHHRMEIYGVCKECQDK furC nucleotide sequence
clones: BTEBP80 and BTEFD68
TGAGAAAAGCTTGCATTTTATTGAGAAAACTGTTAGTTTTAATTGTAAAGTTTG     (SEQ ID NO:7)

AAATAATTTGTAATGATTTTAATTATTAGTAGGGGAGTGGACATCGTTGGAAG

AACGATTAAATCGCGTTAAGCAACAATTACAACAATCATCATATAAGCTAACG

CCACAACGCGAAGCTACTGTTAGAGTTCTAATTGAAAATGAAAAAGATCATCT

AAGTGCTGAAGACGTATATCTGAAAGTAAAAGATAAAGCGCCTGAAATTGGC

TTGGCGACAGTATACAGAACGTTAGAGTTGTTAGCTGAACTAAAAGTTGTCGA

CAAAATTAACTTTGGTGATGGCGTCGCTCGTTTTGATTTAAGAAAAGAAGGCG

CAAAACATTTCCACCATCATTTAGTATGTATGGAATGTGGTCGTGTAGATGAA

ATCGATGAAGATTTGTTACCAGAAGTTGAAAATCGAGTTGAAAATGAGTTCAA

TTTTAAAATTTTAGATCATCGTTTAACTTTCCATGGTGTGTGTGAAACGTGCCA

AGCTAAAGGTAAAGGATAGTAAATTGCGTAGGTTAAATTAACCTTCGCTTTTT

TABLE 1-continued

Nucleotide and Amino Acid Sequences of 11 S. aureus Genes.

TTAGAGGTGTGGTTAT furC amino acid sequence
clones: BTEBP80 and BTEFD68
LEELNRVKQQLQQSSYKLTPQREATVRVLIENEKDHLSAEDVYLKVKDKAPEIG     (SEQ ID NO:8)

LATVYRTLELLAELKVVDKINFGDGVARFDLRKEGAKHFHHHLVCMECGRVDEI

DEDLLPEVENRVENEFNFKILDHRLTFHGVCETCQAKGKG fmtB nucleotide sequence
clone: BTEDA22 and BTEDV18
GTAAATATACCTCTTTAATTAATTTATTCAATAGAACTGGTATAATAAAATAA     (SEQ ID NO:9)

ATCTCATTAGGCACTTAAGTAAATTTAACATATAAAAAGGAACGTTTATGACT

ACTAAAAAACTGTATTTTCTATCCATTTCTATTATCATTTTAGTCGCCATTTCA

ATTGCTATATATATAACATTAAATAGCAATACGAAGACACGGTTAACCAATGA

TTCGCAACAACAAATAGATACAATTATCGAGCATGATTTACAAAAGGGACAC

ATTCCTGGAGCATCAATTTTAATAGTAAAAAATGGCAAAGTTTTTTTAAATAA

AGGTTATGGTTATCAAGATGTTGATAAAAAAGTCAAAGCTTCTCCCACAACAA

AGTATGAAATTGCTTCTAATACGAAAGCTTTCACAGGTCTTGCAATTTTAAAA

TTAGCTCAAGAAGGTCGATTAAACTTAAATGATGCCGTATCCAAACATGTGCC

TCATTTTAAAATGAACTATAATGGTCAAAATGAAACTATTACGATTAAGCAAC

TTTTGGCTCAAACAAGTGGTATACCTAGTGATATTACAAGCGAAGATTCTGTG

ACAAGCAAAAATAATCGTTTAAATGATGTAACCCATGCAATTATGGGTGATGA

ATTACATCATAAGCCCGGAGAAGAATTTGAATACTCAAATATGAACTATGATT

TATTAGGTTTAATTATCCAAAACGTTACGAAGCAATCCTATACAAAATATATT

ACAAATTCATGGCTCAAGCCTTTGCATATGACACATACATCATTCAAACAAAC

CAATTACAAATCAAAACATGATGCTATTGGCTATGAATTACAAGGTTCGACAC

CTGTCGTCTCTAAACCTGAATTTAACCTTTGGGATACACCATCAGCATATATGA

TGACATCAACTGAAGATTTGGAACATTGGATAAAATTCCAACTTAATCCACCT

GATAAATACAAATCATTAGTTCAACAATCACATAAAAATTTATCTTCAACAAT

TGGTGAACCTAATGCCAATGCATATGCTTCCGGCTGGTTTACCAATAATGATG

AACATTTAGTGTTTCATTCAGGAACGCTAGATAACTTTTCATCATTTATTTTAC

TAAATCCAAAACAAAATTATGGAATTGTTGTACTTGCAAATCTAAATTCGGAA

TATGTACCCAAATTAGTTGAGCATCTTAATACACAAATTGTAAATCACAAGCG

ATATTCGACGGTTGCGTCTATGCTCAATCAATATAAAGATCAATTTAATATTGT

TACCGTTTTGATGACAACACTTATTTTATTAGCATTTATATTCTCAGCTTATCGT

GCTTGGCAAATGCGCCATGGTCAAATTCTTTTGCGTAGATCAAAACGGATTGC

TGTATTGAGTTGGTTATCATTATGTATATGTATCGCTTTAGCGCTCATATTATA

TGCATTACCATATCTCATTCTCGGTAGCAATAATTGGTCTTTTGTACTGACTTG

GCTACCAATAGAAATTAAATTAGCACTAATCACAACATTAATTGCATTATTCA

GTACATTAATTGTAATTCTGTTATTCCTTCATAATGCAGGAACGAAGACATAA

TAAAAAAGACTTGTTCGAGCCGTGCGTTTGATAATATATCATCCACGATT fmtB amino acid sequence
clone: BTEDA22 and BTEDV18

TABLE 1-continued

Nucleotide and Amino Acid Sequences of 11 *S. aureus* Genes.

MTTKKLYFLSISIIILVAISIAIYTTLNSNTKTRLTNDSQQQIDTIIEHDLQKGHIPGASIL    (SEQ ID NO:10)

IVKNGKVFLNKGYGYQDVDKKVKASPTTKYEIASNTKAFTGLAILKLAQEGRLNL

NDAVSKHVPHFKMNYNGQNETITIKQLLAQTSGIPSDITSEDSVTSKNNRLNDVTH

AIMGDELHHKPGEEFEYSNMNYDLLGLIIQNVTKQSYTKYITNSWLKPLHMTHTSF

KQTNYKSKHDAIGYELQGSTPVVSKPEFNLWDTPSAYMMTSTEDLEHWIKFQLNP

PDKYKSLVQQSHKNLSSTIGEPNANAYASGWFTNNDEHLVFHSGTLDNFSSFILLN

PKQNYGIVVLANLNSEYVPKLVEHLNTQIVNHKRYSTVASMLNQYKDQFNIVTVL

MTTLILLAFIFSAYRAWQMRHGQILLRRSKRIAVLSWLSLCICIALALILYALPYLIL

GSNNWSFVLTWLPIEIKLALITTLIALFSTLIVILLFLHTKITKT pbpF nucleotide sequence
clones: BTEBG73 AND BTAJO70
CTCTTAAATGAGACCGTTATTTTTTGTCAAAAAGATAGAAATAATTTCTAAAT    (SEQ ID NO:11)

TCATATATGATTTAAAGTGAAAGACTTTGAATAGAGGTAGGTAGTTTTGTTAA

AAAGACTAAAAGAAAAATCAAATGATGAAATCGTTCAAAATACCATTAACAA

GAGAATTAACTTTATATTTGGTGTGATTGTATTTATTTTTGCAGTACTAGTACT

ACGTTTAGGTTATTTACAAATCGCACAAGGCTCACATTATAAACAAATTATAA

AAAATGATGAAAACATTACAGTGAATGAGTCTGTGCCAAGAGGTCGTATTTTA

GACAGAAATGGGAAGTTTTAGTTGATAATGCTTCTAAAATGGCTATTACATA

TACTAGGGGTCGAAAACAACACAATCGGAAATGTTGGATACGGCTGAAAAG

TTATCAAAGCTAATCAAGATGGATACTAAGAAAATTACAGAACGTGATAAGA

AAGATTTCTGGATTCAGTTGCATCCTAAAAAAGCAAAAGCAATGATGACAAA

AGAACAAGCTATGTTAGCAGATGGAAGTATTAAACAAGATCAATATGATAAA

CAACTGTTATCGAAAATCGGAAAATCACAATTAGATGAATTGTCTTCTAAAGA

TTTACAAGTTTTAGCTATTTTTCGAGAGATGAATGCAGGAACAGTTTTAGATCC

ACAAATGATAAAAAATGAAGATGTCAGTGAAAAAGAGTATGCAGCAGTTTCT

CAGCAACTTTCCAAATTACCAGGTGTTAACACGTCTATGGATTGGGATAGAAA

ATATCCATATGGCGATACTTTAAGAGGTATATTCGGAGATGTATCGACACCTG

CTGAAGGTATTCCAAAAGAATTGACAGAACATTACTTATCCAAAGGATATTCA

CGCAATGATCGTGTTGGAAAATCTTACCTAGAATATCAATATGAAGATGTATT

GCGTGGTAAGAAGAAAGAAATGAAATACACAACGGACAAATCTGGTAAAGTT

ACATCTTCAGAAGTGTTAAATCCTGGCGCTCGCGGTCAAGATTTGAAATTAAC

GATCGATATAGATCTTCAAAAAGAAGTAGAAGCATTATTAGATAAACAAATT

AAGAAGCTTCGCAGTCAAGGTGCCAAAGATATGGATAATGCAATGATGGTTG

TACAAAATCCTAAAAATGGAGACATTCTTGCGCTTGCCGGAAAGCAGATTAAT

AAGAGTGGTAAAATGACTGATTATGACATTGGTACGTTTACTTCTCAATTTGC

GGTTGGATCTTCTGTAAAAGGTGGAACATTATTAGCCGGTTATCAGAATAAAG

CTATCAAAGTTGGAGAAACAATGGTCGATGAACCATTACATTTCCAAGGTGGT

TTGACAAAACGATCATACTTCAATAAAAACGGGCATGTAACTATTAATGATAA

GCAAGCTTTGATGCATTCATCAAACGTATATATGTTTAAAACAGCATTAAAAT

TAGCGGGAGACCCTTATTATTCTGGTATGGCTTTACCTTCAGACATAAGTTCAC

TABLE 1-continued

Nucleotide and Amino Acid Sequences of 11 S. aureus Genes.

CTGCCCAAAAGCTAAGAAGAGGATTAAATCAAGTAGGCTTAGGTGTGAAAAC

AGGGATAGATTTACCAAATGAAACAAGAGGTCAAATCGAACCATTAACAAAT

AATCCAGGTAATTATCTAGATTTATCAATTGGTCAATATGATACCTATACACC

ATTACAATTATCACAATATGTTTCAACTATAGCGAATGATGGTTATAGAATAC

AGCCACACATTGGATTAACGATTCATGAATCAACTAATAAAGATGAGGTTGGT

CCACTCAAGAAGAAAATTAATGGCACTGTCTTGAACAAGGTTAATAATACTGA

AAAGGAAATCAAACAAATTCAAGAAGGATTCAAAATGGCATTTAATGATAAA

GATGGTACTGGATATGTTAGTTTTAAAGATACAGTAGTACCTACTGCTGGTAA

AACGGGTACCGCAGAAGTGTTCCAAAACGGAGAGCCAAGAGTTAACTCTACT

TATATAGGATACGCGCCAATTGATGATCCAAAATTAGCGTTTTCAATTGTATA

TACAAATCAGCCTGTACCACCACCATGGTTAACAGGTGGAGACTTAGGTAGAG

ATGTAATTAACTACTACTTTAAGCAGTTAGGTAAAGATGATAAAAATAAAGAC

AAAGACAAATAAAATTTAACCTGACGATTGTGTAGCGCATGGTTGTAAAATTT

TAACTTTGC pbpF amino acid sequence
clones: BTEBG73 AND BTAJO70
LLKRLKEKSNDEIVQNTINKRINFIFGVIVFIFAVLVLRLGYLQIAQGSHYKQIIKNDE          (SEQ ID NO:12)

NITVNESVPRGRILDRNGKVLVDNASKMAITYTRGRKTTQSEMLDTAEKLSKLIK

MDTKKITERDKKDFWIQLHPKKAKAMMTKEQAMLADGSIKQDQYDKQLLSKIG

KSQLDELSSKDLQVLAIFREMNAGTVLDPQMIKNEDVSEKEYAAVSQQLSKLPGV

NTSMDWDRKYPYGDTLRGIFGDVSTPAEGIPKELTEHYLSKGYSRNDRVGKSYLE

YQYEDVLRGKKKEMKYTTDKSGKVTSSEVLNPGARGQDLKLTIDIDLQKEVEALL

DKQIKKLRSQGAKDMDNAMMVVQNPKNGDILALAGKQINKSGKMTDYDIGTFTS

QFAVGSSVKGGTLLAGYQNKAIKVGETMVDEPLHFQGGLTKRSYFNKNGHVTIN

DKQALMHSSNVYMFKTALKLAGDPYYSGMALPSDISSPAQKLRRGLNQVGLGVK

TGIDLPNETRGQIEPLTNNPGNYLDLSIGQYDTYTPLQLSQYVSTIANDGYRIQPHIG

LTIHESTNKDEVGPLKKKINGTVLNKVNNTEKEIKQIQEGFKMAFNDKDGTYVS

FKDTVVPTAGKTGTAEVFQNGEPRVNSTYIGYAPIDDPKLAFSIVYTNQPVPPPWL

TGGDLGRDVINYYFKQLGKDDKNKDKDK pbpG nucleotide sequence
clones: BTEBU53 AND BTEFB55
TCCTATTCCTTATGCATTTCCCCTAATTATAATTAACGTTAAAATAAAAGTCAA          (SEQ ID NO:13)

ATTGCCTTAAATATGGTATACTATAACGTAATTTAGGAGGTTAAAGATGACGA

ATCAAGACAACAATCATCAATTGAATCATCGTATATATCATTTTGAAAAGATA

TATAAAGCTATCAAACATGTCATTGTTTACATATTTATGATTTTCATTGCCATC

GTTGCTATCGCTGTGATTGCGATGTCTTTATATTTTCATCATTTAACTAAAACG

TCCGACTCATTATCAGATGATGCTTTAATAAAAAAAGTTCGACAAATACCTGG

CGATGAATTATTAGATCATAATAACAAAAATTTATTATATGAGTATAACCATT

CTCAAAACTCACTCATTATAGGCCCTAAAACATCAAGTCCAAATGTCATTAAA

GCATTAACGTCATCTGAAGACACTTTATTTTATAAACATGATGGCATCTTACCA

TABLE 1-continued

Nucleotide and Amino Acid Sequences of 11 S. aureus Genes.

```
AAGGCGATTTTAAGAGCAATGATACAAGATATTTTTAATACTGATCAAAGTTC

AGGTGGTAGCACAATTACACAACAACTTGTTAAAAATCAAGTTCTTACCAACG

AAAAAACATATAGTAGAAAAGCAAATGAACTTCGCCTAGCAATTAGATTAGA

ACACCTACTCTCAAAAGATGAAATTATATATACATATTTAAATATAGTTCCCTT

CGGTAGAGATTATAATGGCGCTAATATTTCCGGAATTGCATCCGCTTCATATA

GTCTATTTGGTATTCCACCAAAAGATTTATCAATTGCACAATCTGCATACCTTA

TCGGTTTGTTGCAAAGCCCATATGGCTATACACCCTACGAAAAGATGGAACG

TTAAAATCGGATAAAGATTTGAAATATAGTATTCAAAGACAACATTATGTATT

AAAGCGTATGTTAATCGAAGATCAAATCACTGAAAAAGAATACAACGACGCA

TTAAAATATGATATTAAATCACATTTGTTAAATCGAAAAAAGCGTTAATTGAT

GCTCACTTTTTAAAGTAACCACAACAATGAATCCAAATATTAAAA
``` pbpG amino acid sequence
clones: BTEBU53 AND BTEFB55

```
MTNQDNNHQLNHRIYHFEKIYKAIKHVIVYIFMIFIAIVAIAVIAMSLYFHHLTKTSD        (SEQ ID NO:14)

SLSDDALIKKVRQIPGDELLDHNNKNLLYEYNHSQNSLIIGPKTSSPNVIKALTSSED

TLFYKHDGILPKAILRAMIQDIFNTDQSSGGSTITQQLVKNQVLTNEKTYSRKANEL

RLAIRLEHLLSKDEIIYTYLNIVPFGRDYNGANISGIASASYSLFGIPPKDLSIAQSAY

LIGLLQSPYGYTPYEKDGTLKSDKDLKYSIQRQHYVLKRMLIEDQITEKEYNDALK

YDIKSHLLNRKKR
``` cbrA nucleotide sequence
clones: BTACA44 and BTAGJ54

```
TAGTCAATGAATAAAGTAATTAAAATGCTTGTTGTTACGCTTGCTTTCCTACTT        (SEQ ID NO:15)

GTTTTAGCAGGATGTAGTGGGAATTCAAATAAACAATCATCTGATAACAAAGA

TAAGGAAACAACTTCAATTAAACATGCAATGGGTACAACTGAAATTAAAGGG

AAACCAAAGCGTGTTGTTACGCTATATCAAGGTGCCACTGACGTCGCTGTATC

TTTAGGTGTTAAACCTGTAGGTGCTGTAGAATCATGGACACAAAAACCGAAAT

TCGAATACATAAAAAATGATTTAAAAGATACTAAGATTGTAGGTCAAGAACCT

GCACCTAACTTAGAGGAAATCTCTAAATTAAAACCGGACTTAATTGTCGCGTC

AAAAGTTAGAAATGAAAAAGTTTACGATCAATTATCTAAAATCGCACCAACA

GTTTCTACTGATACAGTTTTCAAATTCAAAGATACAACTAAGTTAATGGGGAA

AGCTTTAGGGAAAGAAAAAGAAGCTGAAGATTTACTTAAAAAGTACGATGAT

AAAGTAGCTGCATTCCAAAAAGATGCAAAAGCAAAGTATAAAGATGCATGGC

CATTGAAAGCTTCAGTTGTTAACTTCCGTGCTGATCATACAAGAATTTATGCTG

GTGGATATGCTGGTGAAATCTTAAATGATTTAGGATTCAAACGTAATAAAGAC

TTACAAAAACAAGTTGATAATGGTAAAGATATTATCCAACTTACATCTAAAGA

AAGCATTCCATTAATGAACGCTGATCATATTTTTGTAGTAAAATCAGATCCAA

ATGCGAAAGATGCTGCATTAGTTAAAAAGACTGAAAGCGAATGGACTTCAAG

TAAAGAGTGGAAAAATTTAGACGCAGTTAAAAACAACCAAGTATCTGATGAT

TTAGATGAAATCACTTGGAACTTAGCTGGCGGATATAAATCTTCATTAAAACT

TATTGACGATTTATATGAAAAGTTAAATATTGAAAAACAATCAAATAA
``` cbrA amino acid sequence

TABLE 1-continued

Nucleotide and Amino Acid Sequences of 11 S. aureus Genes.

clones: BTACA44 and BTAGJ54
MNKVIKMLVVTLAFLLVLAGCSGNSNKQSSDNKDKETTSIKHAMGTTEIKGKPKR (SEQ ID NO:16)

VVTLYQGATDVAVSLGVKPVGAVESWTQKPKFEYIKNDLKDTKIVGQEPAPNLE

EISKLKPDLIVASKVRNEKVYDQLSKIAPTVSTDTVFKFKDTTKLMGKALGKEKEA

EDLLKKYDDKVAAFQKDAKAKYKDAWPLKASVVNFRADHTRIYAGGYAGEILN

DLGFKRNKDLQKQVDNGKDIIQLTSKESIPLMNADHIFVVKSDPNAKDAALVKKT

ESEWTSSKEWKNLDAVKNNQVSDDLDEITWNLAGGYKSSLKLIDDLYEKLNIEKQ

SK cbrB nucleotide sequence
clones: BTACA44 and BTAGJ54
TAATTAAGGAGTTTTACGATGCTACTTAAACCAAAATACCAAATCGTTATTGC (SEQ ID NO:17)

TGGTTTATGTCTTGCAATAGTAGCTATCTTAAGTTTAATGATTGGAAATACGCT

TGTGTCACCAGGTACGGTGATACAGGCGTTATTCAACTTTGATAGTGAAAACG

ATTTACATGATGTTGTCACTGGTGCACGGGGCGTCGAGAACAATCATTGCGTTA

TTGACTGGTGCTGCCCTTGCTGTCTCAGGTTTGTTGATGCAAGCACTTACACGA

AACCCAATAGCCTCACCAGGGCTTTTCGGTGTCAATGCAGGCGCAGTATTTTT

TGTCATTTTTAGTATTACATTTATCCAAATTCAATCTTTTAAAATGATTGTAGTT

ATTGCATTTTTGGGGGCTATTGTTGTTACTGTATTAGTTGTTGCACTAGGTATG

TTTAGACAAACACTATTCTCACCTCACCGTGTCATTTTGGCAGGTGCTGCGATT

GCGATGCTATTTACAGCCTTTACTCAAGGCATACTTATTATGAACGAAACAGA

CTTACAAGGCCTATTATTTTGGTTAAGTGGCTCCGTTTCATTACGTAATATTTG

GGATATCCCATGGATTATTCCGCTTGTATTGATACTTATTTTAATTGCATTTAG

CATGGCTGCACACATCAACATCTTGATGACAAGTGACGACATTGCAACCGGCC

TCGGTCAAAACATAAAATTAATCAAATGGATGATTATTATGCTCATCAGTATG

TTAGCCGGTATTTCGGTAGCCGTAGCTGGATCAATCGTCTTTGTGGGTCTTATC

GTACCGAATATTAGCAAACGATTATTACCACCAAACTATAAGTATTTAATTCC

TTTTACTGCATTAGCTGGAGCAATCCTAATGATCATTTCAGACATTGTTGCTCG

TATAATAATTAAGCCACTAGAGTTGCCTATCGGTGTCGTTACCGCTGTCATTGG

CGCTATTGTCTTAATCTATATTATGAAGAAAGGACGTCAACGCTTATGA cbrB amino acid sequences
clones: BTACA44 and BTAGJ54
MLLKPYQIVIAGLCLAIVAILSLMIGNTLVSPGTVIQALFNFDSENDLHDVVTGAR (SEQ ID NO:18)

ASRTIIALLTGAALAVSGLLMQALTRNPIASPGLFGVNAGAVFFVIFSITFIQIQSFKM

IVVIAFLGAIVVTVLVVALGMFRQTLFSPHRVILAGAAIAMLFTAFTQGILIMNETD

LQGLLFWLSGSVSLRNIWDIPWIIPLVILILIAFSMAAHINILMTSDDIATGLGQNIK

LIKWMIIMLISMLAGISVAVAGSIVFVGLIVPNISKRLLPPNYKYLIPFTALAGAILMII

SDIVARIIIKPLELPIGVVTAVIGAIVLIYIMKKGRQRL cbrC nucleotide sequence
clones: BTACA44 and BTAGJ54
TAAGCCACTAGAGTTGCCTATCGGTGTCGTTACCGCTGTCATTGGCGCTATTGT (SEQ ID NO:19)

CTTAATCTATATTATGAAGAAAGGACGTCAACGCTTATGACCGAAAAGATTAA

TAAAAAAGACAATTACCATCTCATCTTCGCGTTAATCTTTTTAGCCATCGTTTC

TABLE 1-continued

Nucleotide and Amino Acid Sequences of 11 S. aureus Genes.

AGTGGTAAGTATGATGATTGGTTCAAGCTTTATACCATTACAACGCGTACTGA

TGTACTTTATAAATCCAAATGACAGTATGGATCAATTCACTTTAGAAGTATTA

CGCTTACCTCGCATTACACTTGCGATTTTAGCAGGTGCCGCACTAGGAATGAG

TGGTTTAATGTTGCAAAATGTATTAAAAAATCCAATTGCCTCACCTGATATTAT

CGGTATCACAGGTGGTGCTAGCTTAAGTGCTGTTGTCTTTATTGCATTTTTCAG

CCATTTAACAATACATTTACTTCCACTATTTGCAGTATTAGGTGGCGCAGTTGC

AATGATGATACTATTAGTGTTTCAAACGAAAGGACAAATACGCCCGACAACA

CTCATAATCATCGGTATTTCGATGCAAACGTTGTTTATTGCGCTTGTCCAAGGA

TTACTCATTACAACGAAGCAATTATCTGCTGCCAAAGCTTATACATGGCTAGT

CGGAAGTCTTTACGGTGCTACGTTTAAAGATACAATCATTTTGGGTATGGTTAT

TTTAGCTGTTGTGCCGTTGTTATTTCTTGTTATACCAAAAATGAAAATATCTAT

ACTTGATGACCCTGTAGCGATTGGCTTAGGCTTACATGTACAACGTATGAAAC

TAATCCAATTAATCACTTCTACTATACTCGTATCTATGGCAATCAGTTTAGTAG

GTAACATTGGGTTTGTCGGTTTAATCGCACCACATATCGCGAAAACAATCGTT

CGCGGAAGTTATGCTAAAAAGTTACTAATGTCAGCAATGATTGGTGCCATATC

AATTGTTATTGCAGACTTAATTGGGCGTACCTTATTCTTGCCTAAAGAAGTGCC

AGCAGGTGTATTTATTGCTGCTTTTGGTGCCCCATTCTTCATATACTTATTATTA

ACCGTGAAAAAGTTATAA cbrC amino acid sequences
clones: BTACA44 and BTAGJ54
MTEKINKKDNYHLIFALIFLAIVSVVSMMIGSSFIPLQRVLMYFINPNDSMDQFTLE        (SEQ ID NO:20)

VLRLPRITLAILAGAALGMSGLMLQNVLKNPIASPDIIGITGGASLSAVVFIAFFSHL

TIHLLPLFAVLGGAVAMMILLVFQTKGQIRPTTLIIIGISMQTLFIALVQGLLITTKQL

SAAKAYTWLVGSLYGATFKDTIILGMVILAVVPLLFLVIIPRMKISILDDPVAIGLGL

HVQRMKLIQLITSTILVSMAISLVGNIGFVGLIAPHIAKTIVRGSYAKKLLMSAMIGA

ISIVIADLIGRTLFLPKEVPAGVFIAAFGAPFFIYLLLTVKKL enolase nucleotide sequence
clones: BTAAI44 and BTAGE12
TAATGACACTTATTTTTTGAAAATAATAGTAATATCATTTTGTTAAATGAAAGA        (SEQ ID NO:21)

ATAAAGCTATAATAATTATAGAATAACTATTTAAAGGAGATTATAAACATGCC

AATTATTACAGATGTTTACGCTCGCGAAGTCTTAGACTCTCGTGGTAACCCAA

CTGTTGAAGTAGAAGTATTAACTGAAAGTGGCGCATTTGGTCGTGCATTAGTA

CCATCAGGTGCTTCAACTGGTGAACACGAAGCTGTTGAATTACGTGATGGAGA

CAAATCACGTTATTTAGGTAAAGGTGTTACTAAAGCAGTTGAAAACGTTAATG

AAATCATCGCACCAGAAATTATTGAAGGTGAATTTTCAGTATTAGATCAAGTA

TCTATTGATAAAATGATGATCGCATTAGACGGTACTCCAAACAAAGGTAAATT

AGGTGCAAATGCTATTTTAGGTGTATCTATCGCAGTAGCACGTGCAGCAGCTG

ACTTATTAGGTCAACCACTTTACAAATATTTAGGTGGATTTAATGGTAAGCAG

TTACCAGTACCAATGATGAACATCGTTAATGGTGGTTCTCACTCAGATGCTCC

AATTGCATTCCAAGAATTCATGATTTTACCTGTAGGTGCTACAACGTTCAAAG

AATCATTACGTTGGGGTACTGAAATTTTCCACAACTTAAAATCAATTTTAAGC

TABLE 1-continued

Nucleotide and Amino Acid Sequences of 11 S. aureus Genes.

```
CAACGTGGTTTAGAAACTGCCGTAGGTGACGAAGGTGGTTTCGCTCCTAAATT

TGAAGGTACTGAAGATGCTGTTGAAACAATTATCCAAGCAATCGAAGCAGCT

GGTTACAAACCAGGTGAAGAAGTATTCTTAGGATTTGACTGTGCATCATCAGA

ATTCTATGAAAATGGTGTATATGACTACAGTAAGTTCGAAGGCGAACACGGTG

CAAAACGTACAGCTGCAGAACAAGTTGACTACTTAGAACAATTAGTAGACAA

ATATCCTATCATTACAATTGAAGACGGTATGGACGAAAACGACTGGGATGGTT

GGAAACAACTTACAGAACGTATCGGTGACCGTGTACAATTAGTAGGTGACGA

TTTATTCGTAACAAACACTGAAATTTTAGCAAAAGGTATTGAAAACGGAATTG

GTAACTCAATCTTAATTAAAGTTAACCAAATCGGTACATTAACTGAAACATTT

GATGCAATCGAAATGGCTCAAAAAGCTGGTTACACAGCAGTAGTTTCTCACCG

TTCAGGTGAAACAGAAGATACAACAATTGCTGATATTGCTGTTGCTACAAACG

CTGGTCAAATTAAAACTGGTTCATTATCACGTACTGACCGTATTGCTAAATAC

AATCAATTATTACGTATCGAAGATGAATTATTTGAAACTGCTAAATATGACGG

TATCAAATCATTCTATAACTTAGATAAATAATTTTCTTTATAATCAAATGCTGA

CATAATTTTAGTTGAGGATTATTATGACGG
``` enolase amino acid sequence
clones: BTAAI44 and BTAGE12
```
MPIITDVYAREVLDSRGNPTVEVEVLTESGAFGRALVPSGASTGEHEAVELRDGD    (SEQ ID NO:22)

KSRYLGKGVTKAVENVNEIIAPEIIEGEFSVLDQVSIDKMMIALDGTPNKGKLGAN

AILGVSIAVARAAADLLGQPLYKYLGGFNGKQLPVPMMNIVNGGSHSDAPIAFQE

FMILPVGATTFKESLRWGTEIFHNLKSIISQRGLETAVGDEGGFAPKFEGTEDAVE

TIIQAIEAAGYKPGEEVFLGFDCASSEFYENGVYDYSKFEGEHGAKRTAAEQVDYL

EQLVDKYPIITIEDGMDENDWDGWKQLTERIGDRVQLVGDDLFVTNTEILAKGIEN

GIGNSILIKVNQIGTLTETFDAIEMAQKAGYTAVVSHRSGETEDTTIADIAVATNAG

QIKTGSLSRTDRIAKYNQLLRIEDELFETAKYDGIKSFYNLDK
```

Illustrative of the invention, the nucleic acid molecule described in Table 1 was discovered in a DNA library derived from a S. aureus ISP3 genomic DNA.

Nucleic acid molecules of the present invention may be in the form of RNA, such as mRNA, or in the form of DNA, including, for instance, DNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" polynucleotide sequence is intended a nucleic acid molecule, DNA or RNA, which has been removed from its native environment. This includes segments of DNA comprising the S. aureus polynucleotides of the present invention isolated from the native chromosome. These fragments include both isolated fragments consisting only of S. aureus DNA and fragments comprising heterologous sequences such as vector sequences or other foreign DNA. For example, recombinant DNA molecules contained in a vector are considered isolated for the purposes of the present invention which may be partially or substantially purified. Further examples of isolated DNA molecules include recombinant DNA molecules introduced and maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically which may be partially or substantially purified. The term "isolated" does not refer to genomic or cDNA libraries, whole cell mRNA preparations, genomic DNA digests (including those gel separated by electrophoresis), sheared whole cell genomic DNA preparations or other compositions where the art demonstrates no distinguishing features of the polynucleotides sequences of the present invention.

In addition, isolated nucleic acid molecules of the invention include DNA molecules which comprise a sequence substantially different from those described above but which, due to the degeneracy of the genetic code, still encode a S. aureus polypeptides and peptides of the present invention (e.g. polypeptides of Table 1). That is, all possible DNA sequences that encode the S. aureus polypeptides of the present invention. This includes the genetic code and species-specific codon preferences known in the art. Thus, it would be routine for one skilled in the art to generate the degenerate variants described above, for instance, to optimize codon expression for a particular host (e.g., change codons in the bacteria mRNA to those preferred by a mammalian or other bacterial host such as *E. coli*).

The invention further provides isolated nucleic acid molecules having the nucleotide sequence shown in Table 1 or a nucleic acid molecule having a sequence complementary to one of the above sequences. Such isolated molecules, particularly DNA molecules, are useful as probes for gene mapping and for identifying *S. aureus* in a biological sample, for instance, by PCR or Northern blot analysis. In specific embodiments, the polynucleotides of the present invention are less than 300 kb, 200 kb, 100 kb, 50 kb, 10,kb, 7.5 kb, 5 kb, 2.5 kb, and 1 kb. In another embodiment, the polynucleotides comprising the coding sequence for polypeptides of the present The present invention is further directed to nucleic acid molecules encoding portions or fragments of the polynucleotide sequences described herein, e.g., shown in the Tables, sequence listing, or contained in the deposited clones. Uses for the polynucleotide fragments of the present invention include probes, primers, molecular weight, markers and for expressing the polypeptide fragments of the present invention. Fragments include portions of the polynucleotide sequences, at least 10 contiguous nucleotides in length selected from any two integers, one of which representing a 5' nucleotide position and a second of which representing a 3' nucleotide position, where the first, or 5' most, nucleotide for each disclosed polynucleotide sequence is position 1. That is, every combination of a 5' and 3' nucleotide position that a fragment at least 10 contiguous nucleotides in length could occupy is included in the invention as an individual specie. "At least" means a fragment may be 10 contiguous nucleotide bases in length or any integer between 10 and the length of an entire nucleotide sequence minus 1. Therefore, included in the invention are contiguous fragments specified by any 5' and 3' nucleotide base positions of a polynucleotide sequences wherein the contiguous fragment is any integer between 10 and the length of an entire nucleotide sequence minus 1. The polynucleotide fragments specified by 5' and 3' positions can be immediately envisaged using the above description and are therefore not individually listed solely for the purpose of not unnecessarily lengthening the specifications. Although it is particularly pointed out that each of the above described species are included in the present invention.

Further, the invention includes polynucleotides comprising sub-genuses of fragments specified by size, in nucleotides, rather than by nucleotide positions. The invention includes any fragment size, in contiguous nucleotides, selected from integers between 10 and the length of an entire nucleotide sequence minus 1 (where 1 is the first, or 5' most, nucleotide for each disclosed polynucleotide sequence). Preferred sizes of contiguous nucleotide fragments include 20 nucleotides, 30 nucleotides, 40 nucleotides, 50 nucleotides, 60 nucleotides, 70 nucleotides, 80 nucleotides, 90 nucleotides, 100 nucleotides, 125 nucleotides, 150 nucleotides, 175 nucleotides, 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 750 nucleotides, 800 nucleotides, 850 nucleotides, 900 nucleotides, 950 nucleotides, 1000 nucleotides. Other preferred sizes of contiguous polynucleotide fragments, which may be useful as diagnostic probes and primers, include fragments 50–300 nucleotides in length which include, as discussed above, fragment sizes representing each integer between 50–300. Larger fragments are also useful according to the present invention corresponding to most, if not all, of the polynucleotide sequences of the sequence listing or deposited clones. The preferred sizes are, of course, meant to exemplify not limit the present invention as all size fragments, representing any integer between 10 and the length of an entire nucleotide sequence minus 1 of the sequence listing or deposited clones, are included in the invention. Additional preferred nucleic acid fragments of the present invention include nucleic acid molecules encoding epitope-bearing portions of the polypeptides.

The polynucleotide fragments, specified in contiguous nucleotides, can be immediately envisaged using the above description and are therefore not individually listed solely for the purpose of not unnecessarily lengthening the specification.

The present invention also provides for the exclusion of any fragment, specified by 5' and 3' base positions or by size in nucleotide bases as described above for any nucleotide sequence of the sequence listing or deposited clones. Any number of fragments of nucleotide sequences specified by 5' and 3' base positions or by size in nucleotides, as described above, may be excluded from the present invention.

In another aspect, the invention provides an isolated nucleic acid molecule comprising a polynucleotide which hybridizes under stringent hybridization conditions to a portion of a polynucleotide in a nucleic acid molecules of the invention described above, for instance, nucleotide sequences of Table 1 or the *S. aureus* sequences of the plasmid clones listed in Table 1. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides bases, and more preferably at least about 20 nucleotides bases, still more preferably at least about 30 nucleotides bases, and even more preferably about 30–70 (e.g., 50) nucleotides bases of the reference polynucleotide. These are useful as diagnostic probes and primers as discussed above. By a portion of a polynucleotide of "at least 20 nucleotides bases in length," for example, is intended 20 or more contiguous nucleotides bases nucleotides from the nucleotide sequence of the reference polynucleotide (e.g., the nucleotide sequence as shown in Table 1). Portions of a polynucleotide which hybridizes to a nucleotide sequence in Table 1, which can be used as probes and primers, may also be precisely specified by 5' and 3' base positions or by size in nucleotide bases as described above or precisely excluded in the same manner.

The nucleic acid molecules of the present invention, which encode a *S. aureus* polypeptide, may include, but are not limited to, nucleic acid molecules encoding: the full length *S. aureus* polypeptide of Table 1, the full length polypeptide expressed by the plasmid clones listed in Table 1, and portions of the *S aureus* polypeptides of Table 1 and the polypeptides expressed by the plasmid clones listed in Table 1. Also included in the present invention are nucleic acids encoding the above full length sequences and further comprise additional sequences, such as those encoding an added secretory leader sequence, such as a pre-, or pro- or prepro-protein sequence. Further included in the present invention are nucleic acids encoding the above full length sequences and portions thereof and further comprise additional heterologous amino acid sequences encoded by nucleic acid sequences from a different source.

Also included in the present invention are nucleic acids encoding the above protein sequences together with additional, non-coding sequences, including for example, but not limited to non-coding 5' and 3' sequences. These sequences include transcribed, non-translated sequences that may play a role in transcription, and mRNA processing, for example, ribosome binding and stability of mRNA. Also included in the present invention are additional coding sequences which provide additional functionalities.

Thus, a nucleotide sequence encoding a polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. For instance, hexa-histidine provides for convenient purification of the fusion protein. See Gentz et al. (1989) Proc. Natl. Acad. Sci. 86:821–24. The "HA" tag is another peptide useful for purification which corresponds to an epitope derived from the influenza hemagglutinin protein. See Wilson et al. (1984) Cell 37:767. As discussed below, other such fusion proteins include the S. aureus fused to Fc at the N- or C-terminus.

Variant and Mutant Polynucleotides

The present invention further relates to variants of the nucleic acid molecules which encode portions, analogs or derivatives of a S. aureus polypeptides of Table 1, or encoded by the plasmid clones listed in Table 1, and variant polypeptides thereof including portions, analogs, and derivatives of the S. aureus polypeptides. Variants may occur naturally, such as a natural allelic variant. By an "allelic variant" is intended one of several alternate forms of a gene occupying a given locus on a chromosome of an organism. See, e.g., B. Lewin, Genes IV (1990). Non-naturally occurring variants may be produced using art-known mutagenesis techniques.

Such nucleic acid variants include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of a S. aureus protein of the present invention or portions thereof. Also especially preferred in this regard are conservative substitutions.

Such polypeptide variants include those produced by amino acid substitutions, deletions or additions. The substitutions, deletions, or additions may involve one or more residues. Alterations may produce conservative or non-conservative amino acid substitutions, deletions, or additions. Especially preferred among these are silent substitutions, additions and deletions, which do not alter the properties and activities of a S. aureus protein of the present invention or portions thereof. Also especially preferred in this regard are conservative substitutions.

The present invention also relates to recombinant vectors, which include the isolated nucleic acid molecules of the present invention, and to host cells containing the recombinant vectors, as well as to methods of making such vectors and host cells and for using them for production of S. aureus polypeptides or peptides by recombinant techniques.

The present application is directed to nucleic acid molecules at least 90%, 95%, 96%, 97%, 98% or 99% identical to a nucleic acid sequence shown in Table 1 or to the nucleic acid sequence of the plasmid clones listed in Table 1. The above nucleic acid sequences are included irrespective of whether they encode a polypeptide having S. aureus activity. This is because even where a particular nucleic acid molecule does not encode a polypeptide having S. aureus activity, one of skill in the art would still know how to use the nucleic acid molecule, for instance, as a hybridization probe. Uses of the nucleic acid molecules of the present invention that do not encode a polypeptide having S. aureus activity include, inter alia, isolating an S. aureus gene or allelic variants thereof from a DNA library, and detecting S. aureus mRNA expression samples, environmental samples, suspected of containing S. aureus by Northern Blot analysis.

Preferred, are nucleic acid molecules having sequences at least 90%, 95%, 96%, 97%, 98% or 99% identical to the nucleic acid sequence shown in Table 1 or to the nucleic acid sequence of the plasmid clones listed in Table 1, which do, in fact, encode a polypeptide having S. aureus protein activity By "a polypeptide having S. aureus activity" is intended polypeptides exhibiting activity similar, but not necessarily identical, to an activity of the S. aureus protein of the invention, as measured in a particular biological assay suitable for measuring activity of the specified protein.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the plasmid clones listed in Table 1 or a nucleic acid sequence shown in Table 1 will encode a polypeptide having S. aureus protein activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having S. aureus protein activity. This is because the skilled artisan is fully aware of amino acid substitutions that are either less likely or not likely to significantly effect protein function (e.g., replacing one aliphatic amino acid with a second aliphatic amino acid), as further described below.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the S. aureus polypeptide. In other words, to obtain a polynucleotide having a nucleotide sequence at least 95% identical to a reference nucleotide sequence, up to 5% of the nucleotides in the reference sequence may be deleted, inserted, or substituted with another nucleotide. The query sequence may be an entire sequence shown in Table 1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. See Brutlag et al. (1990) Comp. App. Biosci. 6:237–245. In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score.

For example, a 90 nucleotide subject sequence is aligned to a 100 nucleotide query sequence to determine percent identity. The deletions occur at the 5' end of the subject sequence and therefore, the FASTDB alignment does not show a matched/alignment of the first 10 nucleotides at 5' end. The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%. In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected for. No other manual corrections are to made for the purposes of the present invention.

Vectors and Host Cell

The present invention also relates to vectors which include the isolated DNA molecules of the present invention, host cells comprising the recombinant vectors, and the production of S. aureus polypeptides and peptides of the present invention expressed by the host cells.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate transacting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline, kanamycin, or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE9, pQE10 available from Qiagen; pBS vectors, Phagescript vectors, Bluescript vectors, pNH8A, pN16a, pNH18A, pNH46A available from Stratagene; pET series of vectors available from Novagen; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3, T5 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)).

Transcription of DNA encoding the polypeptides of the present invention by higher eukaryotes may be increased by inserting an enhancer sequence into the vector. Enhancers are cis-acting elements of DNA, usually about from 10 to 300 nucleotides that act to increase transcriptional activity of a promoter in a given host cell-type. Examples of enhancers include the SV40 enhancer, which is located on the late side of the replication origin at nucleotides 100 to 270, the cytomegalovirus early promoter enhancer, the polyoma enhancer on the late side of the replication origin, and adenovirus enhancers.

For secretion of the translated polypeptide into the lumen of the endoplasmic reticulum, into the periplasmic space or into the extracellular environment, appropriate secretion signals may be incorporated into the expressed polypeptide, for example, the amino acid sequence KDEL. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See Bennett, D. et al. (1995) J. Molec. Recogn. 8:52–58 and Johanson, K. et al. (1995) J. Biol. Chem. 270 (16): 9459–9471.

The *S. aureus* polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography and high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells.

Polypeptides and Fragments

The invention further provides an isolated *S. aureus* polypeptide having the amino acid sequence encoded by a plasmid clone listed in Table 1, or an amino acid sequence in Table 1, or a peptide or polypeptide comprising a portion of the above polypeptides.

Variant and Mutant Polypeptides

To improve or alter the characteristics of *S. aureus* polypeptides of the present invention, protein engineering may be employed. Recombinant DNA technology known to those skilled in the art can be used to create novel mutant proteins or muteins including single or multiple amino acid substitutions, deletions, additions, or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

It is known in the art that one or more amino acids may be deleted from the N-terminus or C-terminus without substantial loss of biological function. For instance, Ron et al. J. Biol. Chem., 268:2984–2988 (1993), reported modified KGF proteins that had heparin binding activity even if 3, 8, or 27 N-terminal amino acid residues were missing. Accordingly, the present invention provides polypeptides having one or more residues deleted from the amino terminus of the amino acid sequence of the *S. aureus* polypeptides shown in Table 1, and polynucleotides encoding such polypeptides.

Similarly, many examples of biologically functional C-terminal deletion muteins are known. For instance, Interferon gamma shows up to ten times higher activities by deleting 8–10 amino acid residues from the carboxy terminus of the protein See, e.g., Dobeli, et al. (1988) J. Biotechnology 7:199–216. Accordingly, the present invention provides polypeptides having one or more residues from the carboxy terminus of the amino acid sequence of the *S. aureus* polypeptides shown in Table 1. The invention also provides polypeptides having one or more amino acids deleted from both the amino and the carboxyl termini as described below.

The present invention is further directed to polynucleotide encoding portions or fragments of the amino acid sequences described herein as well as to portions or fragments of the isolated amino acid sequences described herein. Fragments include portions of the amino acid sequences of the Tables, sequence listing, and encoded by deposited cDNA clones, at least 7 contiguous amino acid in length, selected from any two integers, one of which representing a N-terminal position and another representing a C-terminal position. The first, or N-terminal most, codon of each polypeptide disclosed herein is position 1. Every combination of a N-terminal and C-terminal position that a fragment at least 7 contiguous amino acid residues in length could occupy, on any given amino acid sequence is included in the invention as an individual specie. At least means a fragment may be 7 contiguous amino acid residues in length or any integer between 7 and the number of residues in a full length amino acid sequence minus 1. Therefore, included in the invention are species of contiguous fragments specified by any N-terminal and C-terminal positions of amino acid sequence set forth in the sequence listing or encoded by the deposited cDNA clones, wherein the contiguous fragment is any integer between 7 and the number of residues in a full length sequence minus 1. The polypeptide fragments specified by N-terminal and C-terminal positions can be immediately envisaged using the above description and are therefore not individually listed solely for the purpose of not unnecessarily lengthening the specification. Although it is particularly pointed out that each of the above described species are included in the present invention.

Further, the invention includes polypeptides comprising sub-genuses of fragments specified by size, in amino acid residues, rather than by N-terminal and C-terminal positions. The invention includes any fragment size, in contiguous amino acid residues, selected from integers between 7 and the number of residues in a full length sequence minus 1. Preferred sizes of contiguous polypeptide fragments include at least 7 amino acid residues, at least 10 amino acid residues, at least 20 amino acid residues, at least 30 amino acid residues, at least 40 amino acid residues, at least 50 amino acid residues, at least 75 amino acid residues, at least 100 amino acid residues, at least 125 amino acid residues, at least 150 amino acid residues, at least 175 amino acid residues, at least 200 amino acid residues, at least 225 amino acid residues, at least 250 amino acid residues, at least 275 amino acid residues, at least 300 amino acid residues, at least 325 amino acid residues, at least 350 amino acid residues, at least 375 amino acid residues, at least 400 amino acid residues, at least 425 amino acid residues, and at least 450 amino acid residues. The preferred sizes are, of course, meant to exemplify, not limit, the present invention as all size fragments representing any integer between 7 and the number of residues in a full length sequence minus 1 are included in the invention.

The contiguous polypeptide fragments specified by size in amino acid residues of the present invention can be immediately envisaged using the above description and are therefore not individually listed solely for the purpose of not unnecessarily lengthening the specification.

The present invention also provides for the exclusion of any fragments specified by N-terminal and C-terminal positions or by size in amino acid residues as described above. Any number of fragments specified by N-terminal and C-terminal positions or by size in amino acid residues as described above.

It is particularly pointed out that the above fragments need not be active since they would be useful, for example, in immunoassays, in epitope mapping, epitope tagging, to generate antibodies to a particular portion of the polypeptide, as vaccines, and as molecular weight markers.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Other Mutants

In addition to N- and C-terminal deletion forms of the protein discussed above, it also will be recognized by one of ordinary skill in the art that some amino acid sequences of the S. aureus polypeptide can be varied without significant effect of the structure or function of the protein. If such differences in sequence are contemplated, it should be remembered that there will be critical areas on the protein which determine activity.

Thus, the invention further includes variations of the S. aureus polypeptides which show substantial S. aureus polypeptide activity or which include regions of S. aureus protein such as the protein portions discussed below. Such mutants include deletions, insertions, inversions, repeats, and type substitutions selected according to general rules known in the art so as to have little effect on activity. For example, guidance concerning how to make phenotypically silent amino acid substitutions is provided. There are two main approaches for studying the tolerance of an amino acid sequence to change. See, Bowie, J. U. et al. (1990), Science 247:1306–1310. The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions. The studies indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative, analog, or homolog of the polypeptide of Table 1, or that encoded by the plasmids listed in Table 1, may be: (i) one in which one or more of the amino acid residues are substituted with a conserved or non-conserved amino acid residue (preferably a conserved amino acid residue) and such substituted amino acid residue may or may not be one encoded by the genetic code: or (ii) one in which one or more of the amino acid residues includes a substituent group: or (iii) one in which the S. aureus polypeptide is fused with another compound, such as a compound to increase the half-life of the polypeptide (for example, polyethylene glycol): or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the S. aureus polypeptides of the present invention may include one or more amino acid substitutions, deletions, or additions, either from natural mutations or human manipulation. As indicated, changes are preferably of a minor nature, such as conservative amino acid substitutions that do not significantly affect the folding or activity of the protein (see Table 3).

TABLE 3

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the S. aureus proteins of the present invention that are essential for function can be identified by methods known in the art, such as site-directed mutagenesis or alanine-scanning mutagenesis. See, e.g., Cunningham et al. (1989) Science 244:1081–1085. The latter procedure introduces single alanine mutations at every residue in the molecule. The resulting mutant molecules are then tested for biological activity using assays appropriate for measuring the function of the particular protein.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic. See, e.g., Pinckard et al., (1967) Clin. Exp. Immunol. 2:331–340; Robbins, et al., (1987) Diabetes 36:838–845; Cleland, et al., (1993) Crit. Rev. Therapeutic Drug Carrier Systems 10:307–377.

The polypeptides of the present invention are preferably provided in an isolated form, and preferably are substantially purified. A recombinantly produced version of the S. aureus polypeptide can be substantially purified by the one-step method described by Smith et al. (1988) Gene 67:31–40. Polypeptides of the invention also can be purified from natural or recombinant sources using antibodies directed against the polypeptides of the invention in methods which are well known in the art of protein purification.

The invention further provides for isolated S. aureus polypeptides comprising an amino acid sequence selected from the group consisting of: (a) the amino acid sequence of a full-length S. aureus polypeptide having the complete amino acid sequence shown in Table 1; (b) the amino acid sequence of a full-length S. aureus polypeptide having the complete amino acid sequence shown in Table 1 excepting the N-terminal methionine; (c) the complete amino acid sequence encoded by the plasmids listed in Table 1; and (d) the complete amino acid sequence excepting the N-terminal methionine encoded by the plasmids listed in Table 1. The polypeptides of the present invention also include polypeptides having an amino acid sequence at least 80% identical, more preferably at least 90% identical, and still more preferably 95%, 96%, 97%, 98% or 99% identical to those described in (a), (b), (c), and (d) above.

Further polypeptides of the present invention include polypeptides which have at least 90% similarity, more preferably at least 95% similarity, and still more preferably at least 96%, 97%, 98% or 99% similarity to those described above.

A further embodiment of the invention relates to a polypeptide which comprises the amino acid sequence of a S. aureus polypeptide having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a S. aureus polypeptide, having at least one, but not more than 10, 9, 8, 7, 6, 5, 4, 3, 2 or 1 conservative amino acid substitutions.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by the plasmids listed in Table 1 can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., (1990) Comp. App. Biosci. 6:237–245. In a sequence alignment the query and subject sequences are both amino acid sequences. The result of said global sequence alignment is in percent identity. Preferred parameters used in a FASTDB amino acid alignment are: Matrix= PAM 0, k-tuple=2, Mismatch Penalty=1, Joining Penalty= 20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, the results, in percent identity, must be manually corrected. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not match/align with the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are to made for the purposes of the present invention.

The above polypeptide sequences are included irrespective of whether they have their normal biological activity. This is because even where a particular polypeptide molecule does not have biological activity, one of skill in the art would still know how to use the polypeptide, for instance, as a vaccine or to generate antibodies. Other uses of the polypeptides of the present invention that do not have S. aureus activity include, inter alia, as epitope tags, in epitope mapping, and as molecular weight markers on SDS-PAGE gels or on molecular sieve gel filtration columns using methods known to those of skill in the art.

As described below, the polypeptides of the present invention can also be used to raise polyclonal and monoclonal antibodies, which are useful in assays for detecting S. aureus protein expression or as agonists and antagonists capable of enhancing or inhibiting S. aureus protein function. Further, such polypeptides can be used in the yeast two-hybrid system to "capture" S. aureus protein binding proteins which are also candidate agonists and antagonists according to the present invention. See, e.g., Fields et al. (1989) Nature 340:245–246.

Epitope-Bearing Portions

In another aspect, the invention provides peptides and polypeptides comprising epitope-bearing portions of the polypeptides of the present invention. These epitopes are immunogenic or antigenic epitopes of the polypeptides of the present invention. An "immunogenic epitope" is defined as a part of a protein that elicits an antibody response in vivo when the whole polypeptide of the present invention, or fragment thereof, is the immunogen. On the other hand, a region of a polypeptide to which an antibody can bind is defined as an "antigenic determinant" or "antigenic epitope." The number of in vivo immunogenic epitopes of a protein generally is less than the number of antigenic epitopes. See, e.g., Geysen, et al. (1983) Proc. Natl. Acad. Sci. USA 81:3998–4002. However, antibodies can be made to any antigenic epitope, regardless of whether it is an immunogenic epitope, by using methods such as phage display. See e.g., Petersen G. et al. (1995) Mol. Gen. Genet. 249:425–431. Therefore, included in the present invention are both immunogenic epitopes and antigenic epitopes.

A list of exemplified amino acid sequences comprising immunogenic epitopes of the invention are described herein. It is pointed out that these descriptions only lists amino acid residues comprising epitopes predicted to have the highest degree of antigenicity using the algorithm of Jameson and Wolf, (1988) Comp. Appl. Biosci. 4:181–186 (said references incorporated by reference in their entireties). The Jameson-Wolf antigenic analysis was performed using the computer program PROTEAN, using default parameters (Version 3.11 for the Power MacIntosh, DNASTAR, Inc., 1228 South Park Street Madison, Wis.). Amino acid residues comprising other immunogenic epitopes may be routinely determined using algorithms similar to the Jameson-Wolf analysis or by in vivo testing for an antigenic response using methods known in the art. See, e.g., Geysen et al., supra; U.S. Pat. Nos. 4,708,781; 5,194,392; 4,433,092; and 5,480,971 (said references incorporated by reference in their entireties).

It is particularly pointed out that the described epitopic amino acid sequences comprise immunogenic epitopes. Table 2 lists only the critical residues of immunogenic epitopes determined by the Jameson-Wolf analysis. Thus, additional flanking residues on either the N-terminal, C-terminal, or both N- and C-terminal ends may be added to the sequences to generate an epitope-bearing polypeptide of the present invention. Therefore, the immunogenic epitopes may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences.

Polypeptides of the present invention comprising immunogenic or antigenic epitopes are at least 7 amino acids residues in length. "At least" means that a polypeptide of the present invention comprising an immunogenic or antigenic epitope may be 7 amino acid residues in length or any integer between 7 amino acids and the number of amino acid residues of the full length polypeptides of the invention. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. However, it is pointed out that each and every integer between 7 and the number of amino acid residues of the full length polypeptide are included in the present invention.

The immuno and antigenic epitope-bearing fragments may be specified by either the number of contiguous amino acid residues, as described above, or further specified by N-terminal and C-terminal positions of these fragments on the amino acid sequence of SEQ ID NO:2, 4, 6, 8, 10, 12, 14, 16, 18, 20, or 22. Every combination of a N-terminal and C-terminal position that a fragment of, for example, at least 7 or at least 15 contiguous amino acid residues in length could occupy on the amino acid sequence of SEQ ID NO:2 is included in the invention. Again, "at least 7 contiguous amino acid residues in length" means 7 amino acid residues in length or any integer between 7 amino acids and the number of amino acid residues of the full length polypeptide of the present invention. Specifically, each and every integer between 7 and the number of amino acid residues of the full length polypeptide are included in the present invention.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immuno assays, specifically for the polypeptides of the present invention using methods known in the art. See, e.g., Harlow et al., Antibodies: A Laboratory Manual, (Cold Spring Harbor Laboratory Press; 2nd Ed. 1988).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10–20 mgs of 248 individual and distinct 13 residue peptides representing single amino acid variants of a segment of the HA1 polypeptide, all of which were prepared and characterized (by ELISA-type binding studies) in less than four weeks (Houghten, R. A. Proc. Natl. Acad. Sci. USA 82:5131–5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al. (1985) Proc. Natl. Acad. Sci. 82:5131–5135 at 5134.

Epitope-bearing polypeptides of the present invention are used to induce antibodies according to methods well known in the art including, but not limited to, in vivo immunization, in vitro immunization, and phage display methods. See, e.g., Sutcliffe, et al., supra; Wilson, et al., supra, and Bittle, et al. (1985) J. Gen. Virol. 66:2347–2354. If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µgs of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al. (1988) Nature 331:84–86. Fusion proteins that have a disulfide-linked dimeric structure due to the IgG portion can also be more efficient in binding and neutralizing other molecules than monomeric polypeptides or fragments thereof alone. See, e.g., Fountoulakis et al. (1995) J. Biochem. 270:3958–3964. Nucleic acids encoding the above epitopes can also be recombined with a gene of interest as an epitope tag to aid in detection and purification of the expressed polypeptide.

TABLE 2

Residues Comprising Antigenic Epitope-Bearing Portion.

Fem X

About Asn-30 to about Lys-34; about Lys-45 to about Glu-50; about Asn-99 to about Gly-101; about Tyr-148 to about Gln-153; about Asn-181 to about Lys-184; about Asn-272 to about Ser-275; about Asn-278 to about Lys-281; about Arg-295 to about Lys-298; about Ser-331 to about Tyr-335; and about Lys-398 to about Val-400, all of SEQ ID NO:2.

fur A

About Asp-45 to about Tyr-48; and about Lys-96 to about Asp-99, all of SEQ ID NO:4.

fur B

About Pro-28 to about Arg-30; about Pro-44 to about Ala-46; about Asp-85 to about Arg-89; about Phe-90 to about Phe-92; about Gln-104 to about Gly-106; and about Cys-145 to about Lys-148, all of SEQ ID NO:6.

fur C

TABLE 2-continued

Residues Comprising Antigenic Epitope-Bearing Portion.

About Thr-20 to about Arg-23; about Phe-77 to about Gly-80; and about Ala-145 to about Ter-150, all of SEQ ID NO:8.

fmt B

About Ser-29 to about Gln-40; about Leu-51 to about His-55; about Gln-78 to about Lys-82; about Tyr-132 to about Gln-135; about Ile-155 to about Ser-157; about Val-161 to about Arg-167; about Lys-183 to about Glu-186; about Thr-232 to about Asp-239; about Lys-254 to about Glu-256; about Pro-284 to about Lys-289; about Ser-295 to about Leu-299; about Glu-305 to about Ala-308; about Asn-318 to about Glu-321; about Pro-341 to about Asn-344; about Lys-373 to about Ser-376; about Gln-384 to about Asp-387; and about Arg-422 to about Arg-426, all of SEQ ID NO:10.

pbpF

About Glu-7 to about Asp-11; about Ile-18 to about Lys-20; about Ile-55 to about Glu-59; about Ser-66 to about Gly-77; about Thr-92 to about Thr-97; about Arg-123 to about Asp-127; about Lys-154 to about Asp-159; about Ile-166 to about Gln-170; about Arg-230 to about Tyr-234; about Thr-247 to about Gly-251; about Lys-263 to about Ser-274; about Thr-294 to about Lys-300; about Gly-310 to about Leu-316; about Ser-341 to about Asp-346; about Ile-370 to about Asp-378; about Ser-393 to about Gly-396; about Leu-425 to about Lys-427; about Lys-433 to about Gly-435; about Pro-478 to about Gly-485; about Leu-499 to about Gly-505; about Thr-511 to about Pro-514; about Asp-543 to about Tyr 545; about Ser-558 to about Glu-563; about Asn-598 to about Gly-602; Lys-618 to about Thr-621; about Gly-628 to about Val-632; about Asp-643 to about Lys-646; about Asp-667 to about Arg-670; about Gly-681 to about Asp-684; and about Asn-686 to about Lys-689, all of SEQ ID NO:12.

pbpG

About Gln-4 to about His-8; about Lys-55 to about Ser-59; about Ile-72 to about Asp-75; about Lys-101 to about Ser-104; about Asp-142 to about Ser-145; about Asp-201 to about Gly-204; about Pro-221 to about Asp-224; about Pro-245 to about Asp-249; about Lys-253 to about Lys-256; and about Asn-297 to about Ter-302, all of SEQ ID NO:14.

cbrA

About Asn-23 to about Lys-35; about Ile-49 to about Lys-54; about Pro-85 to about Glu-88; about Asp-233 to about Lys-236; about Ser-243 to about Ile-247; about Ser-260 to about Ala-264; about Asp-296 to about Leu-298; and about Tyr-309 to about Ser-312, all of SEQ ID NO:16.

cbr B

About Asp-44 to about Asn-47; about Thr-219 to about Asp-222; and about Lys-325 to about Arg-328, all of SEQ ID NO:18.

cbrC

About Asn-48 to about Asp-52; and about Lys-141 to about Arg-145, all of SEQ ID NO:20.

enolase

About Leu 13 to about Pro 19; about Gly 63 to about Thr 65; about Thr 102 to about Lys 107; about Ser 156 to about Asp 159 about Arg 198 to about Leu 200; about Asp 206 to about Gly 209; about Lys 234 to about Glu 237; about Tyr 25 to about Asp 257; about Met 294 to about Gly 301; about Arg 308 to about Asp 311; about His 371 to about Glu 375; about Ser 397 to about Asp 402; about Lys 422 to about Gly 425, all of SEQ ID NO:22.

Antibodies

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991) J. Immunol. 147:60–69; U.S. Pat. Nos.

5,573,920, 4,474,893, 5,601,819, 4,714,681, 4,925,648; Kostelny, S. A. et al. (1992) J. Immunol. 148:1547–1553.

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}M$, $10^{-6}M$, $5\times10^{-7}M$, $10^{-7}M$, $5\times10^{-8}M$, $10^{-8}M$, $5\times10^{-9}M$, $10^{-9}M$, $5\times10^{-10}M$, $10^{-10}M$, $5\times10^{-11}M$, $10^{-11}M$, $5\times10^{-12}M$, $10^{-12}M$, $5\times10^{-13}M$, $10^{-13}M$, $5\times10^{-14}M$, $10^{-14}M$, $5\times10^{-15}M$, and $10^{-15}M$.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *ANTIBODIES: A LABORATORY MANUAL*, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. Monoclonal antibodies can be prepared using a wide variety of techniques known in the art including the use of hybridoma and recombinant technology. See, e.g., Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties).

Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) J. Immunol. Methods 182:41–50; Ames, R. S. et al. (1995) J. Immunol. Methods 184:177–186; Kettleborough, C. A. et al. (1994) Eur. J. Immunol. 24:952–958; Persic, L. et al. (1997) Gene 187 9–18; Burton, D. R. et al. (1994) Advances in Immunology 57:191–280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al. (1992) BioTechniques 12(6):864–869; and Sawai, H. et al. (1995) AJRI 34:26–34; and Better, M. et al. (1988) Science 240:1041–1043 (said references incorporated by reference in their entireties).

Examples of techniques which can be used to produce single-chain Fvs and antibodies include those described in U.S. Pat. Nos. 4,946,778 and 5,258,498; Huston et al. (1991) Methods in Enzymology 203:46–88; Shu, L. et al. (1993) PNAS 90:7995–7999; and Skerra, A. et al. (1988) Science 240:1038–1040. For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies, S. D. et al. (1989) J. Immunol. Methods 125:191–202; and U.S. Pat. No. 5,807, 715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E.

A., (1991) Molecular Immunology 28(4/5):489–498; Studnicka G. M. et al. (1994) Protein Engineering 7(6):805–814; Roguska M. A. et al. (1994) PNAS 91:969–973), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994) Immunol. Lett. 39:91–99; U.S. Pat. No. 5,474,981; Gillies, S. O. et al. (1992) PNAS 89:1428–1432; Fell, H. P. et al. (1991) J. Immunol. 146:2446–2452 (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fe region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fe portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) PNAS 88:10535–10539; Zheng, X. X. et al. (1995) J. Immunol. 154:5590–5600; and Vil, H. et al. (1992) PNAS 89:11337–11341 (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998) Blood 92(6):1981–1988; Chen, Z. et al. (1998) Cancer Res. 58(16): 3668–3678; Harrop, J. A. et al. (1998) J. Immunol. 161(4): 1786–1794; Zhu, Z. et al. (1998) Cancer Res. 58(15): 3209–3214; Yoon, D. Y. et al. (1998) J. Immunol. 160(7): 3170–3179; Prat, M. et al. (1998) J. Cell. Sci. 111(Pt2): 237–247; Pitard, V. et al (1997) J. Immunol. Methods 205(2):177–190; Liautard, J. et al. (1997) Cytokinde 9(4): 233–241; Carlson, N. G. et al. (1997) J. Biol. Chem. 272(17):11295–11301; Taryman, R. E. et al. (1995) Neuron 14(4):755–762; Muller, Y. A. et al. (1998) Structure 6(9): 1153–1167; Bartunek, P. et al. (1996) Cytokine 8(1):14–20 (said references incorporated by reference in their entireties).

Diagnostic Assays

The present invention further relates to methods for assaying staphylococcal infection in an animal by detecting the expression of genes encoding staphylococcal polypeptides of the present invention. The methods comprise analyzing tissue or body fluid from the animal for *Staphylococcus*-specific antibodies, nucleic acids, or proteins. Analysis of nucleic acid specific to *Staphylococcus* is assayed by PCR or hybridization techniques using nucleic acid sequences of the present invention as either hybridization probes or primers. See, e.g., Sambrook et al. Molecular cloning: A Laboratory Manual (Cold Spring Harbor Laboratory Press, 2nd ed., 1989, page 54 reference); Eremeeva et al. (1994) J. Clin. Microbiol. 32:803–810 (describing differentiation among spotted fever group *Rickettsiae* species by analysis of restriction fragment length polymorphism of PCR-amplified DNA) and Chen et al. 1994 J. Clin. Microbiol. 32:589–595 (detecting *B. burgdorferi* nucleic acids via PCR).

Where diagnosis of a disease state related to infection with *Staphylococcus* has already been made, the present invention is useful for monitoring progression or regression of the disease state whereby patients exhibiting enhanced *Staphylococcus* gene expression will experience a worse clinical outcome relative to patients expressing these gene(s) at a lower level.

By "biological sample" is intended any biological sample obtained from an animal, cell line, tissue culture, or other source which contains *Staphylococcus* polypeptide, mRNA, or DNA. Biological samples include body fluids (such as saliva, blood, plasma, urine, mucus, synovial fluid, etc.) tissues (such as muscle, skin, and cartilage) and any other biological source suspected of containing *Staphylococcus* polypeptides or nucleic acids. Methods for obtaining biological samples such as tissue are well known in the art.

The present invention is useful for detecting diseases related to *Staphylococcus* infections in animals. Preferred animals include monkeys, apes, cats, dogs, birds, cows, pigs, mice, horses, rabbits and humans. Particularly preferred are humans.

Total RNA can be isolated from a biological sample using any suitable technique such as the single-step guanidiniumthiocyanate-phenol-chloroform method described in Chomczynski et al. (1987) Anal. Biochem. 162:156–159. mRNA encoding *Staphylococcus* polypeptides having sufficient homology to the nucleic acid sequences identified in Table 1 to allow for hybridization between complementary sequences are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al. (1990) Cell 63:303–312. Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. A *S. aureus* polypeptide DNA sequence shown in Table 1 labeled according to any appropriate method (such as the $^{32}$P-multiprimed DNA labeling system (Amersham)) is used as probe. After hybridization overnight, the filter is washed and exposed to x-ray film. DNA for use as probe according to the present invention is described in the sections above and will preferably at least 15 nucleotides in length.

S1 mapping can be performed as described in Fujita et al. (1987) Cell 49:357–367. To prepare probe DNA for use in S1 mapping, the sense strand of an above-described *S. aureus* DNA sequence of the present invention is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding *Staphylococcus* polypeptides).

Levels of mRNA encoding *Staphylococcus* polypeptides are assayed, for e.g., using the RT-PCR method described in Makino et al. (1990) Technique 2:295–301. By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the *Staphylococcus* polypeptides of the present invention) are quantified using an imaging analyzer. RT and PCR reaction ingredients and conditions, reagent and gel concentrations, and labeling methods are well known in the art. Variations on the RT-PCR method will be apparent to the skilled artisan. Other PCR methods that can detect the nucleic acid of the present invention can be found in PCR PRIMER: A LABORATORY MANUAL (C. W. Dieffenbach et al. eds., Cold Spring Harbor Lab Press, 1995).

The polynucleotides of the present invention, including both DNA and RNA, may be used to detect polynucleotides of the present invention or *Staphylococcal* species including *S. aureus* using bio-chip technology. The present invention includes both high density chip arrays (>1000 oligonucleotides per $cm^2$) and low density chip arrays (<1000 oligonucleotides per $cm^2$). Bio-chips comprising arrays of polynucleotides of the present invention may be used to detect *Staphylococcal* species, including *S. aureus*, in biological and environmental samples and to diagnose an animal, including humans, with an *S. aureus* or other *Staphylococcal* infection. The bio-chips of the present invention may comprise polynucleotide sequences of other pathogens including bacteria, viral, parasitic, and fungal polynucleotide sequences, in addition to the polynucleotide sequences of the present invention, for use in rapid differential pathogenic detection and diagnosis. The bio-chips can also be used to monitor an *S. aureus* or other *Staphylococcal* infections and to monitor the genetic changes (deletions, insertions, mismatches, etc.) in response to drug therapy in the clinic and drug development in the laboratory. The bio-chip technology comprising arrays of polynucleotides of the present invention may also be used to simultaneously monitor the expression of a multiplicity of genes, including those of the present invention. In addition, the bio-chips of the present invention may be used to screen large numbers of peptides, polypeptides, antibodies, small molecules and other drug compounds which bind to the polynucleotides of the present invention. The bio-chips may also be used to measure relative binding or binding affinities (in on-rates or off-rates) of peptides, polypeptides, antibodies, small molecules and other drug compounds to the polynucleotides of the present invention. The polynucleotides used to comprise a selected array may be specified in the same manner as for the fragments, i.e., by their 5' and 3' positions or length in contiguous base pairs and include from. Methods and particular uses of the polynucleotides of the present invention to detect *Staphylococcal* species, including *S. aureus*, using bio-chip technology include those known in the art and those of: U.S. Pat. Nos. 5,324,633, 5,510,270, 5,545,531, 5,445, 934, 5,677,195, 5,532,128, 5,556,752, 5,527,681, 5,451,683, 5,424,186, 5,607,646, 5,658,732 and World Patent Nos. WO/9710365, WO/9511995, WO/9743447, WO/9535505, each incorporated herein in their entireties.

Biosensors using the polynucleotides of the present invention may also be used to detect, diagnose, and monitor *S. aureus* or other *Staphylococcal* species and infections thereof. Biosensors using the polynucleotides of the present invention may also be used to detect particular polynucleotides of the present invention. Biosensors using the polynucleotides of the present invention may also be used to monitor the genetic changes (deletions, insertions, mismatches, etc.) in response to drug therapy in the clinic and drug development in the laboratory. In addition, the biosensors of the present invention may be used to screen large numbers of polynucleotides, peptides, polypeptides, antibodies, small molecules and other drug compounds which bind to the polynucleotides of the present invention. The biosensors may also be used to measure relative binding or binding affinities (in on-rates or off-rates) of polynucleotides, peptides, polypeptides, antibodies, small molecules, and other drug compounds to the polynucleotides of the present invention. Methods and particular uses of the polynucleotides of the present invention to detect *Staphylococcal* species, including *S. aureus*, using biosensors include those known in the art and those of: U.S. Pat. Nos. 5,721,102, 5,658,732, 5,631,170, and World Patent Nos.

WO/9735011, WO/9720203, each incorporated herein in their entireties.

Thus, the present invention includes both bio-chips and biosensors comprising polynucleotides of the present invention and methods of their use.

Assaying *Staphylococcus* polypeptide levels in a biological sample can occur using any art-known method, such as antibody-based techniques. For example, *Staphylococcus* polypeptide expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of *Staphylococcus* polypeptides for Western-blot or dot/slot assay. See, e.g., Jalkanen, M. et al. (1985) J. Cell. Biol. 101:976–985; Jalkanen, M. et al. (1987) J. Cell . Biol. 105:3087–3096. In this technique, which is based on the use of cationic solid phases, quantitation of a *Staphylococcus* polypeptide can be accomplished using an isolated *Staphylococcus* polypeptide as a standard. This technique can also be applied to body fluids.

Other antibody-based methods useful for detecting *Staphylococcus* polypeptide gene expression include immunoassays, such as the ELISA and the radioimmunoassay (RIA). For example, a *Staphylococcus* polypeptide-specific monoclonal antibodies can be used both as an immunoabsorbent and as an enzyme-labeled probe to detect and quantify a *Staphylococcus* polypeptide. The amount of a *Staphylococcus* polypeptide present in the sample can be calculated by reference to the amount present in a standard preparation using a linear regression computer algorithm. Such an ELISA is described in Iacobelli et al. (1988) Breast Cancer Research and Treatment 11:19–30. In another ELISA assay, two distinct specific monoclonal antibodies can be used to detect *Staphylococcus* polypeptides in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting the *Staphylococcus* polypeptide with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample. Variations of the above and other immunological methods included in the present invention can also be found in Harlow et al., ANTIBODIES: A LABORATORY MANUAL, (Cold Spring Harbor Laboratory Press, 2nd ed. 1988).

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Further suitable labels for the *Staphylococcus* polypeptide-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging. See, e.g., Perkins et al. (1985) Eur. J. Nucl. Med. 10:296–301; Carasquillo et al. (1987) J. Nucl. Med. 28:281–287. For example, $^{111}$In coupled to monoclonal antibodies with 1-(P-isothiocyanatobenzyl)-DPTA has shown little uptake in non-tumors tissues, particularly the liver, and therefore enhances specificity of tumor localization. See, Esteban et al. (1987) J. Nucl. Med. 28:861–870.

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, *Pseudomonas* toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al. (1976) Clin. Chim. Acta 70:1–31, and Schurs et al. (1977) Clin. Chim. Acta 81:1–40. Coupling techniques mentioned in the latter are the glutaraldehyde method, the periodate method, the dimaleimide method, the m-maleimidobenzyl-N-hydroxy-succinimide ester method, all of which methods are incorporated by reference herein.

In a related aspect, the invention includes a diagnostic kit for use in screening serum containing antibodies specific against *S. aureus* infection. Such a kit may include an isolated *S. aureus* antigen comprising an epitope which is specifically immunoreactive with at least one anti-*S. aureus* antibody. Such a kit also includes means for detecting the binding of said antibody to the antigen. In specific embodiments, the kit may include a recombinantly produced or chemically synthesized peptide or polypeptide antigen. The peptide or polypeptide antigen may be attached to a solid support.

In a more specific embodiment, the detecting means of the above-described kit includes a solid support to which said peptide or polypeptide antigen is attached. Such a kit may also include a non-attached reporter-labeled anti-human antibody. In this embodiment, binding of the antibody to the *S. aureus* antigen can be detected by binding of the reporter labeled antibody to the anti-*S. aureus* polypeptide antibody.

In a related aspect, the invention includes a method of detecting *S. aureus* infection in a subject. This detection method includes reacting a body fluid, preferably serum, from the subject with an isolated *S. aureus* antigen, and examining the antigen for the presence of bound antibody. In a specific embodiment, the method includes a polypeptide antigen attached to a solid support, and serum is reacted with the support. Subsequently, the support is reacted with a reporter-labeled anti-human antibody. The support is then examined for the presence of reporter-labeled antibody.

The solid surface reagent employed in the above assays and kits is prepared by known techniques for attaching protein material to solid support material, such as polymeric beads, dip sticks, 96-well plates or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

The polypeptides and antibodies of the present invention, including fragments thereof, may be used to detect *Staphylococcal* species including *S. aureus* using bio-chip and biosensor technology. Bio-chip and biosensors of the present invention may comprise the polypeptides of the present invention to detect antibodies, which specifically recognize *Staphylococcal* species, including *S. aureus*. Bio-chip and biosensors of the present invention may also comprise antibodies which specifically recognize the polypeptides of the present invention to detect *Staphylococcal* species, including *S. aureus* or specific polypeptides of the present invention. Bio-chips or biosensors comprising polypeptides or antibodies of the present invention may be used to detect *Staphylococcal* species, including *S. aureus*, in biological and environmental samples and to diagnose an animal, including humans, with an *S. aureus* or other *Staphylococcal* infection. Thus, the present invention includes both bio-chips and biosensors comprising polypeptides or antibodies of the present invention and methods of their use.

The bio-chips of the present invention, discussed above, may further comprise polypeptide sequences of other pathogens including bacteria, viral, parasitic, and fungal polypeptide sequences, in addition to the polypeptide sequences of the present invention, for use in rapid differential pathogenic detection and diagnosis. The bio-chips of the present invention may further comprise antibodies or fragments thereof specific for other pathogens including bacteria, viral, parasitic, and fungal polypeptide sequences, in addition to the antibodies or fragments thereof of the present invention, for use in rapid differential pathogenic detection and diagnosis. The bio-chips and biosensors of the present invention may also be used to monitor an *S. aureus* or other *Staphylococcal* infection and to monitor the genetic changes (amino acid deletions, insertions, substitutions, etc.) in response to drug therapy in the clinic and drug development in the laboratory. The bio-chip and biosensors comprising polypeptides or antibodies of the present invention may also be used to simultaneously monitor the expression of a multiplicity of polypeptides, including those of the present invention. In addition, the bio-chips and biosensors of the present invention may be used to screen large numbers of polynucleotides, peptides, polypeptides, antibodies, small molecules, and other drug compounds which bind to the polypeptides of the present invention. The bio-chips may also be used to measure relative binding or binding affinities (in on-rates or off-rates) of polynucleotides, peptides, polypeptides, antibodies, small molecules and other drug compounds to the polypeptides of the present invention. The polypeptides used to comprise a bio-chip or biosensor of the present invention may be specified in the same manner as for the fragments, i.e., by their N-terminal and C-terminal positions or length in contiguous amino acid residue. Methods and particular uses of the polypeptides and antibodies of the present invention to detect *Staphylococcal* species, including *S. aureus*, or specific polypeptides using bio-chip and biosensor technology include those known in the art, those of the U.S. Pat. Nos. and World Patent Nos. listed above for bio-chips and biosensors using polynucleotides of the present invention, and those of: U.S. Pat. Nos. 5,324,633, 5,658,732, 5,135,852, 5,567,301, 5,677,196, 5,690,894, 5,527,681, 5,510,270, 5,545,531, 5,445,934, 5,677,195, 5,532,128, 5,556,752, 5,451,683, 5,424,186, 5,607,646, and World Patent Nos. WO/9729366, WO/9612957, WO/9710365, WO/9511995, WO/9743447, WO/9535505, each incorporated herein in their entireties.

Treatment

Agonists and Antagonists—Assays and Molecules

The invention also provides a method of screening compounds to identify those which enhance or block the biological activity of the *S. aureus* polypeptides of the present invention. The present invention further provides where the compounds kill or slow the growth of *S. aureus*. The ability of *S. aureus* antagonists, including *S. aureus* ligands, to prophylactically or therapeutically block antibiotic resistance may be easily tested by the skilled artisan. See, e.g., Straden et al. (1997) J Bacteriol. 179(1):9–16.

An agonist is a compound which increases the natural biological function or which functions in a manner similar to the polypeptides of the present invention, while antagonists decrease or eliminate such functions. Potential antagonists include small organic molecules, peptides, polypeptides, and antibodies that bind to a polypeptide of the invention and thereby inhibit or extinguish its activity.

The antagonists may be employed for instance to inhibit peptidoglycan cross bridge formation. Antibodies against *S. aureus* may be employed to bind to and inhibit *S. aureus* activity to treat antibiotic resistance. Any of the above antagonists may be employed in a composition with a pharmaceutically acceptable carrier.

Vaccines

The present invention also provides vaccines comprising one or more polypeptides of the present invention. Heterogeneity in the composition of a vaccine may be provided by combining *S. aureus* polypeptides of the present invention. Multi-component vaccines of this type are desirable because they are likely to be more effective in eliciting protective immune responses against multiple species and strains of the *Staphylococcus* genus than single polypeptide vaccines.

Multi-component vaccines are known in the art to elicit antibody production to numerous immunogenic components. See, e.g., Decker et al. (1996) J. Infect. Dis. 174:S270–275. In addition, a hepatitis B, diphtheria, tetanus, pertussis tetravalent vaccine has recently been demonstrated to elicit protective levels of antibodies in human infants against all four pathogenic agents. See, e.g., Aristegui, J. et al. (1997) Vaccine 15:7–9.

The present invention in addition to single-component vaccines includes multi-component vaccines. These vaccines comprise more than one polypeptide, immunogen or antigen. Thus, a multi-component vaccine would be a vaccine comprising more than one of the *S. aureus* polypeptides of the present invention.

Further within the scope of the invention are whole cell and whole viral vaccines. Such vaccines may be produced recombinantly and involve the expression of one or more of the *S. aureus* polypeptides described in Table 1. For example, the *S. aureus* polypeptides of the present invention may be either secreted or localized intracellular, on the cell surface, or in the periplasmic space. Further, when a recombinant virus is used, the *S. aureus* polypeptides of the present invention may, for example, be localized in the viral envelope, on the surface of the capsid, or internally within the capsid. Whole cells vaccines which employ cells expressing heterologous proteins are known in the art. See, e.g., Robinson, K. et al. (1997) Nature Biotech. 15:653–657; Sirard, J. et al. (1997) Infect. Immun. 65:2029–2033; Chabalgoity, J. et al. (1997) Infect. Immun. 65:2402–2412. These cells may be administered live or may be killed prior to administration. Chabalgoity, J. et al., supra, for example, report the successful use in mice of a live attenuated *Salmonella* vaccine strain which expresses a portion of a platyhelminth fatty acid-binding protein as a fusion protein on its cells surface.

A multi-component vaccine can also be prepared using techniques known in the art by combining one or more *S. aureus* polypeptides of the present invention, or fragments thereof, with additional non-staphylococcal components (e.g., diphtheria toxin or tetanus toxin, and/or other compounds known to elicit an immune response). Such vaccines are useful for eliciting protective immune responses to both members of the *Staphylococcus* genus and non-staphylococcal pathogenic agents.

The vaccines of the present invention also include DNA vaccines. DNA vaccines are currently being developed for a number of infectious diseases. See, et al., Boyer, et al. (1997) Nat. Med. 3:526–532; reviewed in Spier, R. (1996) Vaccine 14:1285–1288. Such DNA vaccines contain a nucleotide sequence encoding one or more *S. aureus* polypeptides of the present invention oriented in a manner that allows for expression of the subject polypeptide. For example, the direct administration of plasmid DNA encoding *B. burgdorgeri* OspA has been shown to elicit protective immunity in mice against borrelial challenge. See, Luke et al. (1997) J. Infect. Dis. 175:91–97.

The present invention also relates to the administration of a vaccine which is co-administered with a molecule capable of modulating immune responses. Kim et al. (1997) Nature Biotech. 15:641–646, for example, report the enhancement of immune responses produced by DNA immunizations when DNA sequences encoding molecules which stimulate the immune response are co-administered. In a similar fashion, the vaccines of the present invention may be co-administered with either nucleic acids encoding immune modulators or the immune modulators themselves. These immune modulators include granulocyte macrophage colony stimulating factor (GM-CSF) and CD86.

The vaccines of the present invention may be used to confer resistance to staphylococcal infection by either passive or active immunization. When the vaccines of the present invention are used to confer resistance to staphylococcal infection through active immunization, a vaccine of the present invention is administered to an animal to elicit a protective immune response which either prevents or attenuates a staphylococcal infection. When the vaccines of the present invention are used to confer resistance to staphylococcal infection through passive immunization, the vaccine is provided to a host animal (e.g., human, dog, or mouse), and the antisera elicited by this antisera is recovered and directly provided to a recipient suspected of having an infection caused by a member of the *Staphylococcus* genus.

The ability to label antibodies, or fragments of antibodies, with toxin molecules provides an additional method for treating staphylococcal infections when passive immunization is conducted. In this embodiment, antibodies, or fragments of antibodies, capable of recognizing the *S. aureus* polypeptides disclosed herein, or fragments thereof, as well as other *Staphylococcus* proteins, are labeled with toxin molecules prior to their administration to the patient. When such toxin derivatized antibodies bind to *Staphylococcus* cells, toxin moieties will be localized to these cells and will cause their death.

The present invention thus concerns and provides a means for preventing or attenuating a staphylococcal infection resulting from organisms which have antigens that are recognized and bound by antisera produced in response to the polypeptides of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the compound(s) are provided in advance of any symptoms of staphylococcal infection. The prophylactic administration of the compound (s) serves to prevent or attenuate any subsequent infection. When provided therapeutically, the compound(s) is provided upon or after the detection of symptoms which indicate that an animal may be infected with a member of the *Staphylococcus* genus. The therapeutic administration of the compound(s) serves to attenuate any actual infection. Thus, the *S. aureus* polypeptides, and fragments thereof, of the present invention may be provided either prior to the onset of infection (so as to prevent or attenuate an anticipated infection) or after the initiation of an actual infection.

The polypeptides of the invention, whether encoding a portion of a native protein or a functional derivative thereof, may be administered in pure form or may be coupled to a macromolecular carrier. Example of such carriers are proteins and carbohydrates. Suitable proteins which may act as macromolecular carrier for enhancing the immunogenicity of the polypeptides of the present invention include keyhole limpet hemacyanin (KLH) tetanus toxoid, pertussis toxin, bovine serum albumin, and ovalbumin. Methods for coupling the polypeptides of the present invention to such macromolecular carriers are disclosed in Harlow et al., ANTIBODIES: A LABORATORY MANUAL, (Cold Spring Harbor Laboratory Press, 2nd ed. 1988).

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

While in all instances the vaccine of the present invention is administered as a pharmacologically acceptable compound, one skilled in the art would recognize that the composition of a pharmacologically acceptable compound varies with the animal to which it is administered. For example, a vaccine intended for human use will generally not be co-administered with Freund's adjuvant. Further, the level of purity of the *S. aureus* polypeptides of the present invention will normally be higher when administered to a human than when administered to a non-human animal.

As would be understood by one of ordinary skill in the art, when the vaccine of the present invention is provided to an animal, it may be in a composition which may contain salts, buffers, adjuvants, or other substances which are desirable for improving the efficacy of the composition. Adjuvants are substances that can be used to specifically augment a specific immune response. These substances generally perform two functions: (1) they protect the antigen(s) from being rapidly catabolized after administration and (2) they nonspecifically stimulate immune responses.

Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Other substances useful as adjuvants are the saponins such as, for example, Quil A. (Superfos A/S, Denmark). Preferred adjuvants for use in the present invention include aluminum salts, such as $AlK(SO_4)_2$, $AlNa(SO_4)_2$, and $AlNH_4(SO_4)$. Examples of materials suitable for use in vaccine compositions are provided in REMINGTON'S PHARMACEUTICAL SCIENCES 1324–1341 (A. Osol, ed, Mack Publishing Co, Easton, Pa., (1980) (incorporated herein by reference).

The therapeutic compositions of the present invention can be administered parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Therapeutic compositions of the present invention can also be administered in encapsulated form. For example, intranasal immunization using vaccines encapsulated in biodegradable microsphere composed of poly(DL-lactide-co-glycolide). See, Shahin, R. et al. (1995) Infect. Immun. 63:1195–1200. Similarly, orally administered encapsulated *Salmonella typhimurium* antigens can also be used. Allaoui-Attarki, K. et al. (1997) Infect. Immun. 65:853–857. Encapsulated vaccines of the present invention can be administered by a variety of routes including those involving contacting the vaccine with mucous membranes (e.g., intranasally, intracolonicly, intraduodenally).

Many different techniques exist for the timing of the immunizations when a multiple administration regimen is utilized. It is possible to use the compositions of the invention more than once to increase the levels and diversities of expression of the immunoglobulin repertoire expressed by the immunized animal. Typically, if multiple immunizations are given, they will be given one to two months apart.

According to the present invention, an "effective amount" of a therapeutic composition is one which is sufficient to achieve a desired biological effect. Generally, the dosage needed to provide an effective amount of the composition will vary depending upon such factors as the animal's or human's age, condition, sex, and extent of disease, if any, and other variables which can be adjusted by one of ordinary skill in the art.

The antigenic preparations of the invention can be administered by either single or multiple dosages of an effective amount. Effective amounts of the compositions of the invention can vary from 0.01–1,000 μg/ml per dose, more preferably 0.1–500 μg/ml per dose, and most preferably 10–300 μg/ml per dose.

EXAMPLES

Example 1

Isolation of a Selected DNA Clone from the Deposited Sample

Three approaches can be used to isolate a *S. aureus* clone comprising a polynucleotide of the present invention from any *S. aureus* genomic DNA library. The *S. aureus* strain ISP3 has been deposited as a convienent source for obtaining a *S. aureus* strain although a wide variety of strains *S. aureus* strains can be used which are known in the art.

*S. aureus* genomic DNA is prepared using the following method. A 20 ml overnight bacterial culture grown in a rich medium (e.g., Trypticase Soy Broth, Brain Heart Infusion broth or Super broth), pelleted, washed two times with TES (30 mM Tris-pH 8.0, 25 mM EDTA, 50 mM NaCl), and resuspended in 5 ml high salt TES (2.5M NaCl). Lysostaphin is added to final concentration of approx 50 ug/ml and the mixture is rotated slowly 1 hour at 37 C to make protoplast cells. The solution is then placed in incubator (or place in a shaking water bath) and warmed to 55 C. Five hundred micro liter of 20% sarcosyl in TES (final concentration 2%) is then added to lyse the cells. Next, guanidine HCl is added to a final concentration of 7M (3.69 g in 5.5 ml). The mixture is swirled slowly at 55 C for 60–90 min (solution should clear). A CsCl gradient is then set up in SW41 ultra clear tubes using 2.0 ml 5.7M CsCl and overlaying with 2.85M CsCl. The gradient is carefully overlayed with the DNA-containing GuHCl solution. The gradient is spun at 30,000 rpm, 20 C for 24 hr and the lower DNA band is collected. The volume is increased to 5 ml with TE buffer. The DNA is then treated with protease K (10 ug/ml) overnight at 37 C, and precipitated with ethanol. The precipitated DNA is resuspended in a desired buffer.

In the first method, a plasmid is directly isolated by screening a plasmid *S. aureus* genomic DNA library using a polynucleotide probe corresponding to a polynucleotide of the present invention. Particularly, a specific polynucleotide with 30–40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (See, e.g., Maniatis et al., Molecular Cloning: A Laboratory Manual, Cold Spring Harbor Press, Cold Spring, N.Y. (1982).) The library is transformed into a suitable host, as indicated above (such as XL-1 Blue (Stratagene)) using techniques known to those of skill in the art. See, e.g., Sambrook et al. MOLECULAR CLONING: A LABORATORY MANUAL (Cold Spring Harbor, N.Y. 2nd ed. 1989); Ausubel et al., CURRENT PROTOCOLS IN MOLECULAR BIOLOGY (John Wiley and Sons, N.Y. 1989). The transformants are plated on 1.5% agar plates (containing the appropriate selection agent, e.g., ampicillin) to a density of about 150 transformants (colonies) per plate. These plates are screened using Nylon membranes according to routine methods for bacterial colony screening. See, e.g., Sambrook et al. MOLECULAR CLONING: A LABORATORY MANUAL (Cold Spring Harbor, N.Y. 2nd ed. 1989); Ausubel et al., CURRENT PROTOCOLS IN MOLECULAR BIOLOGY (John Wiley and Sons, N.Y. 1989) or other techniques known to those of skill in the art.

Alternatively, two primers of 15–25 nucleotides derived from the 5' and 3' ends of a polynucleotide of Table 1 are synthesized and used to amplify the desired DNA by PCR using a *S. aureus* genomic DNA prep (e.g., the deposited *S. aureus* ISP3) as a template. PCR is carried out under routine conditions, for instance, in 25 μl of reaction mixture with 0.5 ug of the above DNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Finally, overlapping oligos of the DNA sequences of Table 1 can be synthesized and used to generate a nucleotide sequence of desired length using PCR methods known in the art.

Example 2(a)

Expression and Purification *Staphylococcal* Polypeptides in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Ampr'") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin (QIAGEN, Inc., supra) and suitable single restriction enzyme cleavage sites. These elements are arranged such that an inserted DNA fragment encoding a polypeptide expresses that polypeptide with the six His residues (i.e., a "6xHis tag") covalently linked to the carboxyl terminus of that polypeptide.

The DNA sequence encoding the desired portion of a *S. aureus* protein of the present invention is amplified from *S. aureus* genomic DNA or from the deposited DNA clone using PCR oligonucleotide primers which anneal to the 5' and 3' sequences coding for the portion of the *S. aureus* polynucleotide. Additional nucleotides containing restriction sites to facilitate cloning in the pQE60 vector are added to the 5' and 3' sequences, respectively.

For cloning the mature protein, the 5' primer has a sequence containing an appropriate restriction site followed by nucleotides of the amino terminal coding sequence of the desired *S. aureus* polynucleotide sequence in Table 1. One of ordinary skill in the art would appreciate that the point in the protein coding sequence where the 5' and 3' primers begin may be varied to amplify a DNA segment encoding any desired portion of the complete protein shorter or longer than the mature form. The 3' primer has a sequence containing an appropriate restriction site followed by nucleotides complementary to the 3' end of the desired coding sequence of Table 1, excluding a stop codon, with the coding sequence aligned with the restriction site so as to maintain its reading frame with that of the six His codons in the pQE60 vector.

The amplified *S. aureus* DNA fragment and the vector pQE60 are digested with restriction enzymes which recognize the sites in the primers and the digested DNAs are then ligated together. The *S. aureus* DNA is inserted into the restricted pQE60 vector in a manner which places the *S. aureus* protein coding region downstream from the IPTG-inducible promoter and in-frame with an initiating AUG and the six histidine codons.

The ligation mixture is transformed into competent *E. coli* cells using standard procedures such as those described by Sambrook et al., supra. *E. coli* strain M15/rep4, containing multiple copies of the plasmid pREP4, which expresses the lac repressor and confers kanamycin resistance ("Kan'"), is used in carrying out the illustrative example described herein. This strain, which is only one of many that are suitable for expressing a *S. aureus* polypeptide, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("$OD^{600}$") of between 0.4 and 0.6. Isopropyl-β-D-thiogalactopyranoside .("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the *S. aureus* polypeptide is loaded onto a nickel-nitrilo-tri-acetic acid ("Ni-NTA") affinity resin column (QIAGEN, Inc., supra). Proteins with a 6xHis tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the *S. aureus* polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM imidazole. Imidazole is removed by a final dialyzing step against PBS or 50 mM sodium acetate pH 6 buffer plus 200 mM NaCl. The purified protein is stored at 4° C. or frozen at −80° C.

Alternatively, the polypeptides of the present invention can be produced by a non-denaturing method. In this method, after the cells are harvested by centrifugation, the cell pellet from each liter of culture is resuspended in 25 ml of Lysis Buffer A at 4° C. (Lysis Buffer A=50 mM Na-phosphate, 300 mM NaCl, 10 mM 2-mercaptoethanol, 10% Glycerol, pH 7.5 with 1 tablet of Complete EDTA-free protease inhibitor cocktail (Boehringer Mannheim #1873580) per 50 ml of buffer). Absorbance at 550 nm is approximately 10–20 O.D./ml. The suspension is then put through three freeze/thaw cycles from −70° C. (using a ethanol-dry ice bath) up to room temperature. The cells are lysed via sonication in short 10 sec bursts over 3 minutes at approximately 80W while kept on ice. The sonicated sample is then centrifuged at 15,000 RPM for 30 minutes at 4° C. The supernatant is passed through a column containing 1.0 ml of CL-4B resin to pre-clear the sample of any proteins that may bind to agarose non-specifically, and the flow-through fraction is collected.

The pre-cleared flow-through is applied to a nickel-nitrilo-tri-acetic acid ("Ni-NTA") affinity resin column (Qiagen, Inc., supra). Proteins with a 6xHis tag bind to the Ni-NTA resin with high affinity and can be purified in a simple one-step procedure. Briefly, the supernatant is loaded onto the column in Lysis Buffer A at 4° C., the column is first washed with 10 volumes of Lysis Buffer A until the A280 of the eluate returns to the baseline. Then, the column is washed with 5 volumes of 40 mM Imidazole (92% Lysis Buffer A/8% Buffer B) (Buffer B=50 mM Na-Phosphate, 300 mM NaCl, 10% Glycerol, 10 mM 2-mercaptoethanol, 500 mM Imidazole, pH of the final buffer should be 7.5). The protein is eluted off of the column with a series of increasing Imidazole solutions made by adjusting the ratios of Lysis Buffer A to Buffer B. Three different concentrations are used: 3 volumes of 75 mM Imidazole, 3 volumes of 150 mM Imidazole, 5 volumes of 500 mM Imidazole. The fractions containing the purified protein are analyzed using 8%, 10% or 14% SDS-PAGE depending on the protein size. The purified protein is then dialyzed 2× against phosphate-buffered saline (PBS) in order to place it into an easily workable buffer. The purified protein is stored at 4° C. or frozen at −80°

The following is another alternative method may be used to purify S. aureus expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the S. aureus polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded S. aureus polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the S. aureus polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the S. aureus polypeptide (determined, for instance, by 16% SDS-PAGE) are then pooled.

The resultant S. aureus polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2(b)

Expression and Purification *Staphylococcal* Polypeptides in *E. coli*

Alternatively, the vector pQE10 can be used to clone and express polypeptides of the present invention. The difference being such that an inserted DNA fragment encoding a polypeptide expresses that polypeptide with the six His residues (i.e., a "6xHis tag") covalently linked to the amino terminus of that polypeptide. The bacterial expression vector pQE10 (QIAGEN, Inc., 9259 Eton Avenue, Chatsworth, Calif., 91311) is used in this example. The components of the pQE10 plasmid are arranged such that the inserted DNA sequence encoding a polypeptide of the present invention expresses the polypeptide with the six His residues (i.e., a "6xHis tag")) covalently linked to the amino terminus.

The DNA sequences encoding the desired portions of a polypeptide of Table 1 or expressed by the plasmids listed in Table 1 are amplified using PCR oligonucleotide primers from either genomic S. aureus DNA or DNA from the plasmid clones listed in Table 1 clones of the present invention. The PCR primers anneal to the nucleotide sequences encoding the desired amino acid sequence of a polypeptide of the present invention. Additional nucleotides containing restriction sites to facilitate cloning in the pQE10 vector are added to the 5' and 3' primer sequences, respectively.

For cloning a polypeptide of the present invention, the 5' and 3' primers are selected to amplify their respective nucleotide coding sequences. One of ordinary skill in the art would appreciate that the point in the protein coding sequence where the 5' and 3' primers begins may be varied to amplify a DNA segment encoding any desired portion of a polypeptide of the present invention. The 5' primer is designed so the coding sequence of the 6×His tag is aligned with the restriction site so as to maintain its reading frame with that of S. aureus polypeptide. The 3' is designed to include an stop codon. The amplified DNA fragment is then cloned, and the protein expressed, as described above for the pQE60 plasmid.

The DNA sequences encoding the amino acid sequences of Table 1 may also be cloned and expressed as fusion proteins by a protocol similar to that described directly above, wherein the pET-32b(+) vector (Novagen, 601 Science Drive, Madison, Wis. 53711) is preferentially used in place of pQE10.

Example 2(c)

Expression and Purification of Stahphlococcusl Polypeptides in E. coli

The bacterial expression vector pQE60 is used for bacterial expression in this example (QIAGEN, Inc., 9259 Eton Avenue, Chatsworth, Calif., 91311). However, in this example, the polypeptide coding sequence is inserted such that translation of the six His codons is prevented and, therefore, the polypeptide is produced with no 6×His tag.

The DNA sequence encoding the desired portion of the S. aureus amino acid sequence is amplified from a S. aureus genomic DNA prep using PCR oligonucleotide primers which anneal to the 5' and 3' nucleotide sequences corresponding to the desired portion of the S. aureus polypeptides. Additional nucleotides containing restriction sites to facilitate cloning in the pQE60 vector are added to the 5' and 3' primer sequences.

For cloning a S. aureus polypeptides of the present invention, 5' and 3' primers are selected to amplify their respective nucleotide coding sequences. One of ordinary skill in the art would appreciate that the point in the protein coding sequence where the 5' and 3' primers begin may be varied to amplify a DNA segment encoding any desired portion of a polypeptide of the present invention. The 3' and 5' primers contain appropriate restriction sites followed by nucleotides complementary to the 5' and 3' ends of the coding sequence respectively. The 3' primer is additionally designed to include an in-frame stop codon.

The amplified S. aureus DNA fragments and the vector pQE60 are digested with restriction enzymes recognizing the sites in the primers and the digested DNAs are then ligated together. Insertion of the S. aureus DNA into the restricted pQE60 vector places the S. aureus protein coding region including its associated stop codon downstream from the IPTG-inducible promoter and in-frame with an initiating AUG. The associated stop codon prevents translation of the six histidine codons downstream of the insertion point.

The ligation mixture is transformed into competent E. coli cells using standard procedures such as those described by Sambrook et al. E. coli strain M15/rep4, containing multiple copies of the plasmid pREP4, which expresses the lac repressor and confers kanamycin resistance ("Kan$^r$"), is used in carrying out the illustrative example described herein. This strain, which is only one of many that are suitable for expressing S. aureus polypeptide, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 $\mu$g/ml) and kanamycin (25 $\mu$g/ml). The O/N culture is used to inoculate a large culture, at a dilution of approximately 1:25 to 1:250. The cells are grown to an optical density at 600 nm ("OD600") of between 0.4 and 0.6. isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

To purify the S. aureus polypeptide, the cells are then stirred for 3–4 hours at 4° C. in 6M guanidine-HCl, pH 8. The cell debris is removed by centrifugation, and the supernatant containing the S. aureus polypeptide is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure S. aureus polypeptide. The purified protein is stored at 4° C. or frozen at −80° C.

The following alternative method may be used to purify S. aureus polypeptides expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the S. aureus polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded S. aureus polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the S. aureus polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the S. aureus polypeptide (determined, for instance, by 16% SDS-PAGE) are then pooled.

The resultant S. aureus polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2(d)

Cloning and Expression of S. aureus in Other Bacteria

S. aureus polypeptides can also be produced in: S. aureus using the methods of S. Skinner et al., (1988) Mol. Microbiol. 2:289–297 or J. I. Moreno (1996) Protein Expr. Purif. 8(3):332–340; Lactobacillus using the methods of C. Rush et al., 1997 Appl. Microbiol. Biotechnol. 47(5):537–542; or in Bacillus subtilis using the methods Chang et al., U.S. Pat. No. 4,952,508.

Example 3

Cloning and Expression in COS Cells

A S. aureus expression plasmid is made by cloning a portion of the DNA encoding a S. aureus polypeptide into the expression vector pDNAI/Amp or pDNAIII (which can be obtained from Invitrogen, Inc.). The expression vector pDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a DNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al. 1984 Cell 37:767. The fusion of the HA tag to the target protein allows easy detection and recovery of the recombinant protein with an antibody that recognizes the HA epitope. pDNAIII contains, in addition, the selectable neomycin marker.

A DNA fragment encoding a S. aureus polypeptide is cloned into the polylinker region of the vector so that recombinant protein expression is directed by the CMV promoter. The plasmid construction strategy is as follows. The DNA from a S. aureus genomic DNA prep is amplified using primers that contain convenient restriction sites, much as described above for construction of vectors for expression of S. aureus in E. coli. The 5' primer contains a Kozak sequence, an AUG start codon, and nucleotides of the 5' coding region of the S. aureus polypeptide. The 3' primer, contains nucleotides complementary to the 3' coding sequence of the S. aureus DNA, a stop codon, and a convenient restriction site.

The PCR amplified DNA fragment and the vector, pDNAI/Amp, are digested with appropriate restriction enzymes and then ligated. The ligation mixture is transformed into an appropriate E. coli strain such as SURE™ (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the S. aureus polypeptide For expression of a recombinant S. aureus polypeptide, COS cells are transfected with an expression vector, as described above, using DEAE-dextran, as described, for instance, by Sambrook et al. (supra). Cells are incubated under conditions for expression of S. aureus by the vector.

Expression of the S. aureus-HA fusion protein is detected by radiolabeling and immunoprecipitation, using methods described in, for example Harlow et al., supra. To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 4

Cloning and Expression in CHO Cells

The vector pC4 is used for the expression of S. aureus polypeptide in this example. Plasmid pC4 is a derivative of the plasmid pSV2-dhfr (ATCC Accession No. 37146). The plasmid contains the mouse DHFR gene under control of the SV40 early promoter. Chinese hamster ovary cells or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented. See, e.g., Alt et al., 1978, J. Biol. Chem. 253:1357–1370; Hamlin et al., 1990, Biochem. et Biophys. Acta, 1097:107–143; Page et al., 1991, Biotechnology 9:64–68. Cells grown in increasing concentrations of MTX develop resistance to the drug by overproducing the target enzyme, DHFR, as a result of amplification of the DHFR gene. If a second gene is linked to the DHFR gene, it is usually co-amplified and overexpressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains the strong promoter of the long terminal repeat (LTR) of the Rouse Sarcoma Virus, for expressing a polypeptide of interest, Cullen, et al. (1985) Mol. Cell. Biol. 5:438–447; plus a fragment isolated from the enhancer of the immediate early gene of human cytomegalovirus (CMV), Boshart, et al., 1985, Cell 41:521–530. Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the $S.$ $aureus$ polypeptide in a regulated way in mammalian cells (Gossen et al., 1992, Proc. Natl. Acad. Sci. USA 89:5547–5551. For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes and then dephosphorylated using calf intestinal phosphates by procedures known in the art. The vector is then isolated from a 1% agarose gel. The DNA sequence encoding the $S.$ $aureus$ polypeptide is amplified using PCR oligonucleotide primers corresponding to the 5' and 3' sequences of the desired portion of the gene. A 5' primer containing a restriction site, a Kozak sequence, an AUG start codon, and nucleotides of the 5' coding region of the $S.$ $aureus$ polypeptide is synthesized and used. A 3' primer, containing a restriction site, stop codon, and nucleotides complementary to the 3' coding sequence of the $S.$ $aureus$ polypeptides is synthesized and used. The amplified fragment is digested with the restriction endonucleases and then purified again on a 1% agarose gel. The isolated fragment and the dephosphorylated vector are then ligated with T4 DNA ligase. $E.$ $coli$ HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five $\mu$g of the expression plasmid pC4 is cotransfected with 0.5 $\mu$g of the plasmid pSVneo using a lipid-mediated transfection agent such as Lipofectin™ or LipofectAMINE.™ (LifeTechnologies Gaithersburg, Md.). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 $\mu$M, 2 $\mu$M, 5 $\mu$M, 10 mM, 20 mM). The same procedure is repeated until clones are obtained which grow at a concentration of 100–200 $\mu$M. Expression of the desired gene product is analyzed, for instance, by SDS-PAGE and Western blot or by reversed phase HPLC analysis.

Example 5

Quantitative Murine Soft Tissue Infection Model for $S.$ $aureus$

Compositions of the present invention, including polypeptides and peptides, are assayed for their ability to function as vaccines or to enhance/stimulate an immune response to a bacterial species (e.g., $S.$ $aureus$) using the following quantitative murine soft tissue infection model. Mice (e.g., NIH Swiss female mice, approximately 7 weeks old) are first treated with a biologically protective effective amount, or immune enhancing/stimulating effective amount of a composition of the present invention using methods known in the art, such as those discussed above. See, e.g., Harlow et al., ANTIBODIES: A LABORATORY MANUAL, (Cold Spring Harbor Laboratory Press, 2nd ed. 1988). An example of an appropriate starting dose is 20 ug per animal.

The desired bacterial species used to challenge the mice, such as $S.$ $aureus$, is grown as an overnight culture. The culture is diluted to a concentration of $5\times10^8$ cfu/ml, in an appropriate media, mixed well, serially diluted, and titered. The desired doses are further diluted 1:2 with sterilized Cytodex 3 microcarrier beads preswollen in sterile PBS (3 g/100 ml). Mice are anesthetize briefly until docile, but still mobile and injected with 0.2 ml of the Cytodex 3 bead/bacterial mixture into each animal subcutaneously in the inguinal region. After four days, counting the day of injection as day one, mice are sacrificed and the contents of the abscess is excised and placed in a 15 ml conical tube containing 1.0 ml of sterile PBS. The contents of the abscess is then enzymatically treated and plated as follows.

The abscess is first disrupted by vortexing with sterilized glass beads placed in the tubes. 3.0 mls of prepared enzyme mixture (1.0 ml Collagenase D (4.0 mg/ml), 1.0 ml Trypsin (6.0 mg/ml) and 8.0 ml PBS) is then added to each tube followed by a 20 min. incubation at 37 C. The solution is then centrifuged and the supernatant drawn off. 0.5 ml dH20 is then added and the tubes are vortexed and then incubated for 10 min. at room temperature. 0.5 ml media is then added and samples are serially diluted and plated onto agar plates, and grown overnight at 37 C. Plates with distinct and separate colonies are then counted, compared to positive and negative control samples, and quantified. The method can be used to identify composition and determine appropriate and effective doses for humans and other animals by comparing the effective doses of compositions of the present invention with compositions known in the art to be effective in both mice and humans. Doses for the effective treatment of humans and other animals, using compositions of the present invention, are extrapolated using the data from the above experiments of mice. It is appreciated that further studies in humans and other animals may be needed to determine the most effective doses using methods of clinical practice known in the art.

Example 6

Murine Systemic Neutropenic Model for *S. aureus* Infection

Compositions of the present invention, including polypeptides and peptides, are assayed for their ability to function as vaccines or to enhance/stimulate an immune response to a bacterial species (e.g., *S. aureus*) using the following qualitative murine systemic neutropenic model. Mice (e.g., NIH Swiss female mice, approximately 7 weeks old) are first treated with a biologically protective effective amount, or immune enhancing/stimulating effective amount of a composition of the present invention using methods known in the art, such as those discussed above. See, e.g., Harlow et al., ANTIBODIES: A LABORATORY MANUAL, (Cold Spring Harbor Laboratory Press, 2nd ed. 1988). An example of an appropriate starting dose is 20 ug per animal.

Mice are then injected with 250–300 mg/kg cyclophosphamide intraperitonially. Counting the day of C.P. injection as day one, the mice are left untreated for 5 days to begin recovery of PMNL'S.

The desired bacterial species used to challenge the mice, such as *S. aureus*, is grown as an overnight culture. The culture is diluted to a concentration of $5 \times 10^8$ cfu/ml, in an appropriate media, mixed well, serially diluted, and titered. The desired doses are further diluted 1:2 in 4% Brewer's yeast in media.

Mice are injected with the bacteria/brewer's yeast challenge intraperitonially. The Brewer's yeast solution alone is used as a control. The mice are then monitored twice daily for the first week following challenge, and once a day for the next week to ascertain morbidity and mortality. Mice remaining at the end of the experiment are sacrificed. The method can be used to identify compositions and determine appropriate and effective doses for humans and other animals by comparing the effective doses of compositions of the present invention with compositions known in the art to be effective in both mice and humans. Doses for the effective treatment of humans and other animals, using compositions of the present invention, are extrapolated using the data from the above experiments of mice. It is appreciated that further studies in humans and other animals may be needed to determine the most effective doses using methods of clinical practice known in the art.

The disclosure of all publications (including patents, patent applications, journal articles, laboratory manuals, books, or other documents) cited herein are hereby incorporated by reference in their entireties.

The present invention is not to be limited in scope by the specific embodiments described herein, which are intended as single illustrations of individual aspects of the invention. Functionally equivalent methods and components are within the scope of the invention, in addition to those shown and described herein and will become apparent to those skilled in the art from the foregoing description and accompanying drawings. Such modifications are intended to fall within the scope of the appended claims.

What is claimed is:

1. An isolated polynucleotide encoding the amino acid sequence of SEQ ID NO:12.
2. The isolated polynucleotide of claim 1 which is fused to a heterologous polynucleotide sequence.
3. The isolated polynucleotide of claim 2, wherein said heterologous polynucleotide sequence encodes a heterologous polypeptide.
4. An isolated polynucleotide which is fully complementary to the polynucleotide of claim 1.
5. A method for making a recombinant vector comprising inserting the isolated polynucleotide of claim 1 into a vector.
6. A recombinant vector comprising the isolated polynucleotide of claim 1.
7. The recombinant vector of claim 6, wherein said isolated polynucleotide is operably associated with a heterologous regulatory sequence that controls gene expression.
8. An isolated recombinant host cell comprising the isolated polynucleotide of claim 1.
9. The isolated recombinant host cell of claim 8, wherein said polynucleotide is operably associated with a heterologous regulatory sequence that controls gene expression.
10. A method for producing a polypeptide, comprising culturing the host cell of claim 8 under conditions suitable to produce the polypeptide encoded by said polynucleotide.
11. An isolated polynucleotide comprising the nucleotide sequence of SEQ ID NO:11.
12. An isolated polynucleotide which is fully complementary to the polynucleotide of claim 11.
13. An isolated polynucleotide consisting of the full length sequence of SEQ ID NO:11.
14. An isolated polynucleotide consisting of a nucleic acid sequence encoding an epitope-bearing portion of the amino acid sequence of SEQ ID NO:12 is selected from the group consisting of:

(a) Glu-7 to Asp-11;
(b) Ile-18 to Lys-20;
(c) Ile-55 to Glu-59;
(d) Ser-66 to Gly-77;
(e) Thr-92 to Thr-97;
(f) Arg-123 to Asp-127;
(g) Lys-154 to Asp-159;
(h) Ile-166 to Gln170;
(i) Lys-618 to Thr-621;
(j) Gly-628 to Val-632;
(k) Asp-643 to Lys-646;
(l) Asp-667 to Arg-670;
(m) Gly-681 to Asp-684; and
(n) Asn-686 to Lys-689.

* * * * *